United States Patent
Ohashi et al.

(10) Patent No.: US 9,122,155 B2
(45) Date of Patent: *Sep. 1, 2015

(54) SULFONIUM SALT, RESIST COMPOSITION AND PATTERNING PROCESS

(71) Applicant: SHIN-ETSU CHEMICAL CO., LTD., Tokyo (JP)

(72) Inventors: Masaki Ohashi, Jyoetsu (JP); Tomohiro Kobayashi, Jyoetsu (JP); Akihiro Seki, Jyoetsu (JP); Masayoshi Sagehashi, Jyoetsu (JP); Masahiro Fukushima, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/103,462

(22) Filed: Dec. 11, 2013

(65) Prior Publication Data

US 2014/0199630 A1     Jul. 17, 2014

(30) Foreign Application Priority Data

Jan. 11, 2013     (JP) ................................. 2013-003768

(51) Int. Cl.
- G03F 7/004 (2006.01)
- C07C 309/06 (2006.01)
- C07C 381/12 (2006.01)

(52) U.S. Cl.
CPC ............ G03F 7/0045 (2013.01); C07C 309/06 (2013.01); C07C 381/12 (2013.01)

(58) Field of Classification Search
CPC ..... G03F 7/004; G03F 7/0046; G03F 7/0392; G03F 7/0397; G03F 7/2041; G03F 7/30; G03F 7/38; G03F 7/203; G03F 7/2037; C07C 309/06; C07D 333/46
USPC ........................ 430/270.1, 326, 921, 922, 925
See application file for complete search history.

(56) References Cited

U.S. PATENT DOCUMENTS

| | | | |
|---|---|---|---|
| 5,650,483 A | 7/1997 | Malik et al. | |
| 6,187,504 B1 | 2/2001 | Suwa et al. | |
| 6,312,867 B1 | 11/2001 | Kinsho et al. | |
| 2003/0013039 A1 | 1/2003 | Kobayashi et al. | |
| 2006/0194982 A1 | 8/2006 | Harada et al. | |
| 2006/0228648 A1 | 10/2006 | Ohsawa et al. | |
| 2008/0085469 A1 | 4/2008 | Ohsawa et al. | |
| 2008/0090172 A1 | 4/2008 | Hatakeyama et al. | |
| 2008/0187860 A1 | 8/2008 | Tsubaki et al. | |
| 2009/0011366 A1 | 1/2009 | Tsubaki et al. | |
| 2009/0081588 A1 | 3/2009 | Hatakeyama et al. | |
| 2009/0111047 A1 | 4/2009 | Yamashita | |
| 2009/0208867 A1 | 8/2009 | Harada et al. | |
| 2009/0208873 A1 | 8/2009 | Harada et al. | |
| 2009/0246694 A1 | 10/2009 | Ohsawa et al. | |
| 2009/0274978 A1 | 11/2009 | Ohashi et al. | |
| 2009/0280434 A1 | 11/2009 | Harada et al. | |
| 2010/0035185 A1 | 2/2010 | Hagiwara et al. | |
| 2010/0112482 A1 | 5/2010 | Watanabe et al. | |
| 2010/0136482 A1 | 6/2010 | Harada et al. | |
| 2010/0209827 A1 | 8/2010 | Ohashi et al. | |
| 2010/0266957 A1 | 10/2010 | Harada et al. | |
| 2011/0008735 A1 | 1/2011 | Ohsawa et al. | |

(Continued)

FOREIGN PATENT DOCUMENTS

| | | |
|---|---|---|
| JP | A-2000-336121 | 12/2000 |
| JP | A-2003-066612 | 3/2003 |

(Continued)

OTHER PUBLICATIONS

Dammel et al., "193 nm Immersion Lithography—Taking the Plunge," *Journal of Photopolymer Science and Technology*, 2004, pp. 587-601, vol. 17, No. 4.
U.S. Appl. No. 14/099,678, filed Dec. 6, 2013, in the name of Ohashi et al.
Apr. 14, 2015 Office Action issued in Japanese Application No. 2013-003768.
Jun. 30, 2015 Office Action issued in Japanese Application No. 2013-003768.

*Primary Examiner* — Anca Eoff
(74) *Attorney, Agent, or Firm* — Oliff PLC

(57) ABSTRACT

A sulfonium salt used in a resist composition which gives a pattern having a high resolution, and small roughness in the photolithography using a high energy beam as a light source, and further difficultly eluted in water in the immersion lithography, and a resist composition containing the sulfonium salt, and a patterning process using the resist composition, wherein the sulfonium salt is represented by the following general formula (1a),

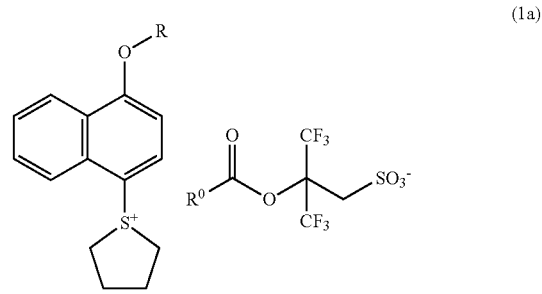

(1a)

wherein R represents a linear, branched, or cyclic monovalent hydrocarbon group having 1 to 30 carbon atoms at least one or more of the hydrogen atoms of which are substituted by a fluorine atom, $R^0$ represents a hydrogen atom, or a linear, branched, or cyclic monovalent hydrocarbon group having 1 to 30 carbon atoms which may be substituted by a halogen atom, or interposed by a heteroatom.

18 Claims, 2 Drawing Sheets

(56) References Cited

U.S. PATENT DOCUMENTS

| | | | |
|---|---|---|---|
| 2012/0100486 A1* | 4/2012 | Sagehashi et al. | 430/325 |
| 2014/0199629 A1* | 7/2014 | Ohashi et al. | 430/281.1 |

FOREIGN PATENT DOCUMENTS

| | | |
|---|---|---|
| JP | B2-3632410 | 3/2005 |
| JP | A-2006-257078 | 9/2006 |
| JP | A-2007-145797 | 6/2007 |
| JP | B2-3995575 | 10/2007 |
| JP | A-2007-298569 | 11/2007 |
| JP | A-2008-106045 | 5/2008 |
| JP | A-2008-122932 | 5/2008 |
| JP | A-2008-281974 | 11/2008 |
| JP | A-2008-281975 | 11/2008 |
| JP | A-2009-007327 | 1/2009 |
| JP | A-2009-098638 | 5/2009 |
| JP | A-2009-109595 | 5/2009 |
| JP | A-2009-191151 | 8/2009 |
| JP | A-2009-192784 | 8/2009 |
| JP | A-2009-258695 | 11/2009 |
| JP | A-2009-269953 | 11/2009 |
| JP | A-2009-276363 | 11/2009 |
| JP | A-2010-020204 | 1/2010 |
| JP | A-2010-107695 | 5/2010 |
| JP | A-2010-134012 | 6/2010 |
| JP | A-2010-215608 | 9/2010 |
| JP | B2-4554665 | 9/2010 |
| JP | A-2010-250105 | 11/2010 |
| JP | A-2011-016746 | 1/2011 |
| JP | A-2011-042789 | 3/2011 |
| JP | A-2012-046501 | 3/2012 |
| JP | 2012-106986 A | 6/2012 |
| JP | 2013-003167 A | 1/2013 |

* cited by examiner

_US 9,122,155 B2_

SULFONIUM SALT, RESIST COMPOSITION AND PATTERNING PROCESS

BACKGROUND OF THE INVENTION

1. Field of the Invention

The present invention relates to a sulfonium salt, a resist composition, and a patterning process.

2. Description of the Related Art

In recent years, as LSI advances toward a higher integration and a more rapid processing speed, finer pattern rules are being requested; and in this trend, a far ultraviolet lithography and a vacuum ultraviolet lithography are promising for the next generation fine patterning technologies. Especially, a photolithography using an ArF excimer laser beam as a light source is an indispensable technology for an ultrafine patterning process with the size of 0.13 µl or less.

The ArF lithography started to be used partially from manufacturing of a device with the 130-nm node, and then it became a main lithography technology from the 90-nm node device. As the lithography technology for the next 45-nm node device, a 157-nm lithography using a $F_2$ laser was initially considered as a promising technology; however, a delay in development thereof due to several problems was indicated. Accordingly, an ArF immersion lithography emerged rapidly because by inserting a liquid whose refractive index is higher than air, such as water, ethylene glycol, and glycerin, between a projection lens and a wafer, the number of aperture (NA) of the projection lens therein can be designed to be 1.0 or more thereby attaining a high resolution (for example, see Non-Patent Document 1); and this is now in the stage of practical use. For this immersion lithography, a resist composition not readily eluting into water is being requested.

In the ArF lithography, in order to avoid deterioration of a precise and expensive optical material, a highly sensitive resist composition that can express a sufficient resolution with a small exposure dose is requested; and in order to realize this, the most generally used method is to select each ingredient having a high transparency at the wavelength of 193 nm. As to a base resin for example, polyacrylic acid and a derivative thereof, norbornene-maleic acid anhydride alternating copolymer, polynorbornene, a ring-opened metathesis polymer, a hydrogenated ring-opened metathesis polymer, and the like have been proposed; and these bring about a certain level of results in enhancing a transparency of a resin.

In recent years, a negative tone resist by an organic solvent development as well as a positive tone resist by an alkaline development has been receiving an attention. In order to resolve a very fine hole pattern, which cannot be achieved by a positive tone, by a negative tone exposure, a negative pattern is formed by an organic solvent development using a positive resist composition having a high resolution. In addition, a study to obtain a doubled resolution power by combining two developments of the alkaline development and the organic solvent development is going on.

As to the ArF resist composition for the negative tone development by an organic solvent, an existing positive ArF resist composition can be used; and patterning processes thereof are disclosed in Patent Document 1 to 3.

In order to catch up the rapid fine patterning trend in recent years, development of a resist material as well as a process technology is progressing day by day. Various photo-sensitive acid generators have been studied; and a sulfonium salt of a triphenylsulfonium cation and a perfluoroalkane sulfonate anion is generally used. However, a generated acid of a perfluoroalkane sulfonic acid, especially perfluorooctane sulfonic acid (PFOS), has concerns about low degradability, biological concentration, and toxicity. And therefore, its use in the resist composition becomes difficult, so that currently a photo-sensitive acid generator to generate perfluorobutane sulfonic acid is being used; however, when this generator is used in the resist composition, it is difficult to achieve a high resolution because of a high diffusibility of the acid generated therefrom.

To the above problems, various partially fluorine substituted alkanesulfonic acids and salts thereof have been developed, and a photo-sensitive acid generator having 2-acyloxy-1,1,3,3,3-pentafluoropropane-1-sulfonic acid has been developed in the points of easiness in introducing a substituent which controls solubility into a resist solvent, stability, diffusibility, etc. (see Patent Document 4). Meanwhile, in Patent Document 4, as a conventional technology, a photo-sensitive acid generator generating an α,α-difluoroalkanesulfonic acid by exposure, more specifically a photo-sensitive acid generator generating di(4-tert-butylphenyl)iodonium=1,1-difluoro-2-(1-naphthyl)ethanesulfonate or an α,α,β,β-tetrafluoroalkanesulfonic acid has been mentioned. However, although in both generators, the fluorine substitution rates are reduced, there are problems that they do not have a decomposable substituent such as an ester structure, etc., so that they are insufficient in the viewpoint of degradability. Further, it involves the problems that there is a limitation in the molecular design to change the size of the alkanesulfonic acid, and the fluorine-containing starting substance is expensive, etc.

Further, a triphenylsulfonium cation has been widely used as a cation, but there is a drawback that absorption at ArF exposure wavelength (193 nm) is large, so that transmittance of the resist film is lowered and resolution is low in some cases. Thus, a 4-alkoxy-1-naphthyltetrahydrothiophenium cation, etc., have been developed (see Patent Document 5) for the purpose of a high sensitivity and a high resolution, and a resist composition with a combination of a resin(s) having a plural number of acid-labile groups (see Patent Document 6) has been disclosed.

However, accompanying with narrowing of a line width of a circuit, influence of the contrast degradation by an acid diffusion becomes still more serious in the resist composition. It is the present status that the above-mentioned sulfonium salts cannot meet the required performance of the resist. This is because the pattern dimensions get close the diffusion length of the acid. Specifically, it causes degradation of mask reliability and pattern rectangularity, unevenness of the fine line pattern (line width roughness: LWR), etc.

Also, since the sulfonium salt type photo-sensitive acid generator is an ionic compound, the point that it is easily eluted to water in the ArF immersion lithography than the other resist composition is one of the problems, so that a molecular design that is difficultly elute to water as much as possible has been desired.

PRIOR ART DOCUMENTS

Patent Documents

Patent Document 1: Japanese Patent Laid-Open Publication No. 2008-281974
Patent Document 2: Japanese Patent Laid-Open Publication No. 2008-281975
Patent Document 3: Japanese Patent No. 4554665
Patent Document 4: Japanese Patent Laid-Open Publication No. 2007-145797
Patent Document 5: Japanese Patent No. 3632410
Patent Document 6: Japanese Patent No. 3995575

Non-Patent Document

Non-Patent Document 1: Journal of photopolymer Science and Technology Vol. 17, No. 4, p 587 (2004)

SUMMARY OF THE INVENTION

The present invention was made in view of the above-mentioned circumstances, and an object thereof is to provide a sulfonium salt to be used for a resist composition which gives a good pattern having a high resolution, in particular, excellent in rectangularity of a pattern shape, and small roughness in the photolithography using a high energy beam such as ArF excimer laser light, EUV, etc., as a light source, and further difficultly eluted in water in the immersion lithography, and a resist composition containing the sulfonium salt, and a patterning process using the resist composition.

To solve the above-mentioned problems, the present invention provides a sulfonium salt represented by the following general formula (1a),

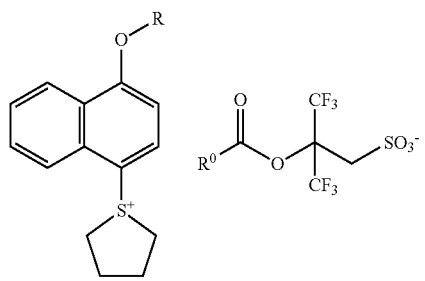

(1a)

wherein R represents a linear, branched, or cyclic monovalent hydrocarbon group having 1 to 30 carbon atoms at least one or more of hydrogen atoms of which are substituted by a fluorine atom, and $R^0$ represents a hydrogen atom, or a linear, branched, or cyclic monovalent hydrocarbon group having 1 to 30 carbon atoms which may be substituted by a halogen atom, or interposed by a heteroatom.

By using such a sulfonium salt as an acid generator (photo-sensitive acid generator), a resist composition having a high transparency and excellent in resolution, shape and roughness, and less elution of a salt component to immersion water can be obtained, and it can be made extremely useful for precise fine processing as a resist composition.

In this case, the above-mentioned formula (1a) is preferably represented by the following general formula (1b),

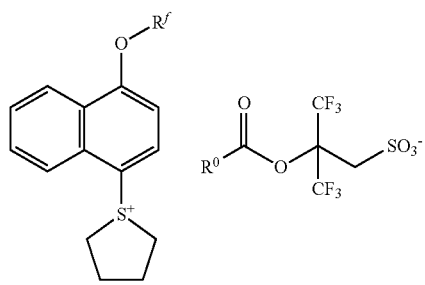

(1b)

wherein $R^0$ is as defined above, and $R^f$ represents an alkyl group having 1 to 4 carbon atoms at least one or more hydrogen atoms of which are substituted by a fluorine atom.

Such a sulfonium salt can be easily synthesized, and by using the same as an acid generator (photo-sensitive acid generator), a resist composition having a further higher transparency and excellent in resolution, shape and roughness, and less elution of a salt component to immersion water can be obtained, and it can be made extremely useful for precise fine processing as a resist composition.

In addition, the present invention provides a chemically amplified resist composition which comprises a base resin, an acid generator, and an organic solvent, wherein the acid generator is the sulfonium salt according to the present invention.

Such a chemically amplified resist composition has a high transparency and excellent in resolution, shape and roughness, and less elution of a salt component to immersion water, and thus, this can be made extremely useful for precise fine processing as a resist composition.

In this case, the above-mentioned base resin is preferably a polymer compound having a repeating unit represented by the following general formula (2) and a repeating unit represented by the following general formula (3),

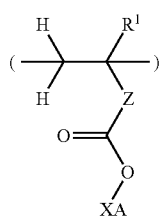

(2)

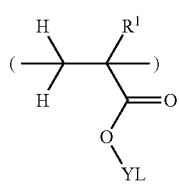

(3)

wherein $R^1$ represents a hydrogen atom, a fluorine atom, a methyl group or a trifluoromethyl group; Z represents any of a single bond, a phenylene group, a naphthylene group, and (main chain)-C(=O)—O—Z'—; Z' represents a phenylene group, a naphthylene group, or a linear, branched, or cyclic alkylene group having 1 to 10 carbon atoms which may have any of a hydroxyl group, an ether bond, an ester bond, and a lactone ring; XA represents an acid-labile group; and YL represents a hydrogen atom, or a polar group having one or more structures selected from a hydroxyl group, a cyano group, a carbonyl group, a carboxyl group, an ether bond, an ester bond, a sulfonate ester bond, a carbonate bond, a lactone ring, a sultone ring, and a carboxylic acid anhydride.

The chemically amplified resist composition containing the above-mentioned base resin has a further higher transparency and excellent resolution, shape and roughness, and less elution of a salt component to immersion water, and extremely useful for precise fine processing as a resist composition.

In this case, it is also preferable that the chemically amplified resist composition further contains at least any one of a basic compound and a surfactant.

Such a chemically amplified resist composition is preferable since the resolution can be more improved.

Further, the present invention provides a patterning process comprising a step of applying the chemically amplified resist composition onto a substrate, a step of exposure by a high energy beam after a heat treatment, and a step of development by using a developing solution.

By using such a patterning process of the present invention, an excellent pattern having an excellent resolution, in particular, excellent in rectangularity of a pattern shape, and small roughness, can be formed.

In this case, the above-mentioned exposure is preferably conducted by an immersion exposure interposed by a liquid having a refractive index of 1.0 or more between a resist coat film and a projection lens.

By using such a patterning process by the immersion exposure, a better pattern having an excellent resolution, in particular, excellent in rectangularity of a pattern shape, and small roughness, can be formed.

In addition, it is preferable that a protective coat is further applied on the resist coat film, and the immersion exposure is conducted interposed by the liquid between the protective coat and the projection lens.

Thus, by using the protective coat, the resist film can be protected, and further better pattern excellent in resolution, in particular, excellent in rectangularity of a pattern shape, and small roughness, can be formed.

In this case, the high energy beam for the exposure is preferably a KrF excimer laser, an ArF excimer laser, an electron beam, or a soft X-ray in the wavelength range of 3 to 15 nm. The acid generator of the present invention is suitable for the exposure using such a light source.

According to the sulfonium salt of the present invention, when it is contained in the chemically amplified resist composition as an acid generator (photo-sensitive acid generator), it can contribute to further improvement in resolution, shape and roughness than the conventional resist composition due to the structure, and it becomes extremely useful for precise fine processing as a resist composition.

DETAILED DESCRIPTION OF THE PREFERRED EMBODIMENTS

Figure 1:
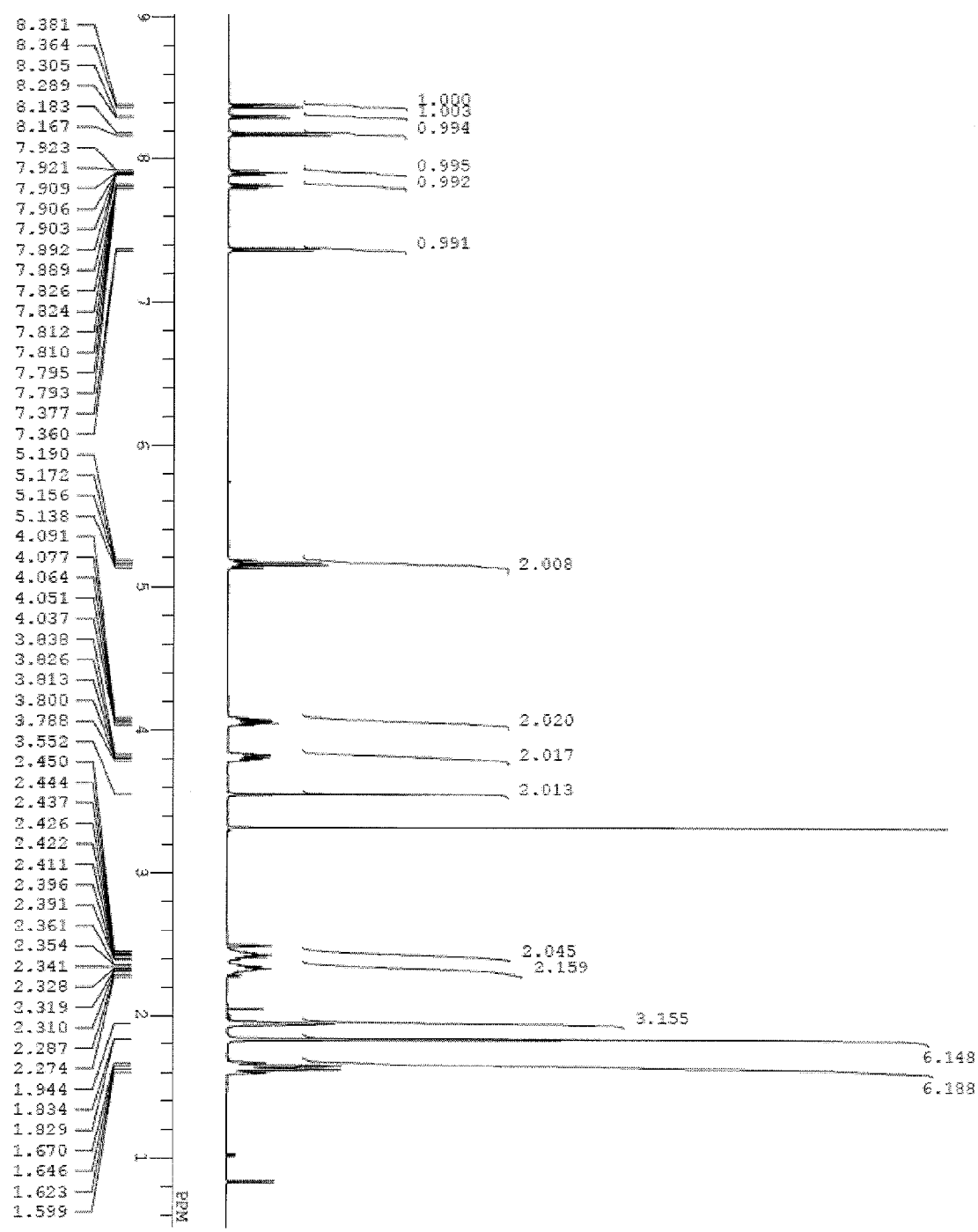
FIG. 1 shows $^1$H-NMR/DMSO-$d_6$ of the objective compound PAG-1 obtained in Synthesis Example 1-3.

In the following, the present invention will be explained in detail.

Inventors of the present invention have intensively studied to achieve the above-mentioned objects, and as a result, they have found out that a resist composition using a sulfonium salt represented by the following general formula (1a) as a photo-sensitive acid generator has a high transparency and excellent in resolution, shape and roughness, and less elution of a salt component to immersion water, and is extremely useful for precise fine processing as a resist composition; and based on this finding, the present invention could be completed.

That is, the present invention provides the following sulfonium salt, a resist composition containing the sulfonium salt and a patterning process.

In the following, the present invention is explained in more detail.

Firstly, the present invention provides a sulfonium salt represented by the following general formula (1a),

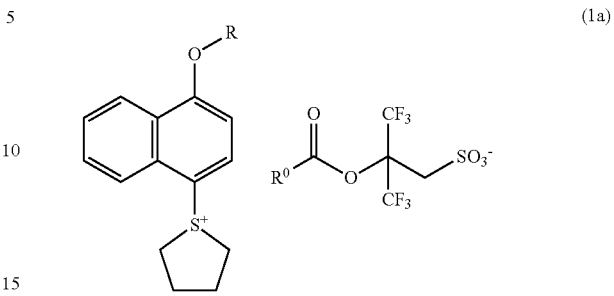

(1a)

wherein R represents a linear, branched, or cyclic monovalent hydrocarbon group having 1 to 30 carbon atoms at least one or more of hydrogen atoms of which are substituted by a fluorine atom; and $R^0$ represents a hydrogen atom, or a linear, branched, or cyclic monovalent hydrocarbon group having 1 to 30 carbon atoms which may be substituted by a halogen atom, or interposed by a heteroatom.

First, a cation portion of the sulfonium salt represented by the general formula (1a) will be explained in detail.

In the general formula (1a), R represents a linear, branched, or cyclic monovalent hydrocarbon group having 1 to 30 carbon atoms at least one or more of hydrogen atoms of which is substituted by a fluorine atom. The linear, branched, or cyclic monovalent hydrocarbon group having 1 to 30 carbon atoms may be exemplified by, for example, a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, an adamantyl group, etc., and one or more hydrogen atoms are substituted by a fluorine atom as R.

Subsequently, an anion portion of the sulfonium salt represented by the general formula (1a) will be explained in detail.

In the general formula (1a), $R^0$ represents a hydrogen atom, or a linear, branched, or cyclic monovalent hydrocarbon group having 1 to 30 carbon atoms which may be substituted by a halogen atom, or interposed by a heteroatom. More specifically, there may be exemplified by a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, an adamantyl group, etc. In addition, a part of hydrogen atoms of these groups may be substituted by a heteroatom such as an oxygen atom, a sulfur atom, a nitrogen atom, and a halogen atom, or a heteroatom such as an oxygen atom, a sulfur atom, a nitrogen atom, etc., may be interposed, and as a result, it may form or may be interposed by a hydroxy group, a cyano group, a carbonyl group, an ether bond, an ester bond, a sulfonate ester bond, a carbonate bond, a lactone ring, a sultone ring, a carboxylic acid anhydride, a haloalkyl group, etc.

Preferable structure of R⁰ in the general formula (1a) may be specifically exemplified by the following. However, the sulfonium salt of the present invention is not limited to these.

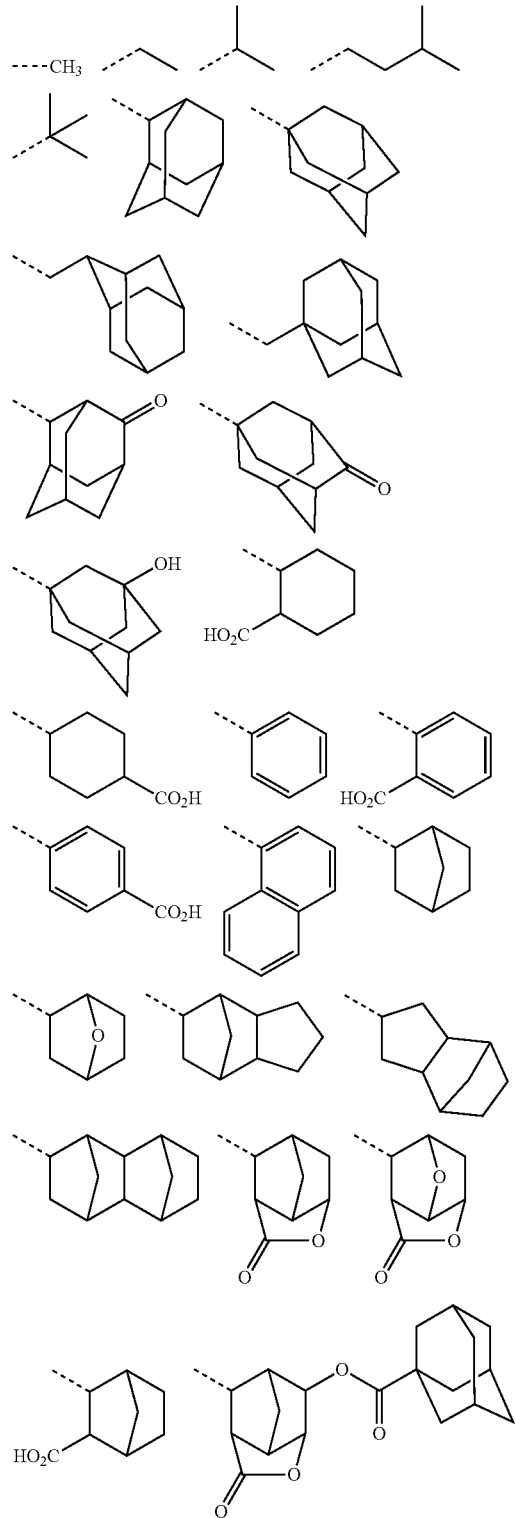

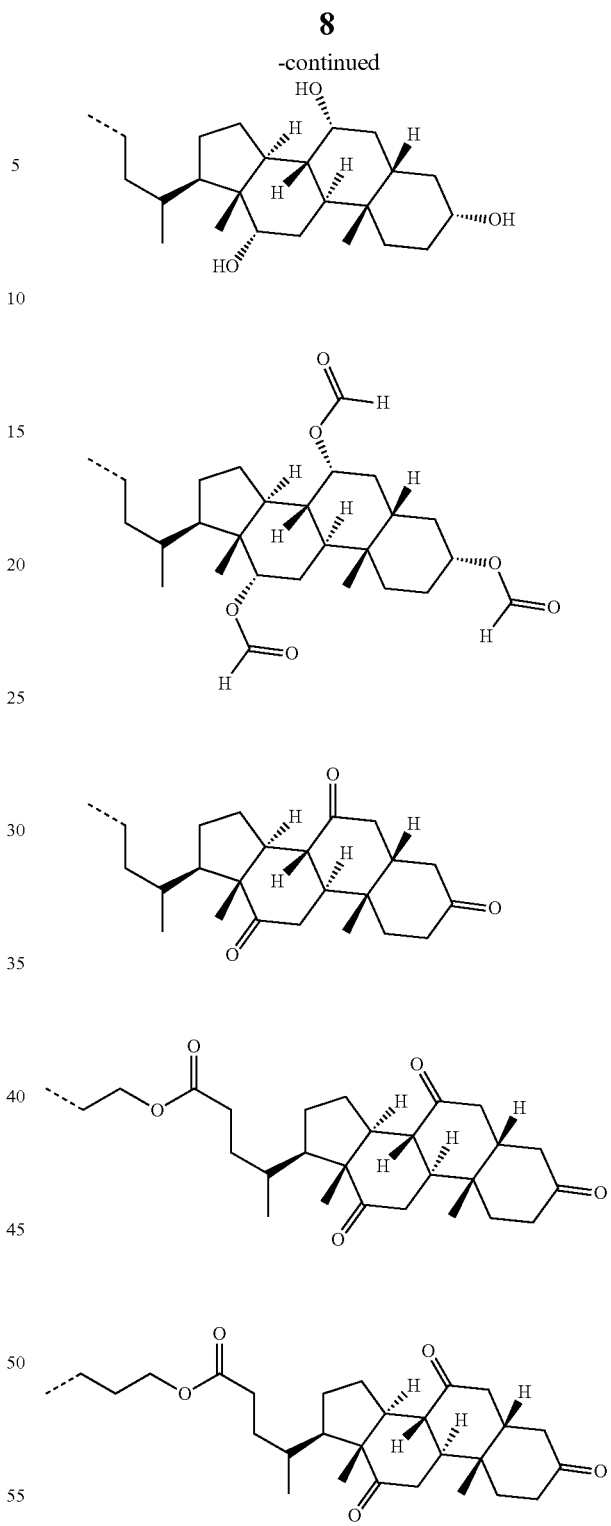

wherein the dotted line represents a bonding arm.

The sulfonium salt represented by the general formula (1a) may be exemplified by the structure in which the above-mentioned specific examples of the cation portion and the specific examples of the anion portion are combined.

In the sulfonium salt of the present invention, the above-mentioned formula (1a) is preferably represented by the following general formula (1b),

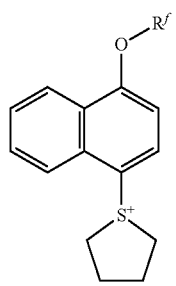
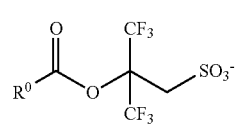

(1b)

wherein $R^0$ is as defined above, and $R^f$ represents an alkyl group having 1 to 4 carbon atoms at least one or more hydrogen atoms of which are substituted by a fluorine atom.

In the above-mentioned formula (1b), $R^0$ is already mentioned specifically. $R^f$ represents an alkyl group having 1 to 4 carbon atoms at least one or more hydrogen atoms of which are substituted by a fluorine atom (a fluoroalkyl group). More specifically, the following may be exemplified.

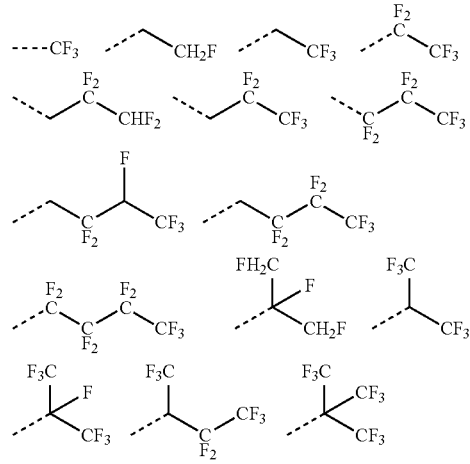

wherein the dotted line represents a bonding arm.

These $R^f$ groups are expected, for example, to reduce elution at the time of an immersion exposure by the water-repellent effect thereof. In particular, a 2,2,2-trifluoroethyl group or a 2,2,3,3,3-pentafluoropropyl group is suitably used in consideration with easiness in obtaining the starting materials and easiness in synthesis, etc. When the carbon number of $R^f$ group is 1 to 4, it is preferred since there is less possibility of showing the compound itself or a decomposed product thereof lipid solubility and highly condensing property when the compound is disposed after the present compound functioned as a resist composition. Also, when a long chain fluoroalkyl group is introduced, there are problems in synthesis or purification of the compound that crystallinity of the objective compound is lowered, or liquid separating property at the post-treatment becomes worse, etc., in many cases.

As the sulfonium salt represented by the above-mentioned formula (1b), a particularly suitably used example may be mentioned the following. However, the sulfonium salt of the present invention is not limited to these.

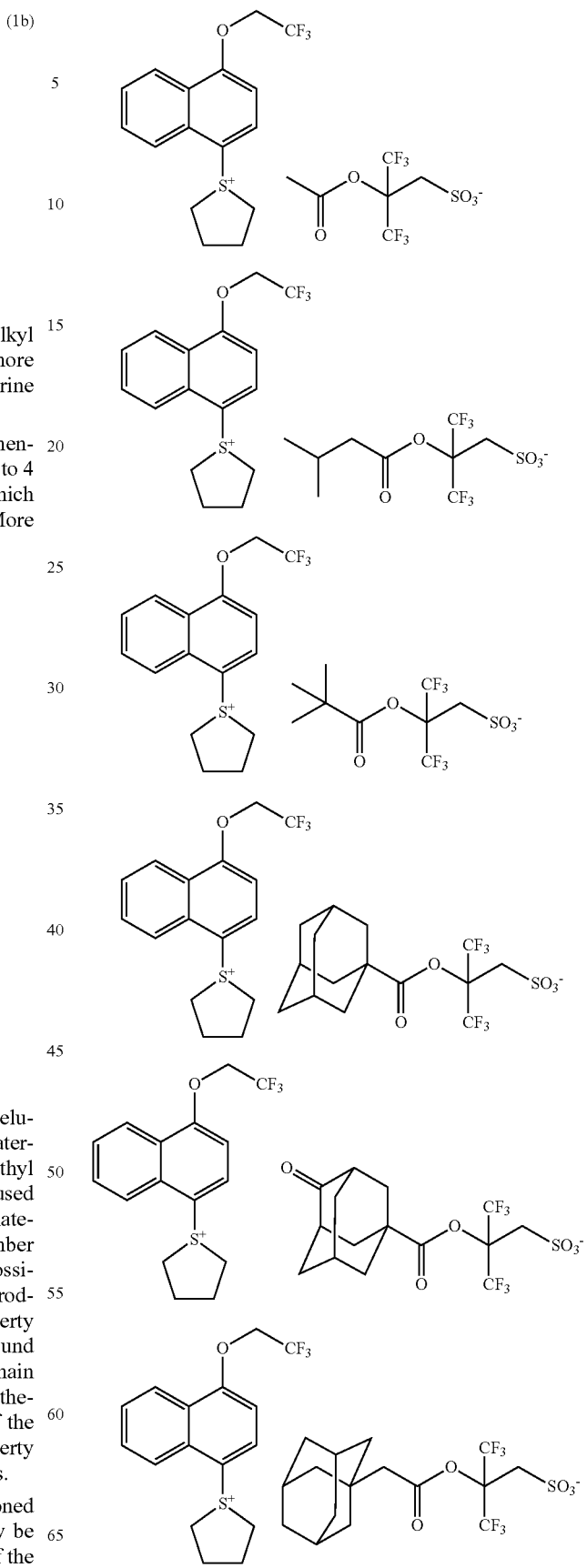

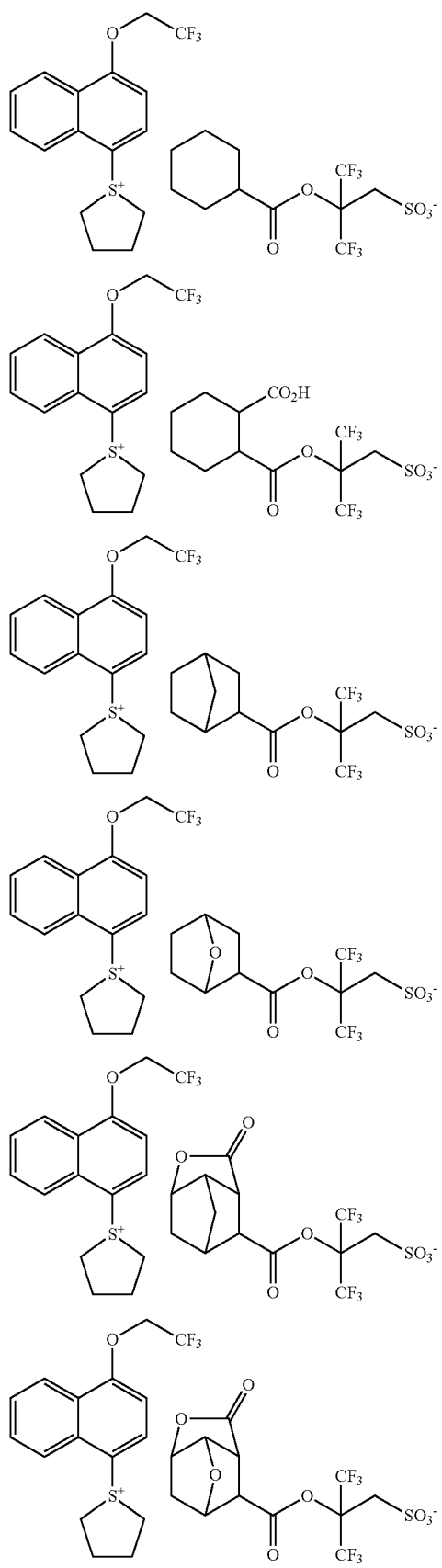
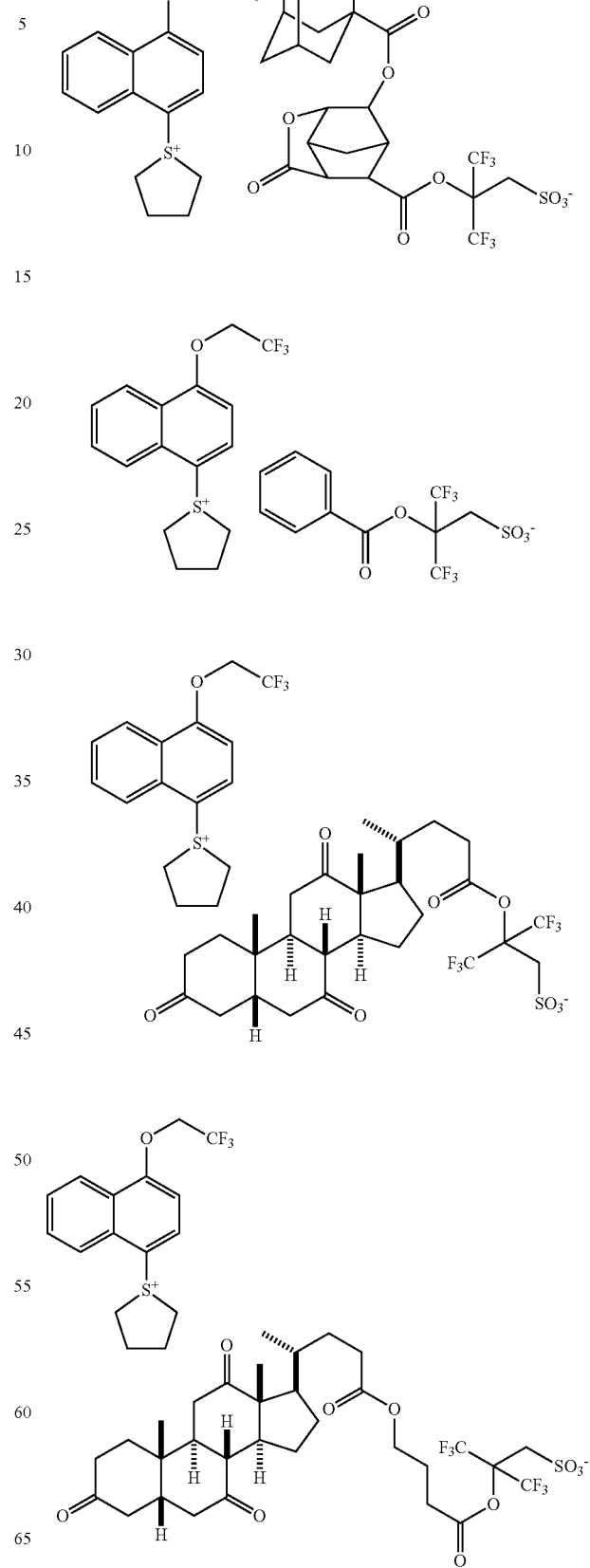

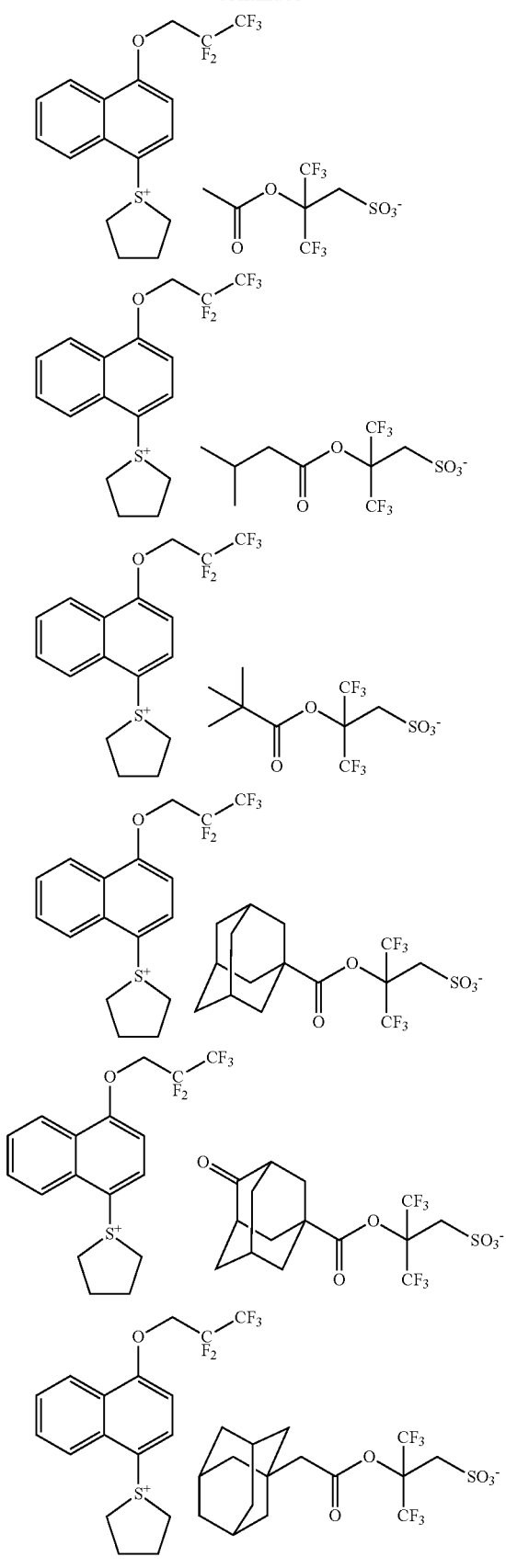
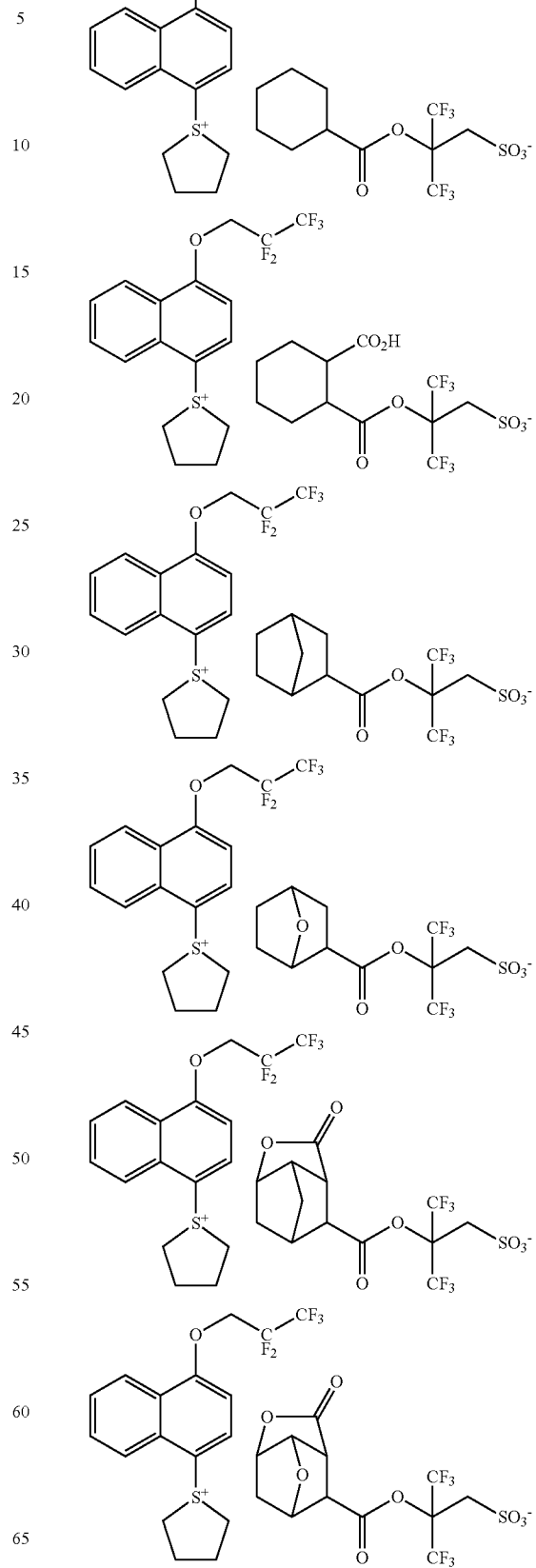

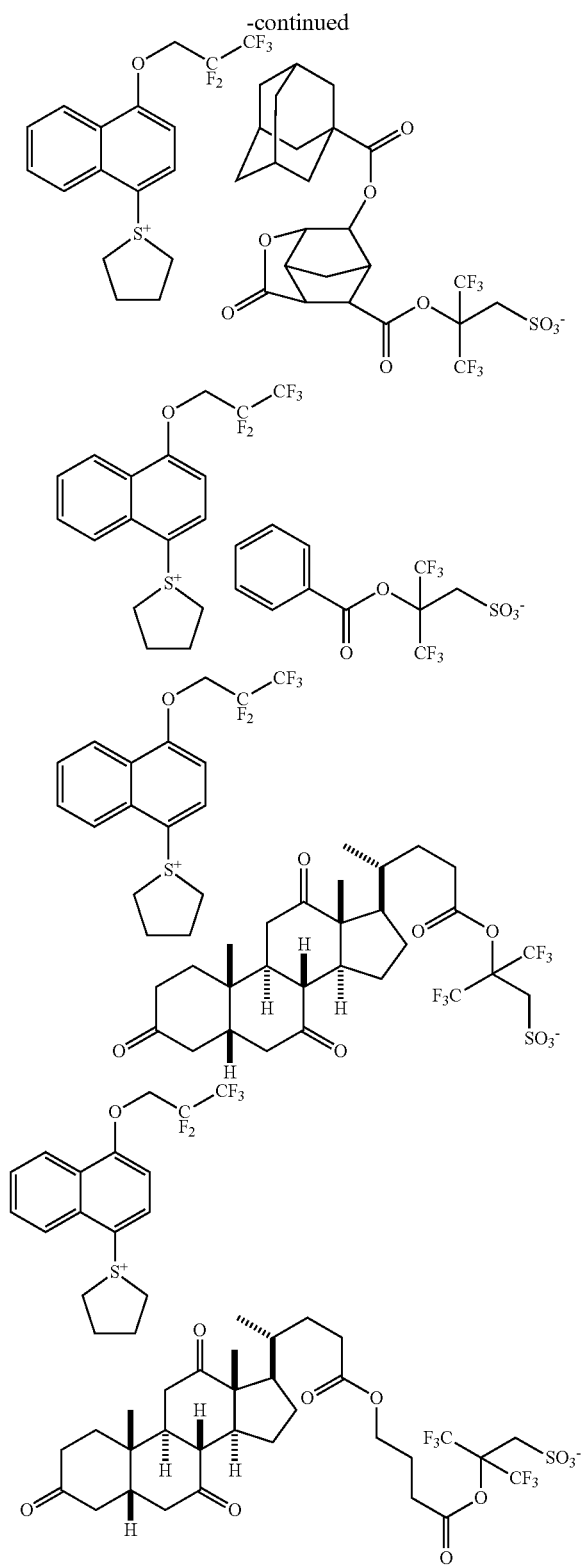

Here, the superior points of the sulfonium salt of the present invention will be mentioned. In the conventionally used perfluorobutanesulfonic acid anion, etc., acid strength of the generated acid is sufficient but diffusibility thereof is high. If the acid diffusion is large, various resist properties cannot be expressed, in particular, LWR cannot be lowered, but in the anion of the present invention, diffusibility can be controlled by selecting a suitable $R^0$. Also, in recent years, for example, an α,α-difluorosulfonate type partially fluorinated alkanesulfonic acid salt has been developed such as triphenylsulfonium=2-(adamantane-1-carbonyloxy)-1,1,3,3,3-pentafluoropropane-1-sulfonate as disclosed in Japanese Patent Laid-Open Publication No. 2007-145797 (Patent Document 4), and triphenylsulfonium=1-adamantylmethoxycarbonyl difluoromethane sulfonate as disclosed in Japanese Patent Laid-Open Publication No. 2006-257078, etc. These compounds have relatively high tolerance in modifying the structure, and it is possible to suppress acid diffusion with a certain extent depending on the substituent but it is insufficient to assure the desired properties of the lithography. On the other hand, in an anion structure of the sulfonium salt of the present invention, resulted from the position of the trifluoromethyl group at the β-position of the sulfo group, an acidity of the generated acid is slightly weaker than the above-mentioned prior art examples, and accordingly, it shows a behavior that the acid diffusion is apparently suppressed. As a result, the sulfonium salt of the present invention can lower LWR as compared with the conventional sulfonium salt.

Also, in the sulfonium salt of the present invention, resulted from a cation structure thereof, transparency is suitably assured without markedly impairing an acid generating efficiency, so that a pattern having a high resolution, in particular, excellent in rectangularity can be formed. Such a 1-naphthyltetrahydrothiophenium cation has already been developed as disclosed in, for example, Japanese Patent No. 3632410 (Patent Document 5), and it is excellent in resolution with a certain extent, but a suppressing ability of acid diffusion is insufficient, and LWR was not satisfactorily lowered. Therefore, by using the sulfonium salt having the cation portion and the anion portion of the present invention, a resist composition which can assure excellent resolution and shape as well as excellent in LWR which was not conventionally present is provided.

Further, the sulfonium salt of the present invention has a fluoroalkyl group at the cation portion so that a water-repellent effect appears and, for example, at the time of an immersion exposure using water, an effect of reducing elution (leaching) of the sulfonium salt to water can be expected. In particular, the structure represented by the general formula (1b) is preferable since synthesis and obtaining starting materials are relatively easy in addition to the above-mentioned effects. Therefore, the sulfonium salt of the present invention is particularly useful for ArF immersion lithography.

The sulfonium cation of the above-mentioned formula (1a) or (1b) can be easily synthesized by the conventionally known method comprising two steps of i) synthesis of an alkoxynaphthalene, and ii) synthesis of a sulfonium cation. For example, in the above-mentioned formula (1a), when R is a 2,2,2-trifluoroethyl group, i) p-toluenesulfonic acid=2,2,2-trifluoroethyl or 1-iodo 2,2,2-trifluoroethane and 1-naphthol are reacted under the basic conditions to synthesize 1-(2,2,2-trifluoroethyl)naphthalene. ii) Subsequently, the resulting compound and tetramethylene sulfoxide are reacted in a diphosphorus pentaoxide/methanesulfonic acid solution to synthesize a sulfonium cation. In the case that R is other substituent; a corresponding sulfonium cation can be synthesized by the similar manner.

The anion of the sulfonium salt represented by the general formula (1a) or (1b) can be synthesized by using Japanese Patent Laid-Open Publication No. 2010-215608 as a reference.

An ion-exchange reaction of the above-mentioned cation and the anion can be carried out in an organic solvent alone such as dichloromethane, ethyl acetate, methyl isobutyl ketone, methanol, ethanol, acetonitrile, etc., or in combination with water.

The above-mentioned sulfonium cation and the sulfonate anion can be optionally selected a suitable combination in consideration with stability of the sulfonium cation in the resist composition, the acid generation efficiency at an exposure wavelength, or diffusibility of the generated acid, etc.

Secondary, the present invention can provide a chemically amplified resist composition comprising: as essential components, (A) the sulfonium salt represented by the general formula (1a) or (1b), (B) a base resin, and (C) an organic solvent; and as other components, (D) a basic compound (a quencher), (E) a surfactant insoluble or difficultly soluble in water and soluble in an alkaline developing solution, and/or a surfactant insoluble or difficultly soluble in water and an alkaline developing solution (a hydrophobic resin), and further, if necessary, (F) a photo-sensitive acid generator other than the sulfonium salt represented by the general formula (1a) or (1b) (photo-sensitive acid generator), and further, if necessary (G) an organic acid derivative and/or a fluorine substituted alcohol, etc.

The sulfonium salt (photo-sensitive acid generator) of Component (A) of the present invention is as described above, and a blending amount thereof is preferably 0.1 to 40 parts (parts by mass, hereinafter the same), in particular, 1 to 20 parts relative to 100 parts of the base resin in the resist composition.

(B) Base Resin

The base resin to be used for the resist composition of the present invention is preferably a polymer compound containing a repeating unit represented by the following general formula (2) and a repeating unit represented by the following general formula (3),

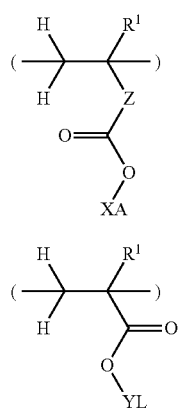

(2)

(3)

wherein $R^1$ represents a hydrogen atom, a fluorine atom, a methyl group or a trifluoromethyl group; Z represents any of a single bond, a phenylene group, a naphthylene group, and a (main chain)-C(=O)—O—Z'—; Z' represents a phenylene group, a naphthylene group, or a linear, branched, or cyclic alkylene group having 1 to 10 carbon atoms which may have any of a hydroxyl group, an ether bond, an ester bond, and a lactone ring; XA represents an acid-labile group; and YL represents a hydrogen atom, or a polar group having one or more structures selected from a hydroxyl group, a cyano group, a carbonyl group, a carboxyl group, an ether bond, an ester bond, a sulfonate ester bond, a carbonate bond, a lactone ring, a sultone ring, and a carboxylic acid anhydride.

A structure in which Z has been changed in the above-mentioned formula (2) may be more specifically exemplified by the following.

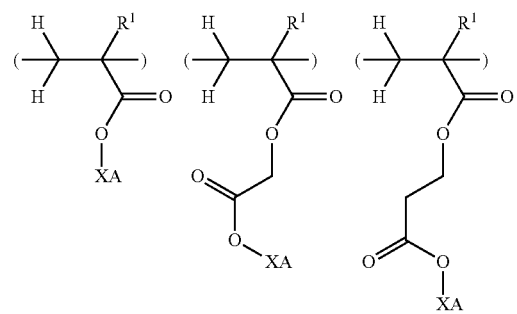

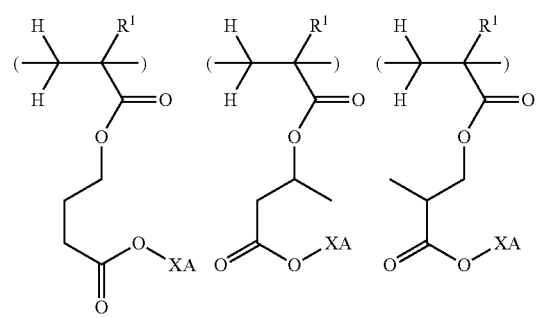

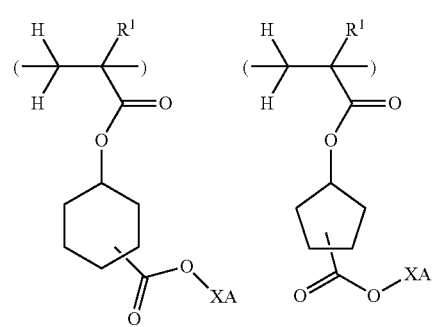

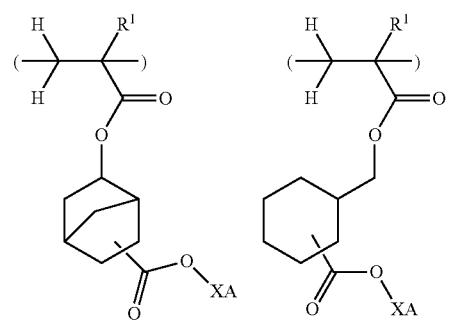

-continued

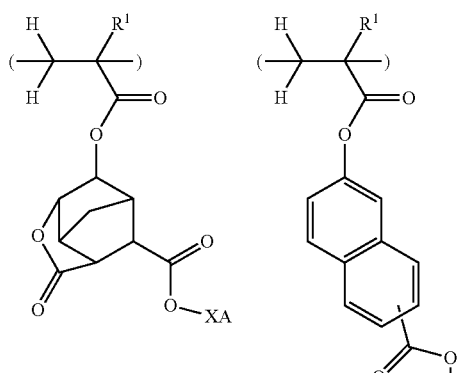

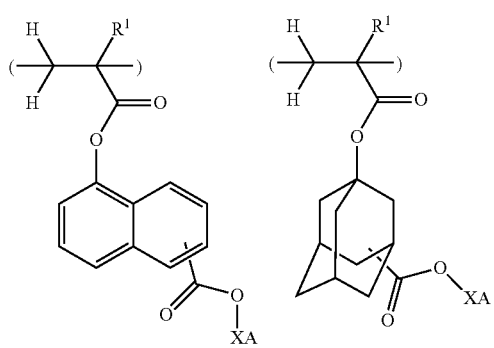

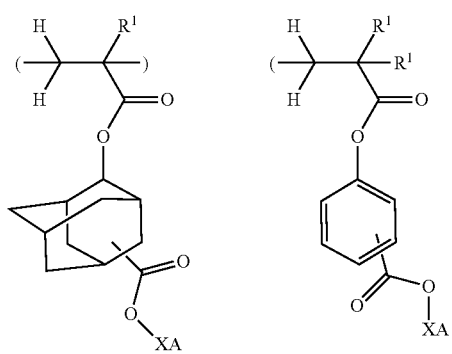

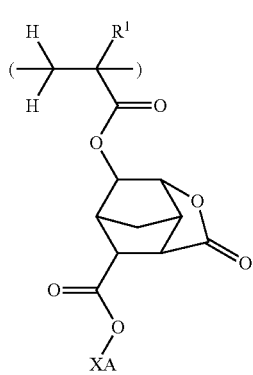

-continued

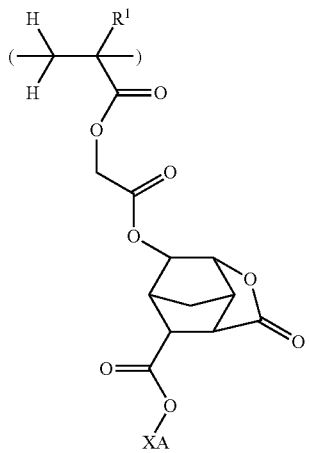

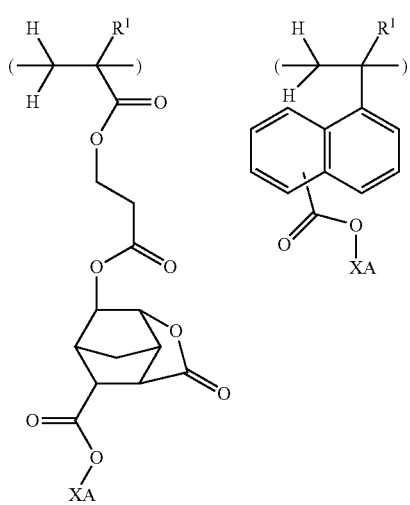

The polymer containing the above-mentioned repeating unit represented by the general formula (2) decomposes by the action of an acid to generate a carboxylic acid, and provide a polymer which is an alkali soluble. The acid-labile group XA may be used various kinds, and more specifically, there may be mentioned the groups represented by the following general formulae (L1) to (L4), a tertiary alkyl group having 4 to 20 carbon atoms, preferably 4 to 15 carbon atoms, a trialkylsilyl group in which each alkyl group has 1 to 6 carbon atoms, an oxoalkyl group having 4 to 20 carbon atoms, etc.

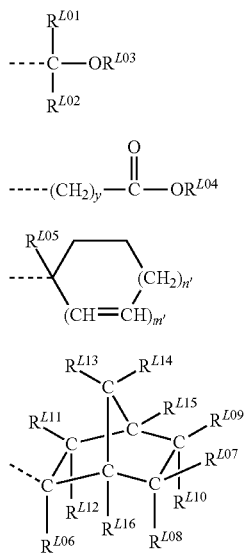

Here, the dotted line represents a bonding arm (hereinafter the same).

In the general formula (L1), $R^{L01}$ and $R^{L02}$ represent a hydrogen atom or a linear, branched, or cyclic alkyl group having 1 to 18 carbon atoms, preferably 1 to 10 carbon atoms, and specifically exemplified by a methyl group, an ethyl group, a propyl group, an isopropyl group, a n-butyl group, a sec-butyl group, a tert-butyl group, a cyclopentyl group, a cyclohexyl group, a 2-ethylhexyl group, a n-octyl group, a norbornyl group, a tricyclodecanyl group, a tetracyclododecanyl group, an adamantyl group, etc. $R^{L03}$ represents a monovalent hydrocarbon group having 1 to 18 carbon atoms, preferably 1 to 10 carbon atoms which may have a heteroatom such as an oxygen atom, etc., and may be mentioned those in which a part of the hydrogen atoms of the linear, branched, or cyclic alkyl group are substituted by a hydroxyl group, an alkoxy group, an oxo group, an amino group, an alkylamino group, etc., or those in which an oxygen atom is interposed between carbon atoms. Specific linear, branched, or cyclic alkyl group may be exemplified by a methyl group, an ethyl group, a propyl group, an isopropyl group, a n-butyl group, a sec-butyl group, a tert-butyl group, a cyclopentyl group, a cyclohexyl group, a 2-ethylhexyl group, a n-octyl group, a norbornyl group, a tricyclodecanyl group, a tetracyclododecanyl group, an adamantyl group, etc. Specific substituted alkyl groups may be exemplified by the following.

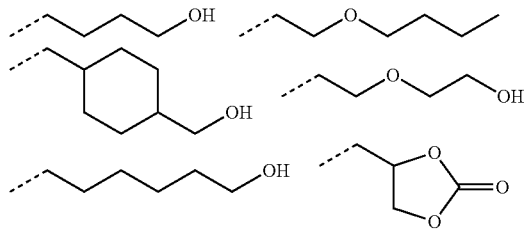

$R^{L01}$ and $R^{L02}$, $R^{L01}$ and $R^{L03}$, and $R^{L02}$ and $R^{L03}$ may be bonded to each other to form a ring with the carbon atom or the oxygen atom to which they are bonded, and when a ring is formed, the group which participate in the ring formation among $R^{L01}$, $R^{L02}$, $R^{L03}$ each represent a linear or branched alkylene group having 1 to 18 carbon atoms, preferably 1 to 10 carbon atoms.

In the general formula (L2), $R^{L04}$ represents a tertiary alkyl group having 4 to 20 carbon atoms, preferably 4 to 15 carbon atoms, a trialkylsilyl group each alkyl group of which having 1 to 6 carbon atoms, an oxoalkyl group having 4 to 20 carbon atoms, or the group represented by the above-mentioned formula (L1), the tertiary alkyl group may be specifically exemplified by a tert-butyl group, a tert-amyl group, a 1,1-diethylpropyl group, a 2-cyclopentylpropane-2-yl group, a 2-cyclohexylpropane-2-yl group, a 2-(bicyclo-[2.2.1]heptan-2-yl)propane-2-yl group, a 2-(adamantane-1-yl)propane-2-yl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, a 2-methyl-2-adamantyl group, a 2-ethyl-2-adamantyl group, etc., the trialkylsilyl group may be specifically exemplified by a trimethylsilyl group, a triethylsilyl group, a dimethyl-tert-butylsilyl group, etc., and the oxoalkyl group may be specifically exemplified by a 3-oxocyclohexyl group, a 4-methyl-2-oxoxan-4-yl group, a 5-methyl-2-oxooxolan-5-yl group, etc. Character y is an integer of 0 to 6.

In the general formula (L3), $R^{L05}$ represents a linear, branched, or cyclic alkyl group having 1 to 8 carbon atoms which may be substituted or an aryl group having 6 to 20 carbon atoms which may be substituted, the alkyl group which may be substituted may be specifically exemplified by a linear, branched, or cyclic alkyl group such as a methyl group, an ethyl group, a propyl group, an isopropyl group, a n-butyl group, a sec-butyl group, a tert-butyl group, a tert-amyl group, a n-pentyl group, a n-hexyl group, a cyclopentyl group, a cyclohexyl group, etc., and these groups having a part of the hydrogen atoms thereof substituted by a hydroxyl group, an alkoxy group, a carboxyl group, an alkoxycarbonyl group, an oxo group, an amino group, an alkylamino group, a cyano group, a mercapto group, an alkylthio group, a sulfo group, etc., the aryl group which may be substituted may be specifically exemplified by a phenyl group, a methylphenyl group, a naphthyl group, an anthryl group, a phenanthryl group, a pyrenyl group, etc. Character m' is 0 or 1, n' is any one of 0, 1, 2, and 3, and m' and n' are numbers satisfying 2 m'+n'=2 or 3.

In the general formula (L4), $R^{L06}$ represents a linear, branched, or cyclic alkyl group having 1 to 8 carbon atoms which may be substituted or an aryl group having 6 to 20 carbon atoms which may be substituted, and may be specifically exemplified by those of the same as $R^{L05}$, etc. Each of $R^{L07}$ to $R^{L16}$ independently represent a hydrogen atom or a monovalent hydrocarbon group having 1 to 15 carbon atoms, and may be specifically exemplified by a linear, branched, or cyclic alkyl group such as a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, etc., and these groups having a part of the hydrogen atoms thereof substituted by a hydroxyl group, an alkoxy group, a carboxyl group, an alkoxycarbonyl group, an oxo group, an amino group, an alkylamino group, a cyano group, a mercapto group, an alkylthio group, a sulfo group, etc. Two of $R^{L07}$ to $R^{L16}$ may be bonded to each other to form a ring with the carbon atoms to which these are bonded (for example, $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, and $R^{L13}$, and $R^{L14}$, etc.), and in such a case, that participating in the bonding represents a divalent hydrocarbon group having 1 to 15 carbon atoms, specifically exemplified by that one hydrogen atom is removed from the exemplified monovalent hydrocarbon group mentioned above, etc. Also, two of the $R^{LO7}$ to $R^{L16}$ may be bonded between the groups bonded to the adjacent carbon atoms to form a double bond without any interposition (for example, $R^{LO7}$ and $R^{LO9}$, $R^{LO9}$ and $R^{L15}$, $R^{L13}$ and $R^{L15}$, $R^{L14}$ and $R^{L15}$, etc.).

Among the acid-labile group represented by the above-mentioned formula (L1), a linear or branched one may be specifically exemplified by the following groups.

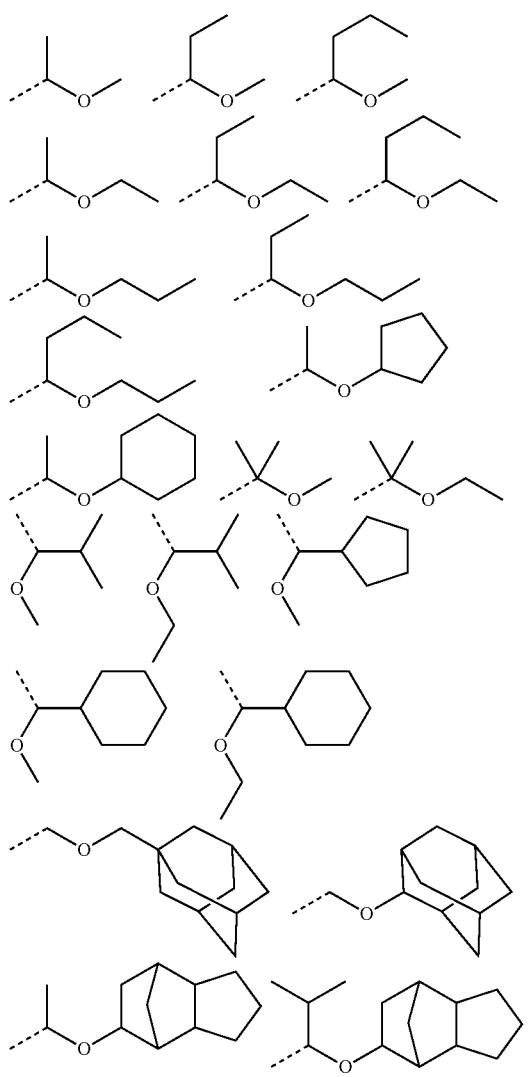

Among the acid-labile group represented by the above-mentioned formula (L1), a cyclic one may be specifically exemplified by a tetrahydrofuran-2-yl group, a 2-methyltetrahydrofuran-2-yl group, a tetrahydropyran-2-yl group, a 2-methyltetrahydropyran-2-yl group, etc.

The acid-labile group of the above-mentioned formula (L2) may be specifically exemplified by a tert-butoxycarbonyl group, a tert-butoxycarbonylmethyl group, a tert-amyloxycarbonyl group, a tert-amyloxycarbonylmethyl group, a 1,1-diethylpropyloxycarbonyl group, a 1,1-diethylpropyloxycarbonylmethyl group, a 1-ethylcyclopentyloxycarbonyl group, a 1-ethylcyclopentyloxycarbonylmethyl group, a 1-ethyl-2-cyclopentenyloxycarbonyl group, a 1-ethyl-2-cyclopentenyloxycarbonylmethyl group, a 1-ethoxyethoxycarbonylmethyl group, a 2-tetrahydropyranyloxycarbonylmethyl group, a 2-tetrahydrofuranyloxycarbonylmethyl group, etc.

The acid-labile group of the above-mentioned formula (L3) may be specifically exemplified by a 1-methylcyclopentyl group, a 1-ethylcyclopentyl group, a 1-n-propylcyclopentyl group, a 1-isopropylcyclopentyl group, a 1-n-butylcyclopentyl group, a 1-sec-butylcyclopentyl group, a 1-cyclohexylcyclopentyl group, a 1-(4-methoxy-n-butyl)cyclopentyl group, a 1-methylcyclohexyl group, a 1-ethylcyclohexyl group, a 3-methyl-1-cyclopenten-3-yl group, a 3-ethyl-1-cyclopenten-3-yl group, a 3-methyl-1-cyclohexen-3-yl group, a 3-ethyl-1-cyclohexen-3-yl group, etc.

The acid-labile group of the above-mentioned formula (L4) is particularly preferably the groups represented by the following general formulae (L4-1) to (L4-4).

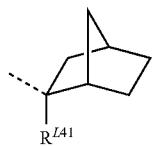

(L4-1)

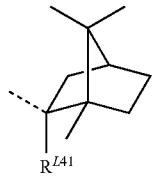

(L4-2)

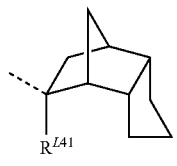

(L4-3)

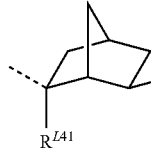

(L4-4)

In the above-mentioned formulae (L4-1) to (L4-4), the dotted line shows a bonding position and a bonding direction. Each of $R^{L41}$ independently represent a monovalent hydrocarbon group such as a linear, branched, or cyclic alkyl group having 1 to 10 carbon atoms, etc., more specifically, there may be exemplified by a methyl group, an ethyl group, a propyl group, an isopropyl group, an n-butyl group, a sec-butyl group, a tert-butyl group, a tert-amyl group, an n-pentyl group, an n-hexyl group, a cyclopentyl group, a cyclohexyl group, etc.

In the above-mentioned formulae (L4-1) to (L4-4), an enantioisomer (enantiomer) or a diastereoisomer (diastereomer) can exist, and above-mentioned formulae (L4-1) to (L4-4) represent all of these stereoisomers. These stereoisomers may be used solely, or may be used as a mixture.

For example, the above-mentioned formulae (L4-3) represent one kind or two kinds of mixture selected from the group represented by the following general formulae (L4-3-1) and (L4-3-2).

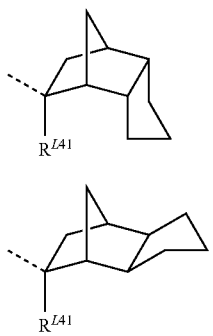

(L4-3-1)

(L4-3-2)

Also, the above-mentioned formulae (L4-4) represent one kind or two or more kinds of mixture selected from the group represented by the following general formulae (L4-4-1) to (L4-4-4).

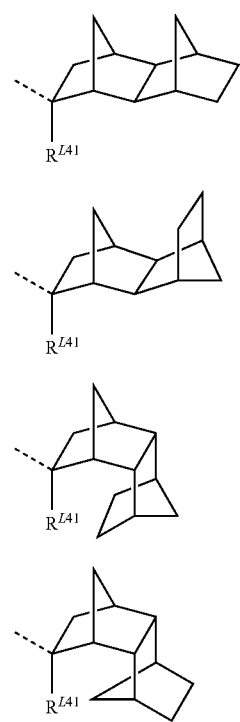

(L4-4-1)

(L4-4-2)

(L4-4-3)

(L4-4-4)

The above-mentioned formulae (L4-1) to (L4-4), (L4-3-1), (L4-3-2) and (L4-4-1) to (L4-4-4) represent also enantioisomers thereof and enantioisomers mixture.

Meanwhile, each of the bonding direction of the general formulae (L4-1) to (L4-4), (L4-3-1), (L4-3-2), and (L4-4-1) to (L4-4-4) is an exo side to the bicyclo[2.2.1]heptane ring, therefore a high reactivity can be realized in an acid catalyzed elimination reaction (see Japanese Patent Laid-Open Publication No. 2000-336121). In the production of a monomer having a tertiary exo-alkyl group which has a bicyclo[2.2.1] heptane skeleton as a substituent, a monomer substituted by the endo-alkyl group represented by the following general formulae (L4-1-endo) to (L4-4-endo) is included in some cases, and for realizing good reactivity, the exo ratio is preferably 50 mol % or more, and the exo ratio is further preferably 80 mol % or more.

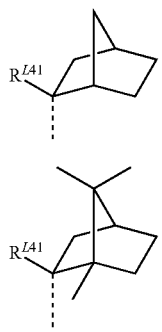

(L4-1-endo)

(L4-2-endo)

(L4-3-endo)

(L4-4-endo)

The acid-labile group of the above-mentioned formula (L4) may be specifically exemplified by the following groups.

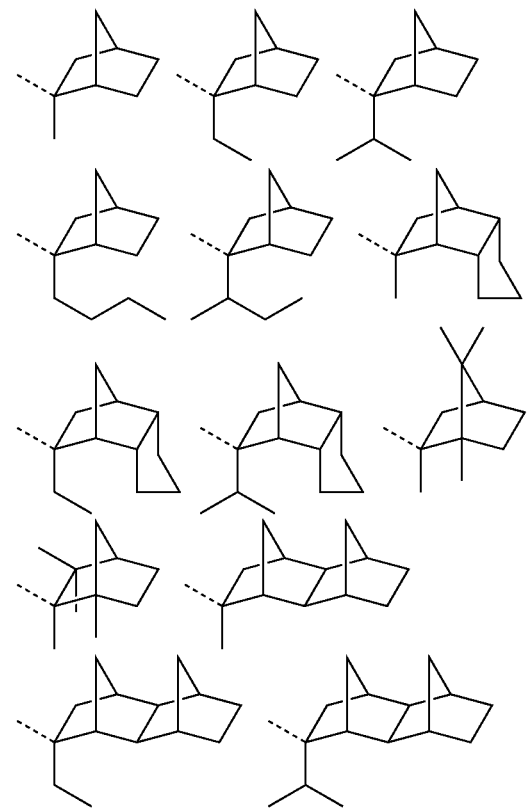

The tertiary alkyl group having 4 to 20 carbon atoms, the trialkylsilyl group in which each alkyl group has 1 to 6 carbon atoms, and the oxoalkyl group having 4 to 20 carbon atoms may be specifically exemplified by those of the same as mentioned in $R^{LO4}$, etc.
The above-mentioned repeating unit represented by the general formula (2) may be specifically exemplified by the followings, but not limited to them.
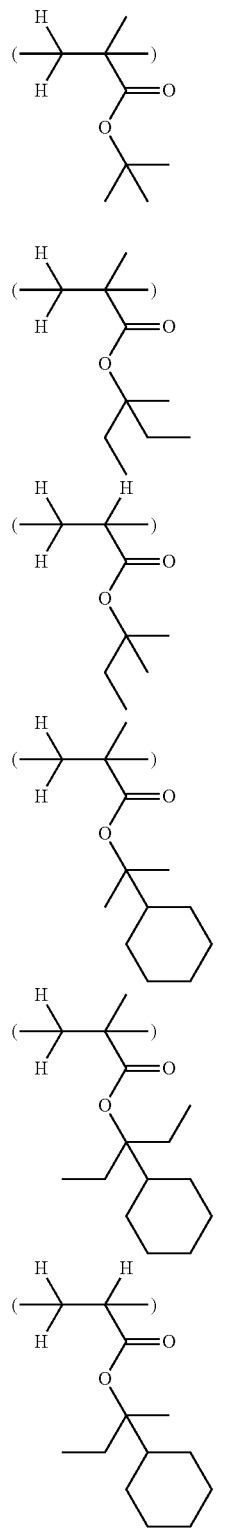
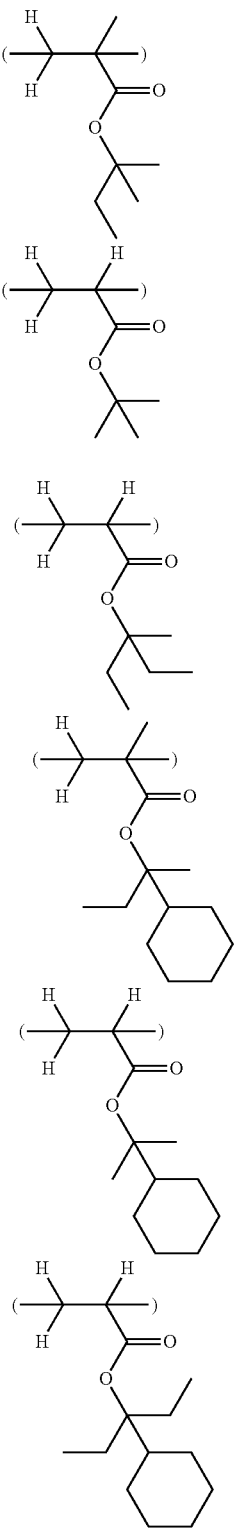
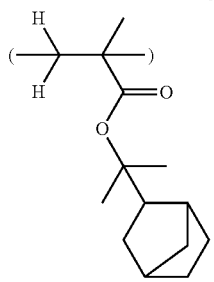
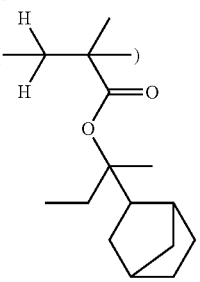
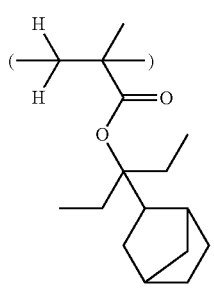
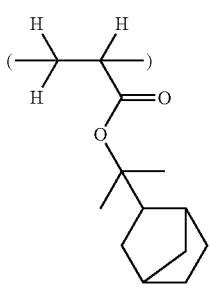
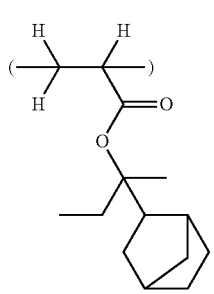
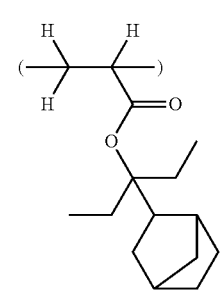
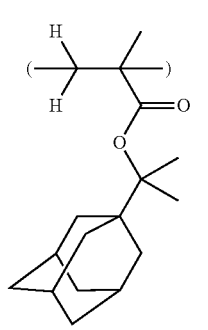
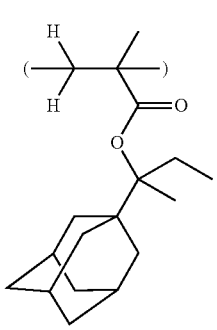
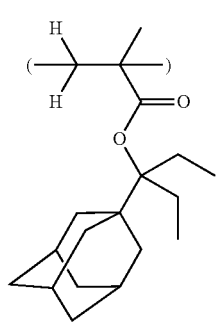
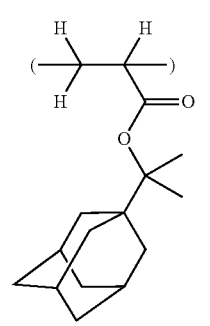

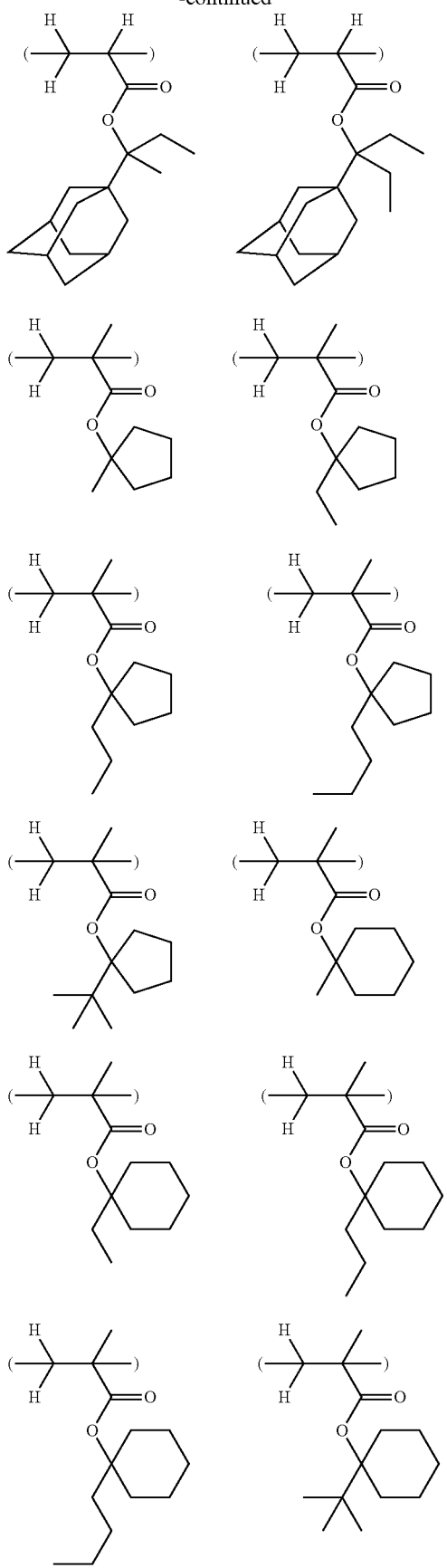
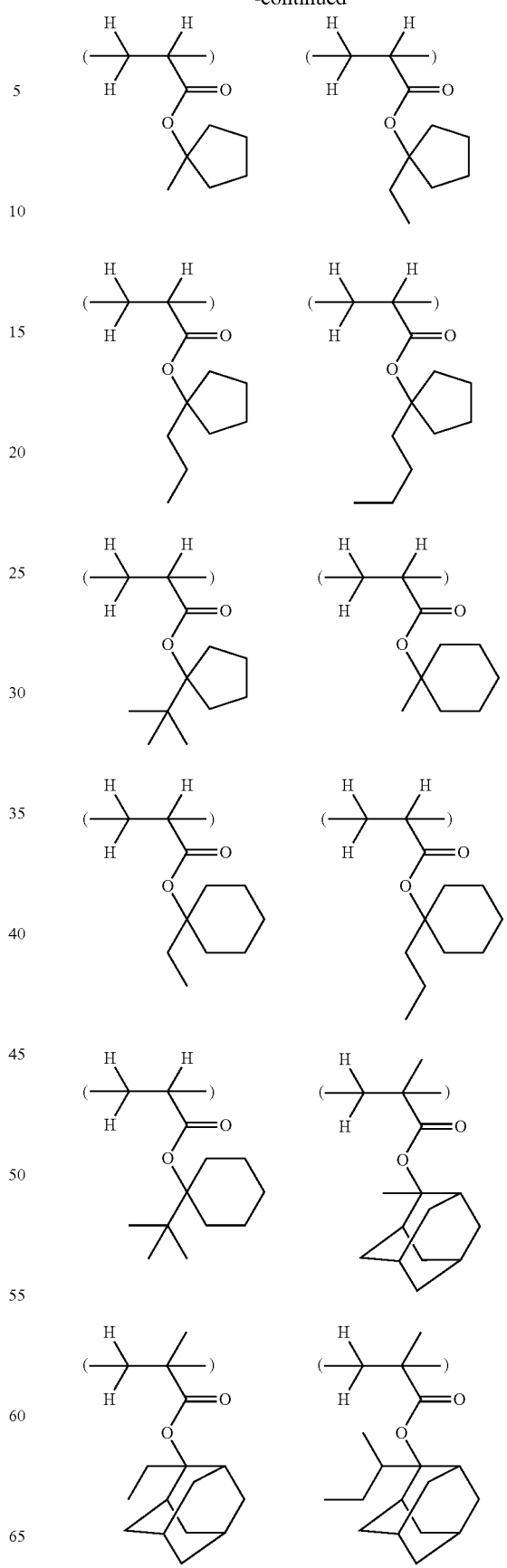

-continued
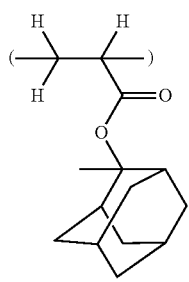 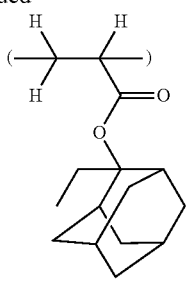 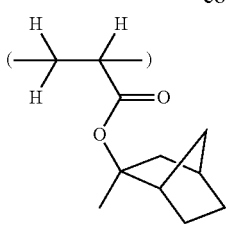 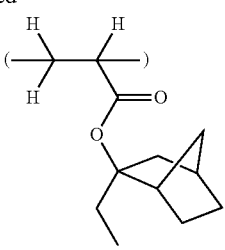
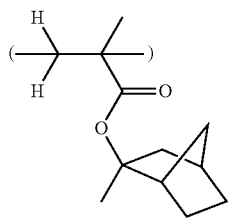 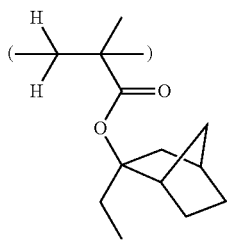 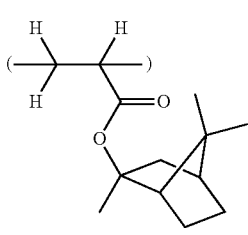 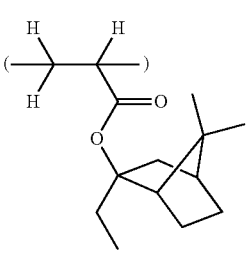
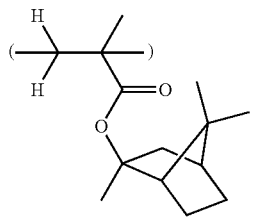 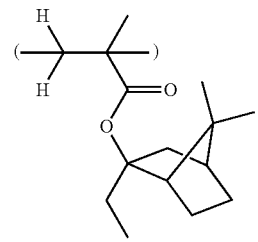 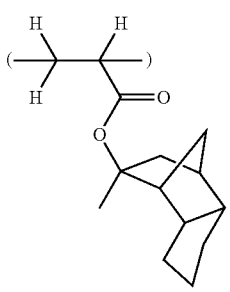 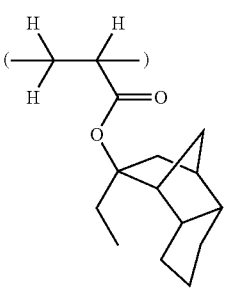
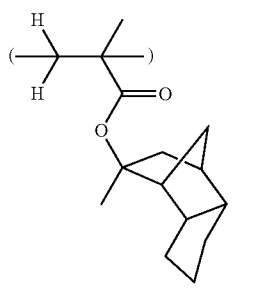 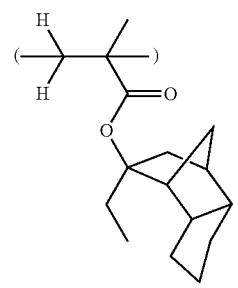 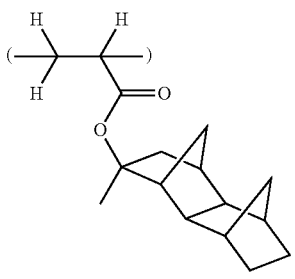
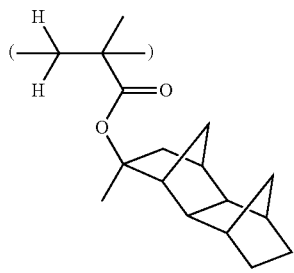 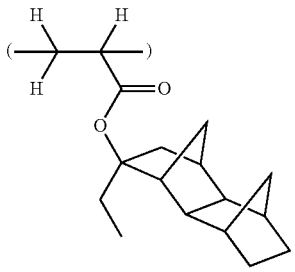
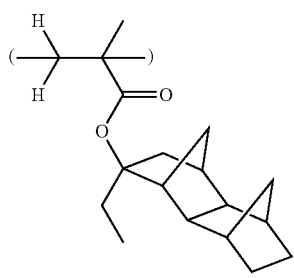 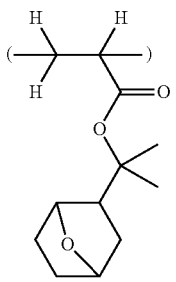 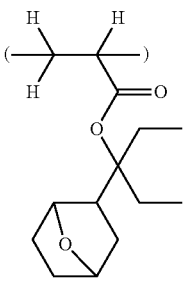

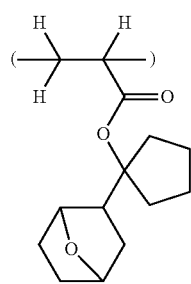 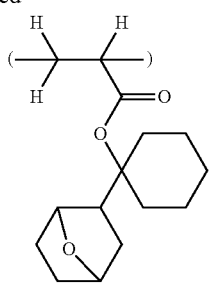 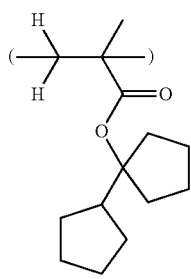 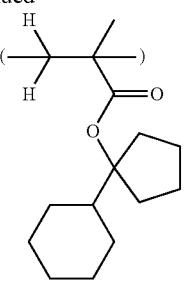
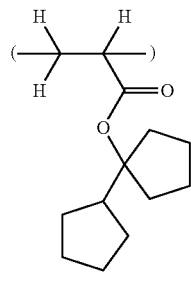 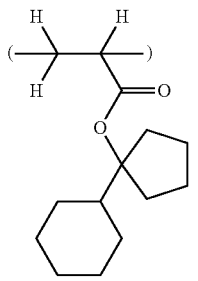 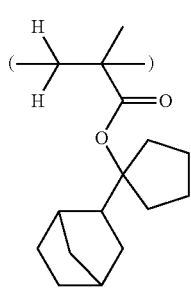 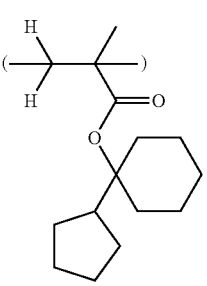
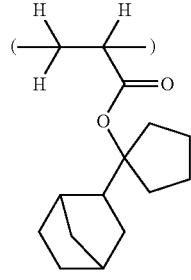 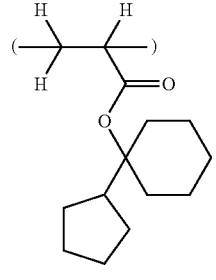 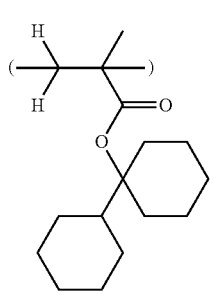 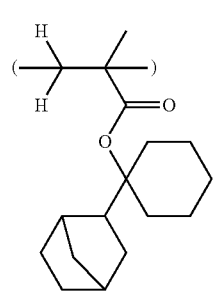
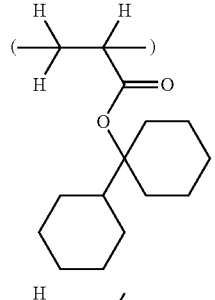 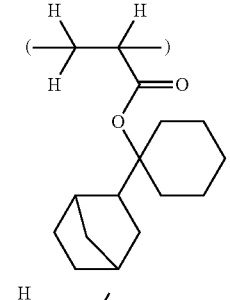 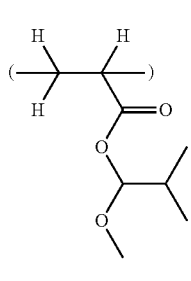 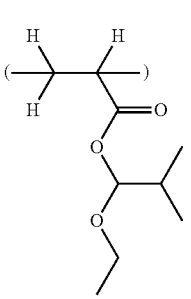
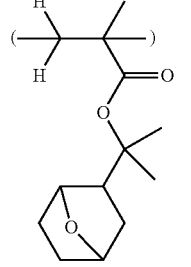 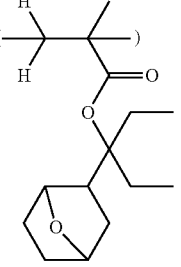 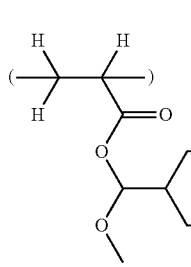 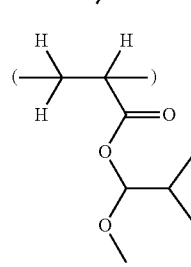
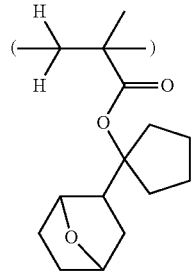 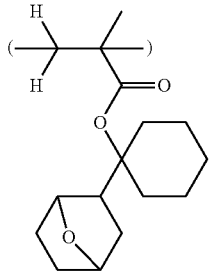 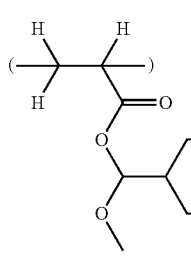 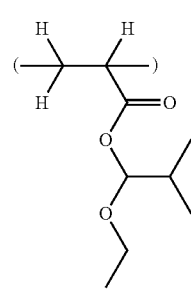

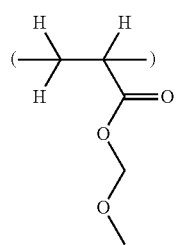 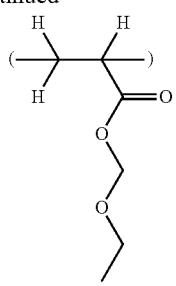 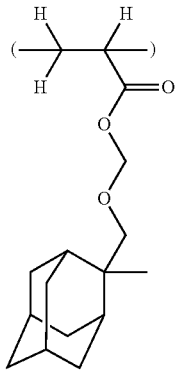 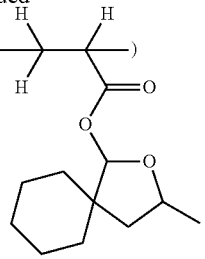 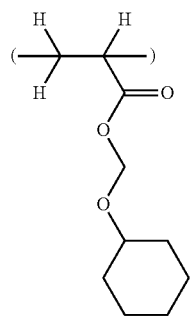 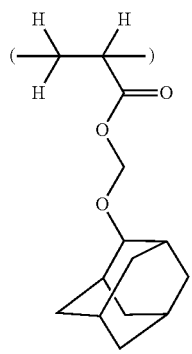 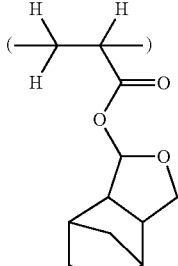 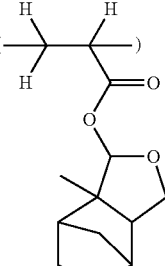 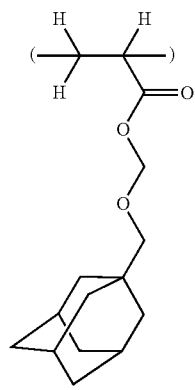 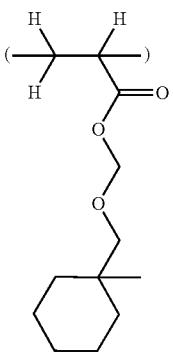 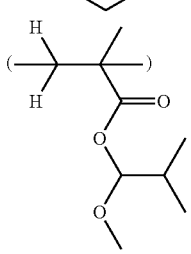 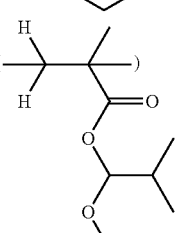 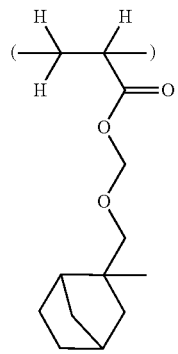 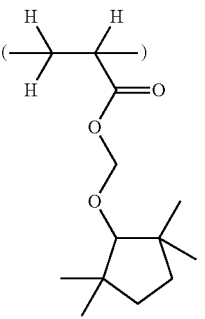 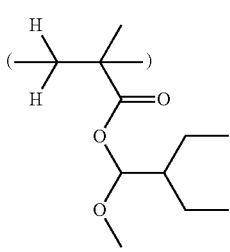 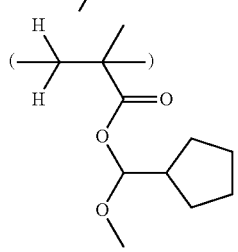 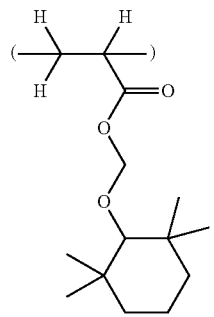 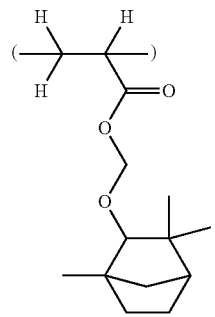 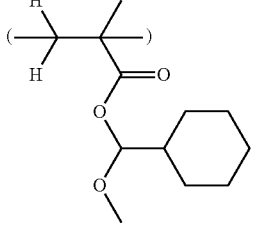 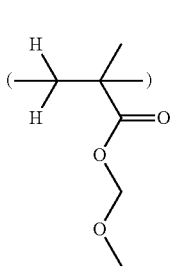

-continued

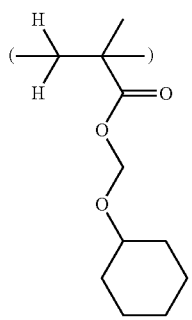 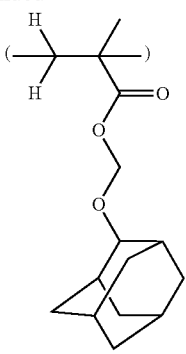

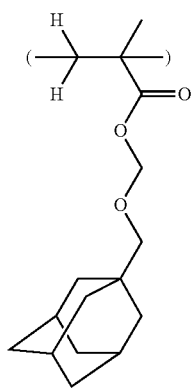 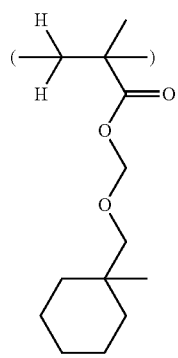

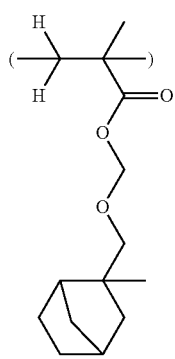 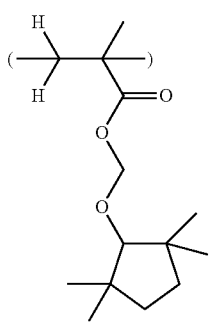

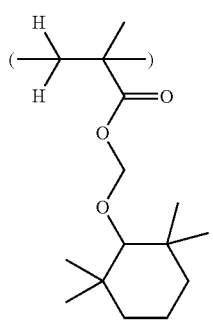 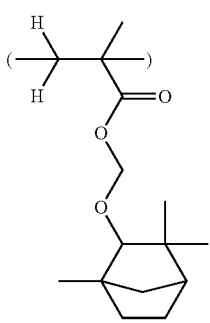

-continued

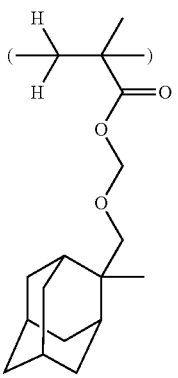 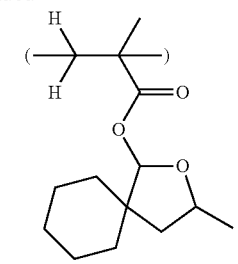

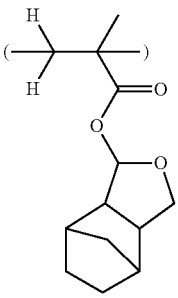 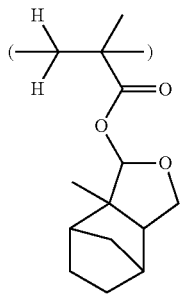

The above-mentioned specific examples are the case that Z is a single bond, but in the case that Z is other than the single bond, it may be combined with the same acid-labile group. There may be mentioned those in which Z is a single bond is replaced with that other than the single bond.

In the above-mentioned formula (3), YL represents a hydrogen atom, or a polar group having any one or a plural number of the structures selected from a hydroxyl group, a cyano group, a carbonyl group, a carboxyl group, an ether bond, an ester bond, a sulfonate ester bond, a carbonate bond, a lactone ring, a sultone ring and a carboxylic acid anhydride. More specifically, the following may be mentioned, but the YL is not limited to them.

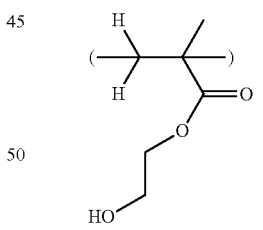 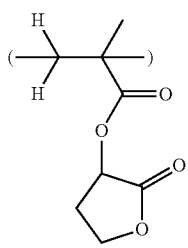

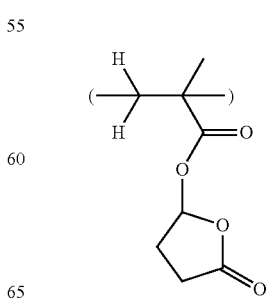 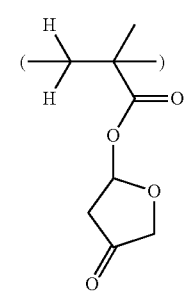

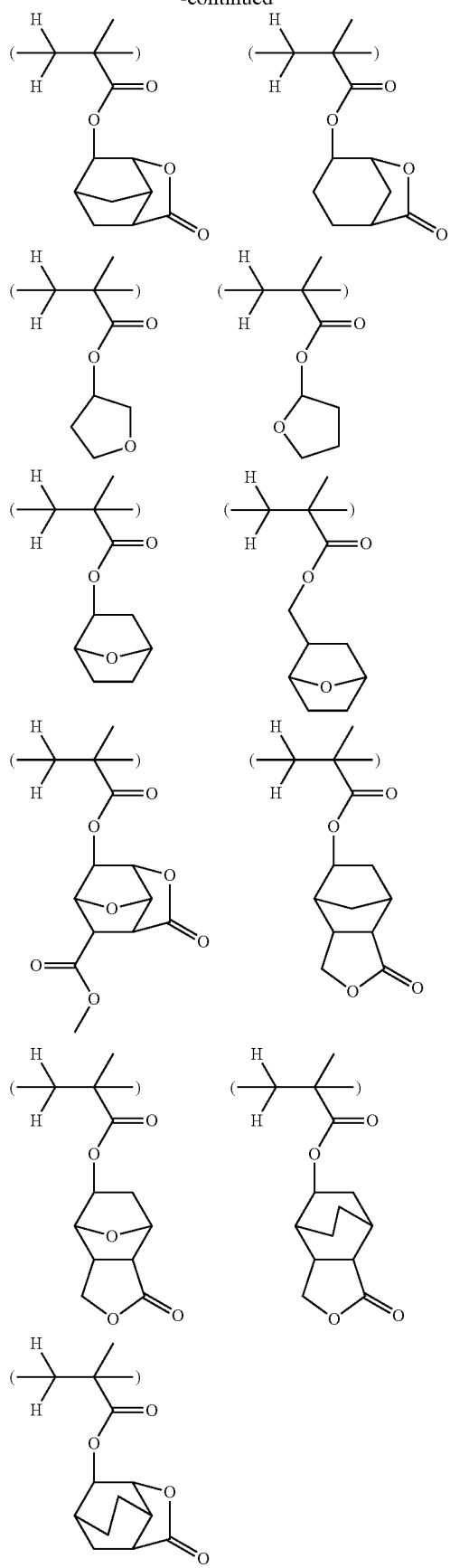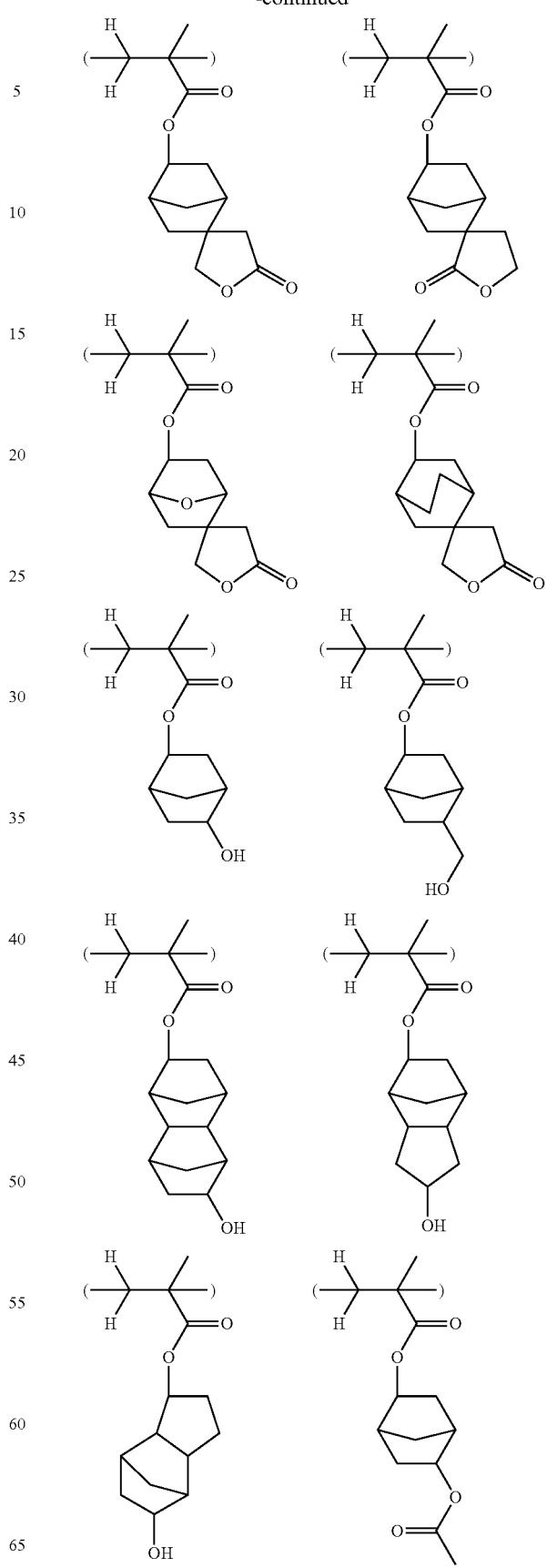

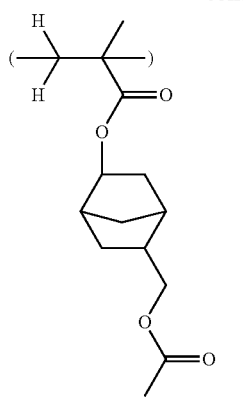
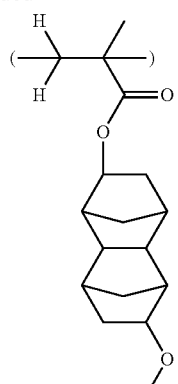
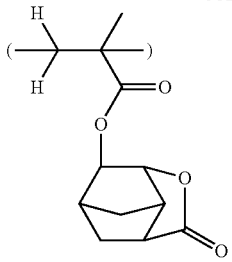
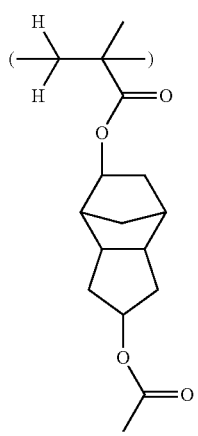
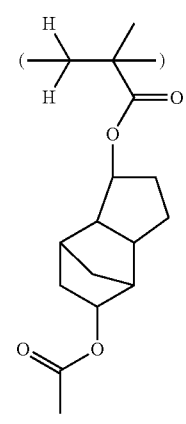
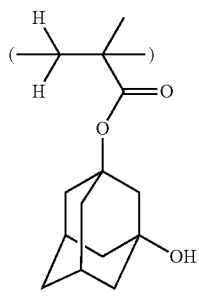
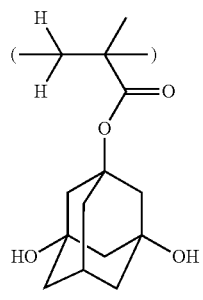
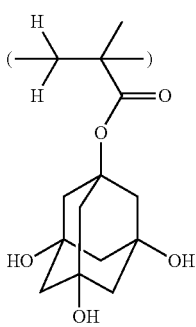
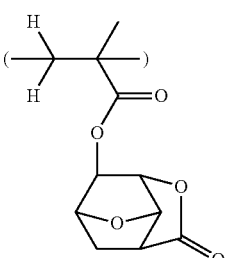
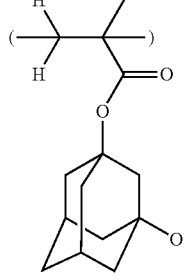
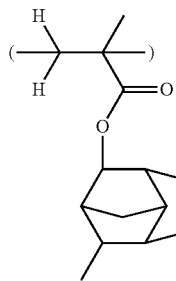
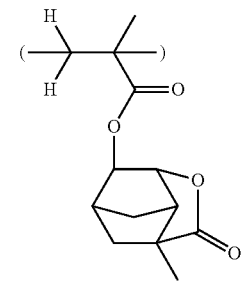
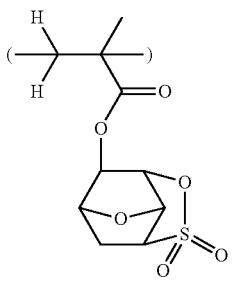
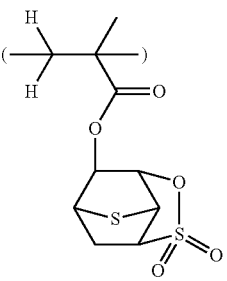

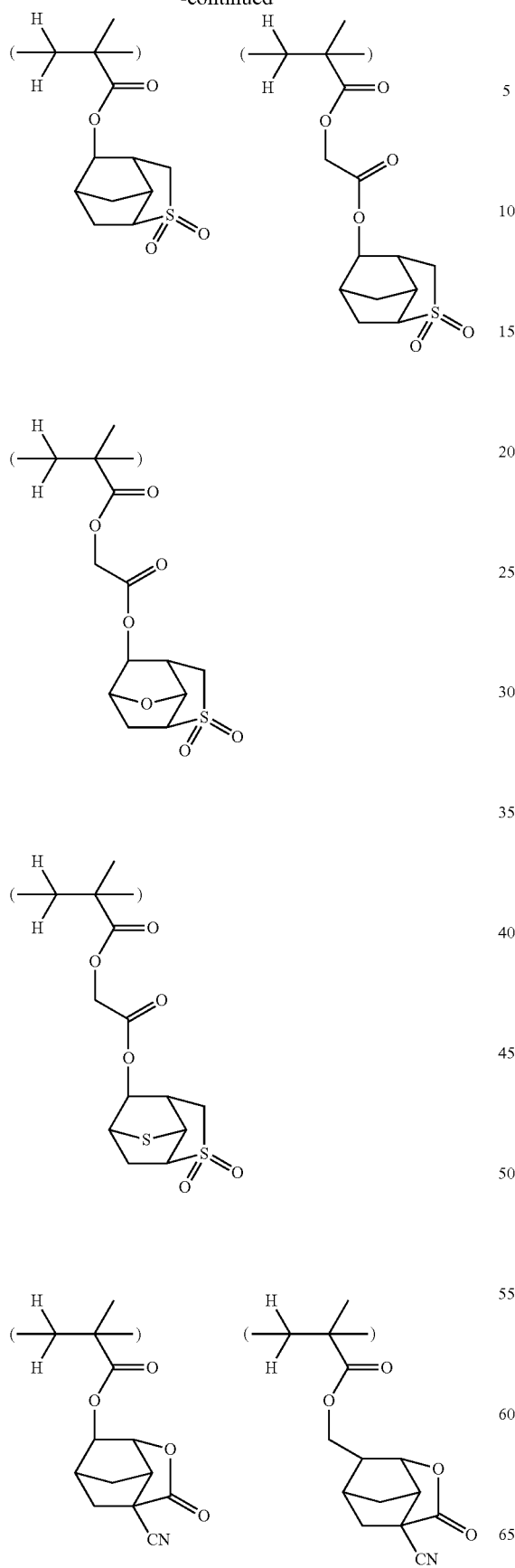
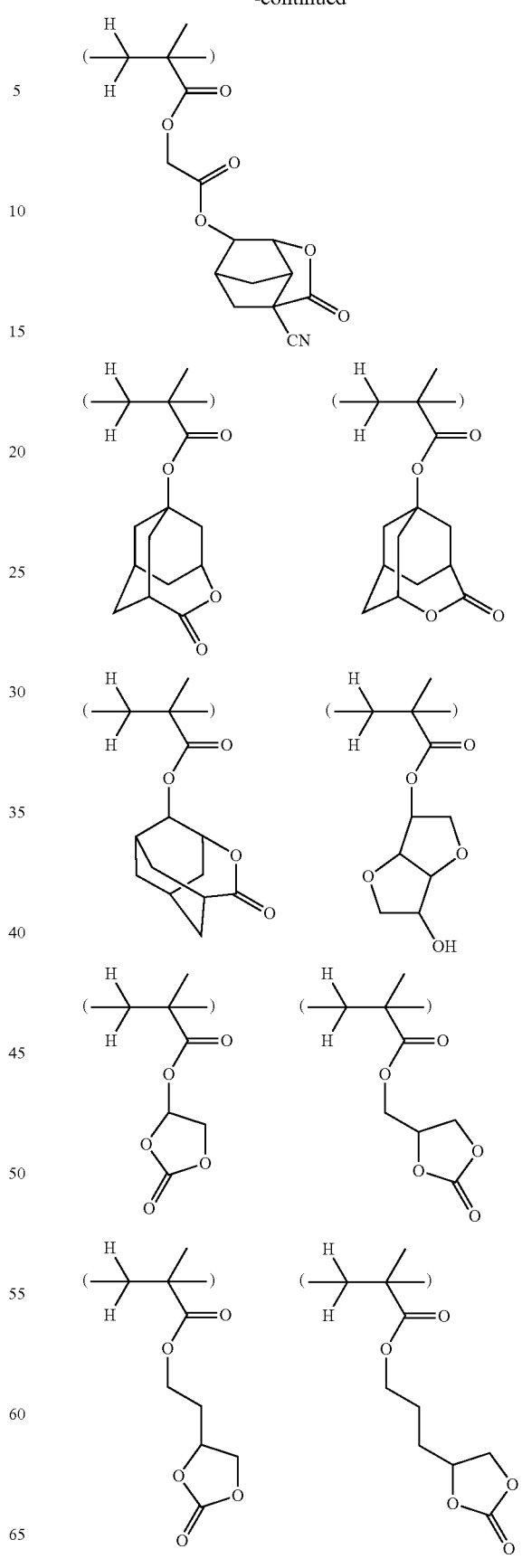

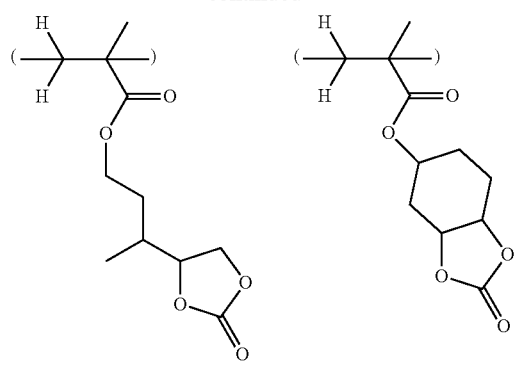
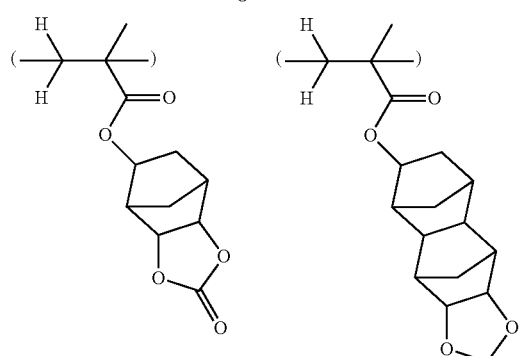
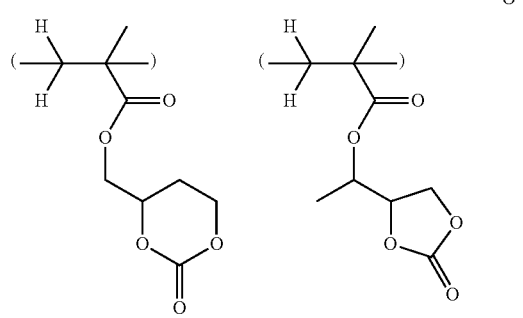
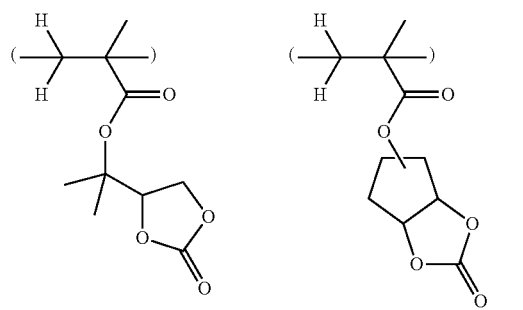
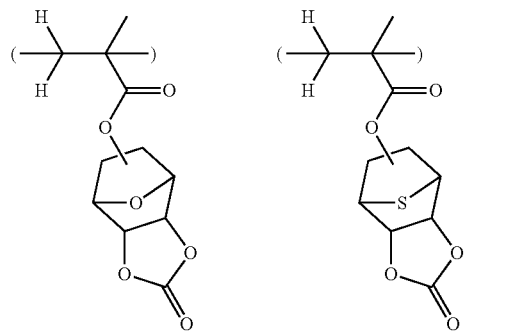
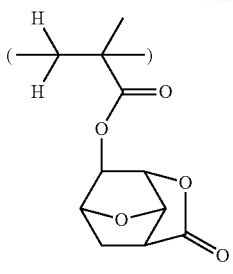
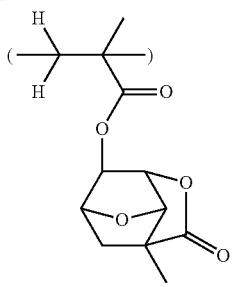
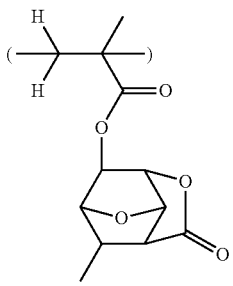
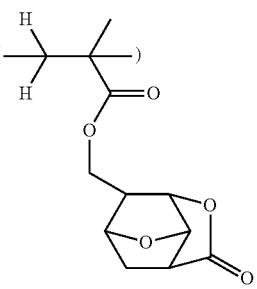
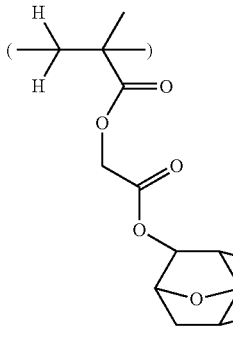
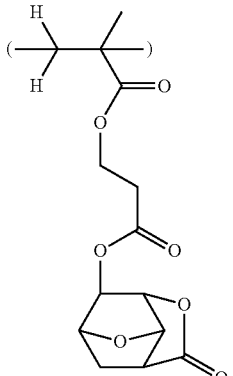
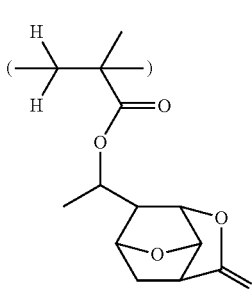

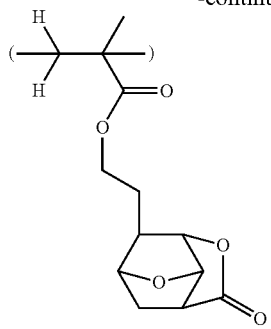
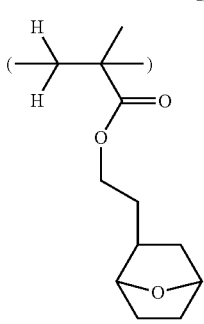
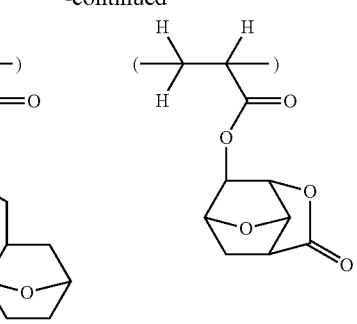
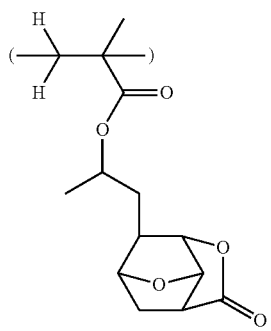
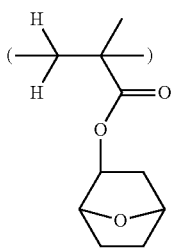
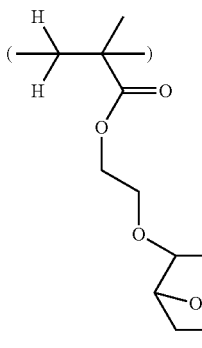
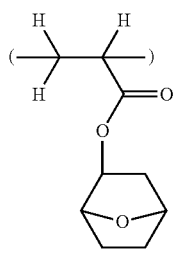
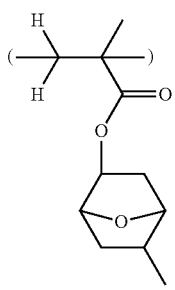
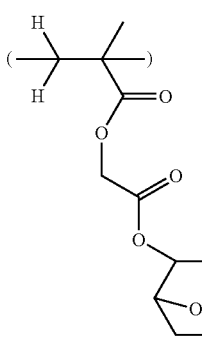
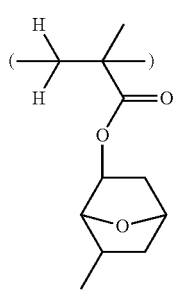
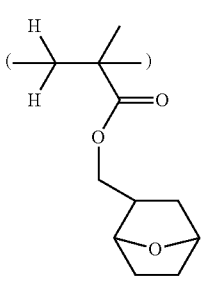
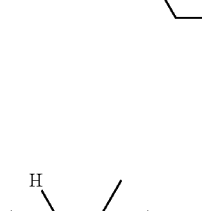
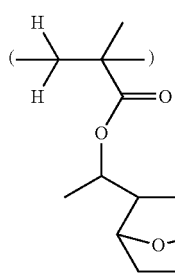
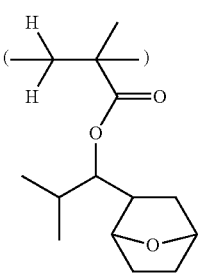
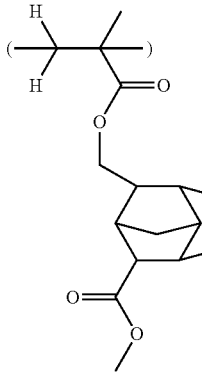
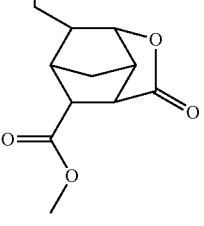

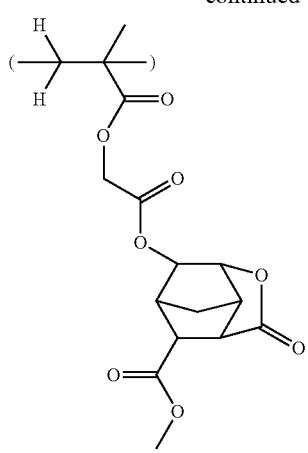
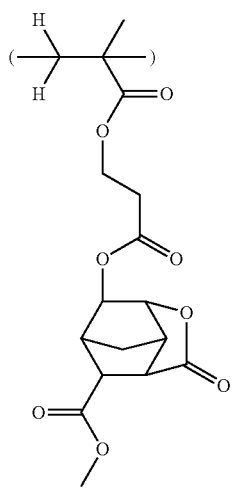
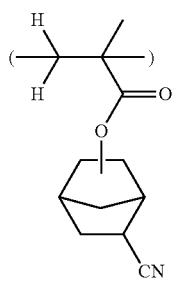
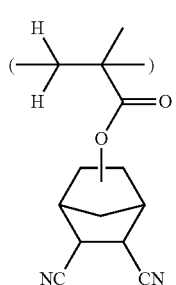
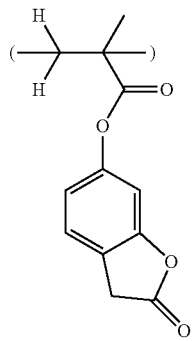
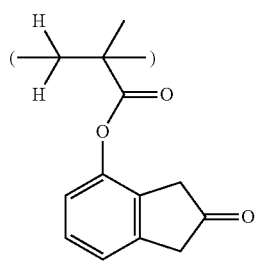
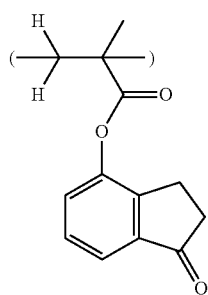
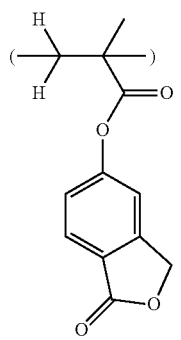
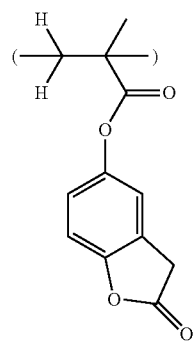
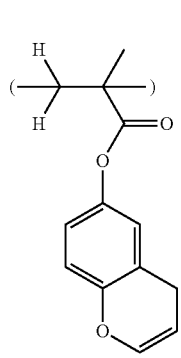
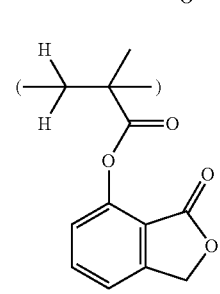
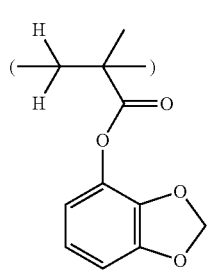
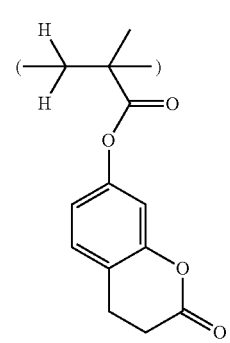

51
-continued
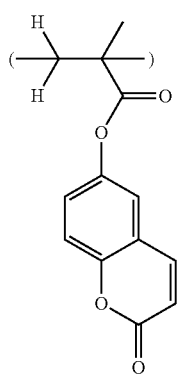 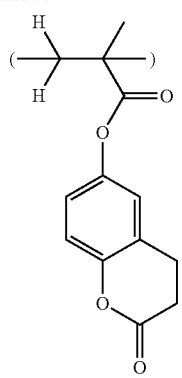
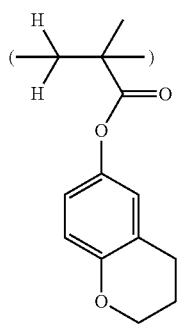 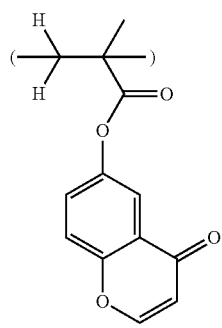
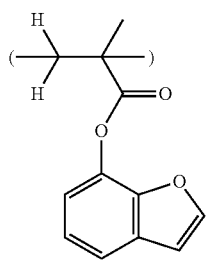 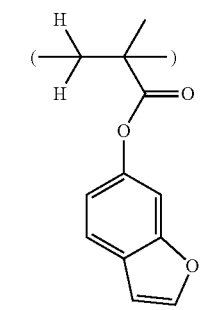
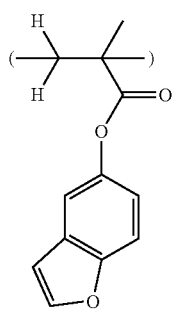 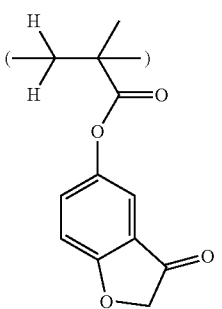
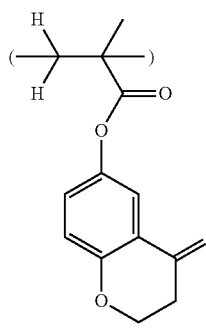 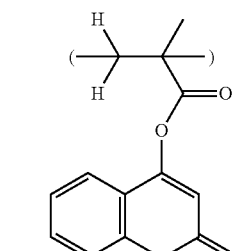
52
-continued
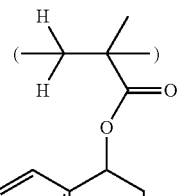 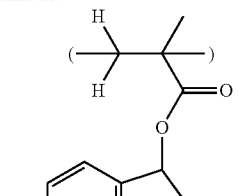
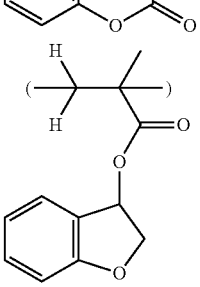 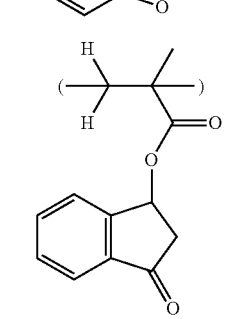
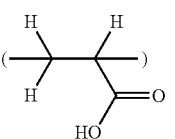 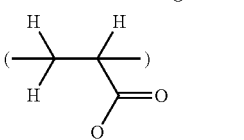
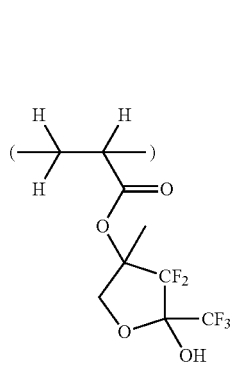 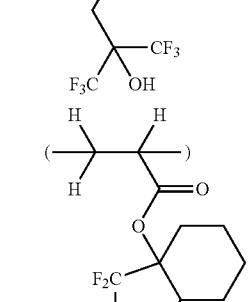
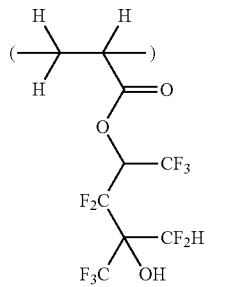 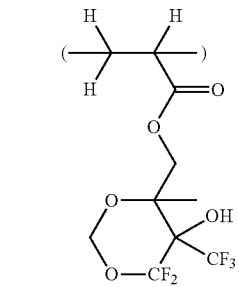
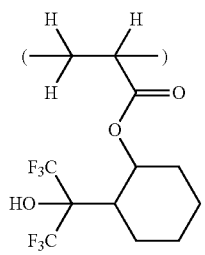 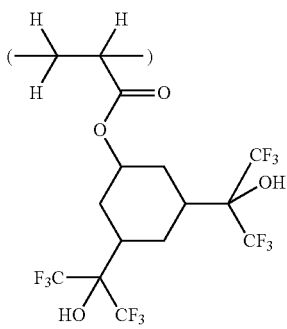

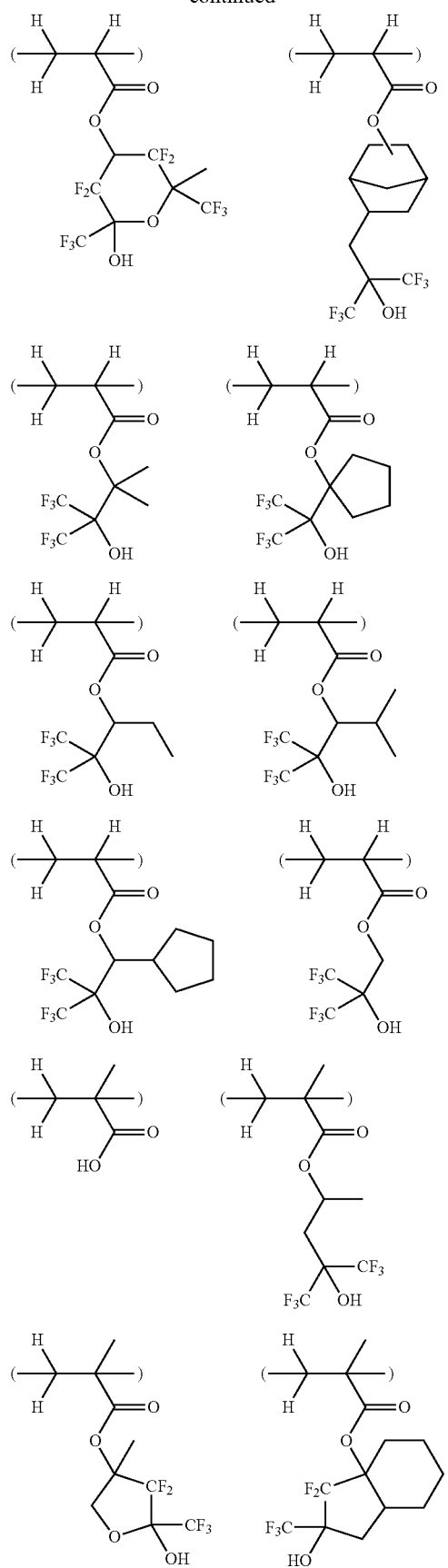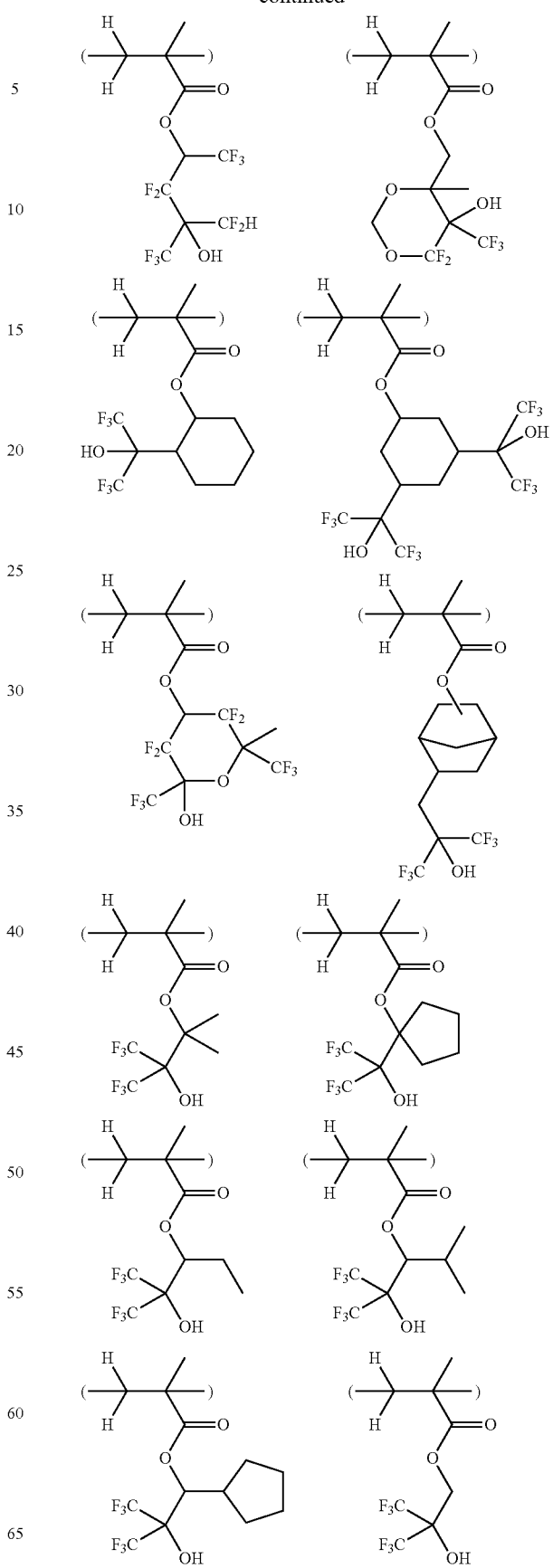

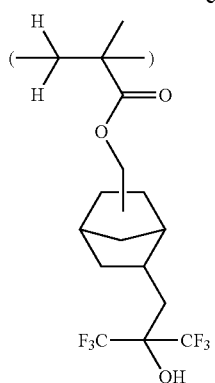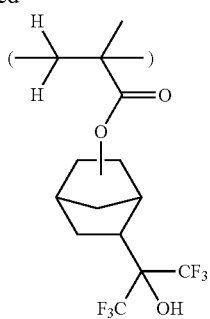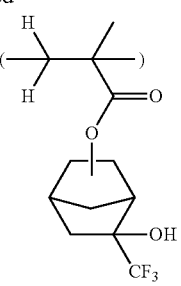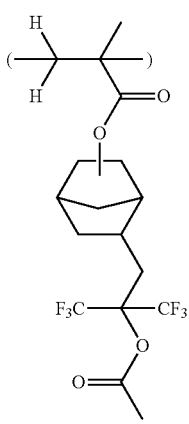
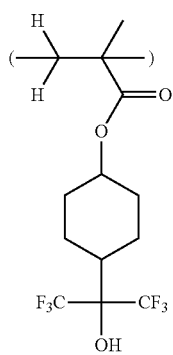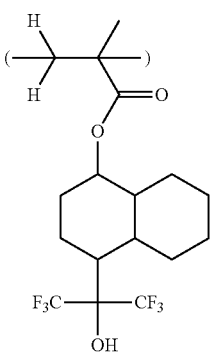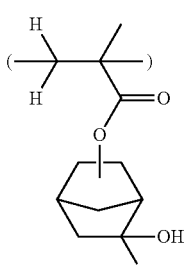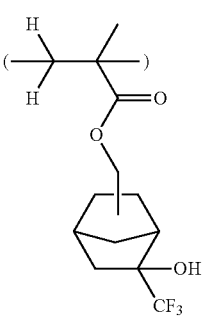
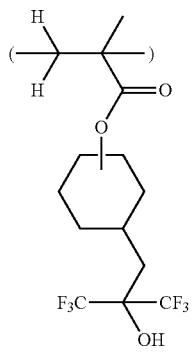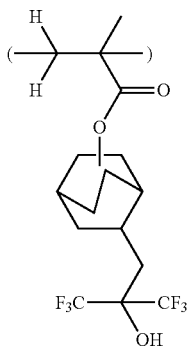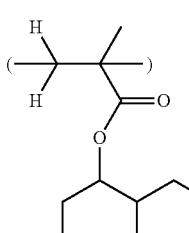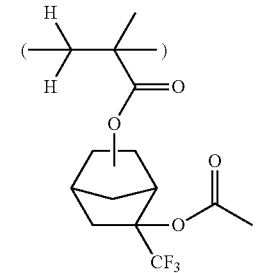
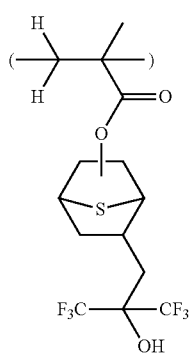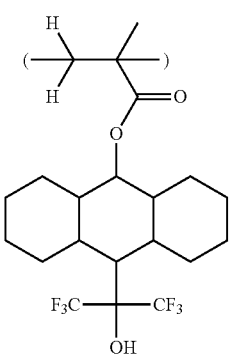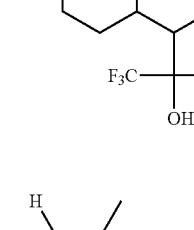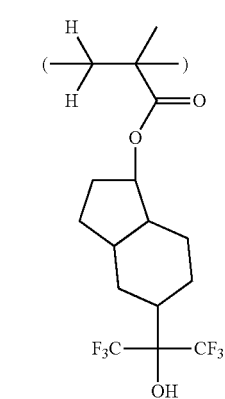
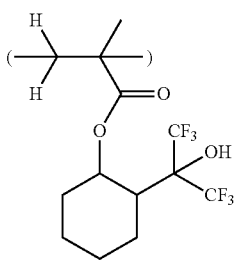

-continued
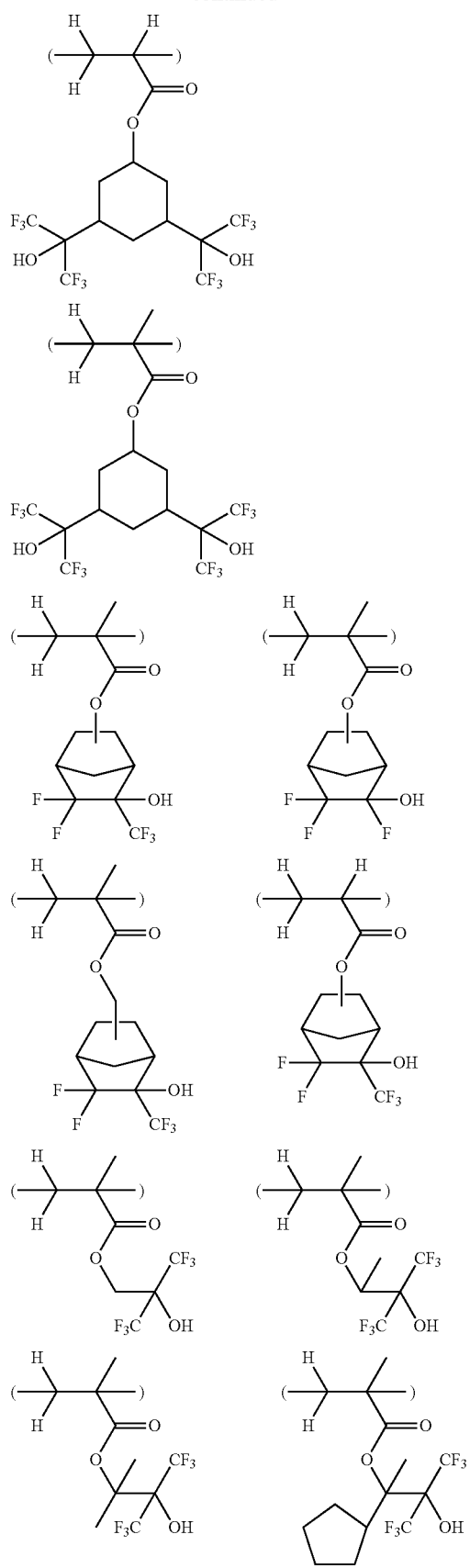
-continued
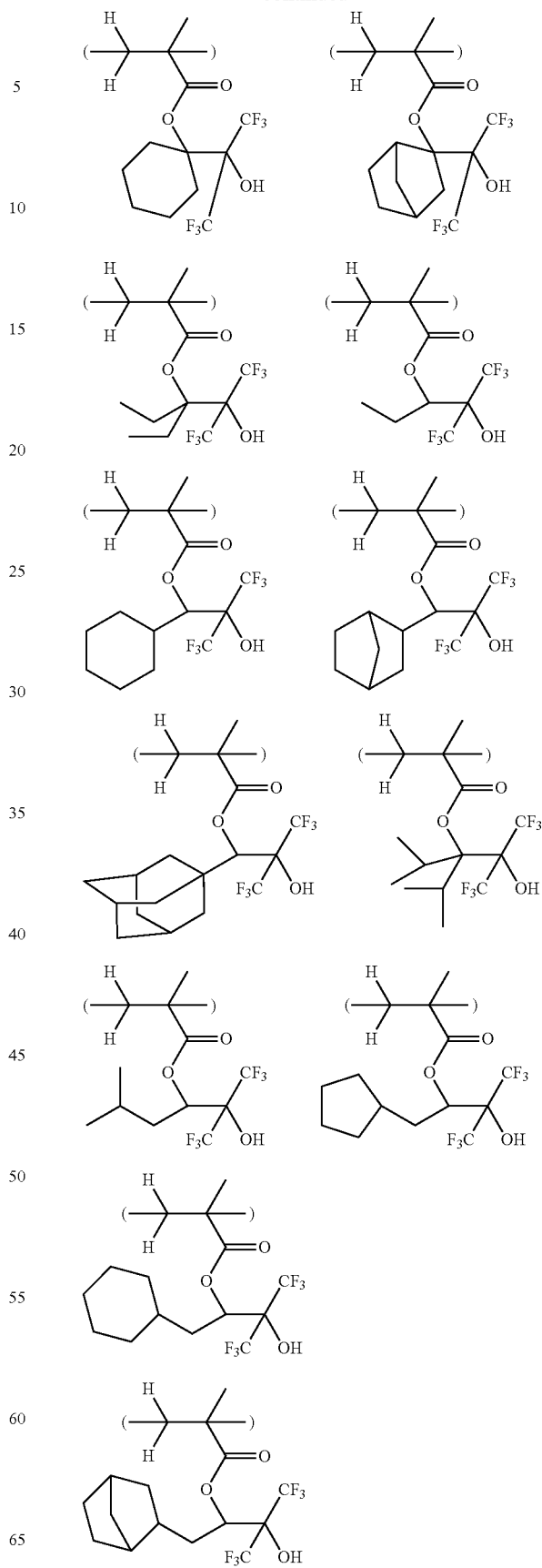

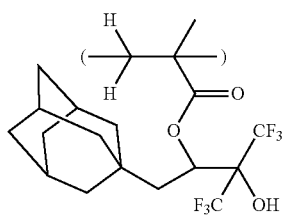
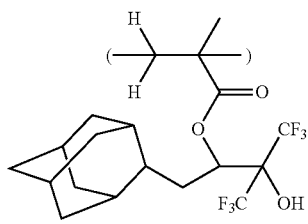
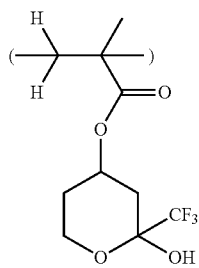 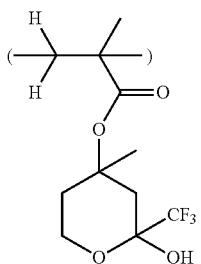
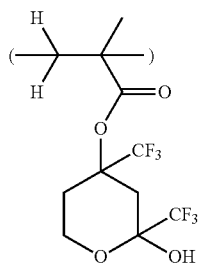 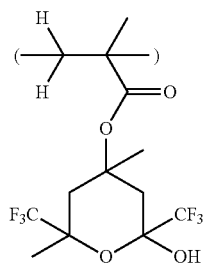
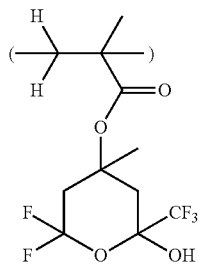 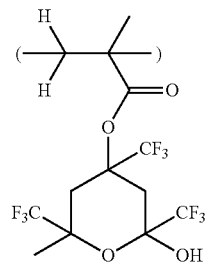
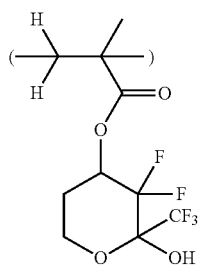 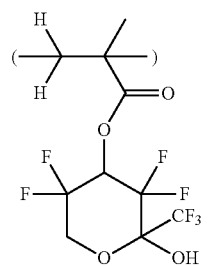
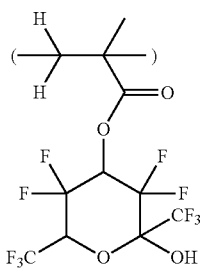 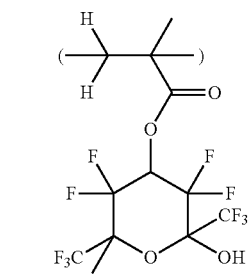
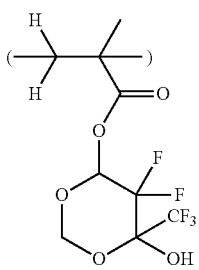 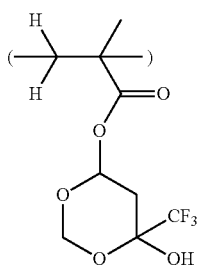
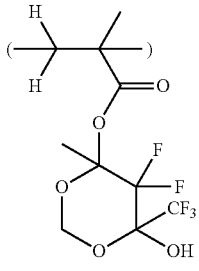 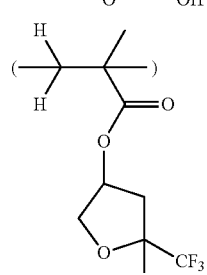
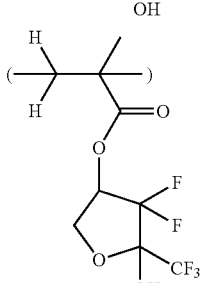 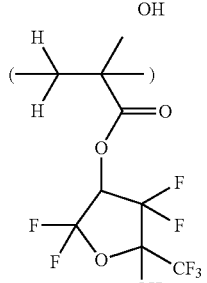
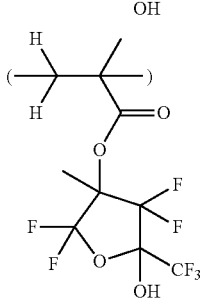 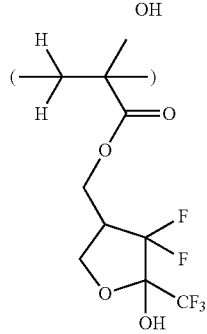

-continued
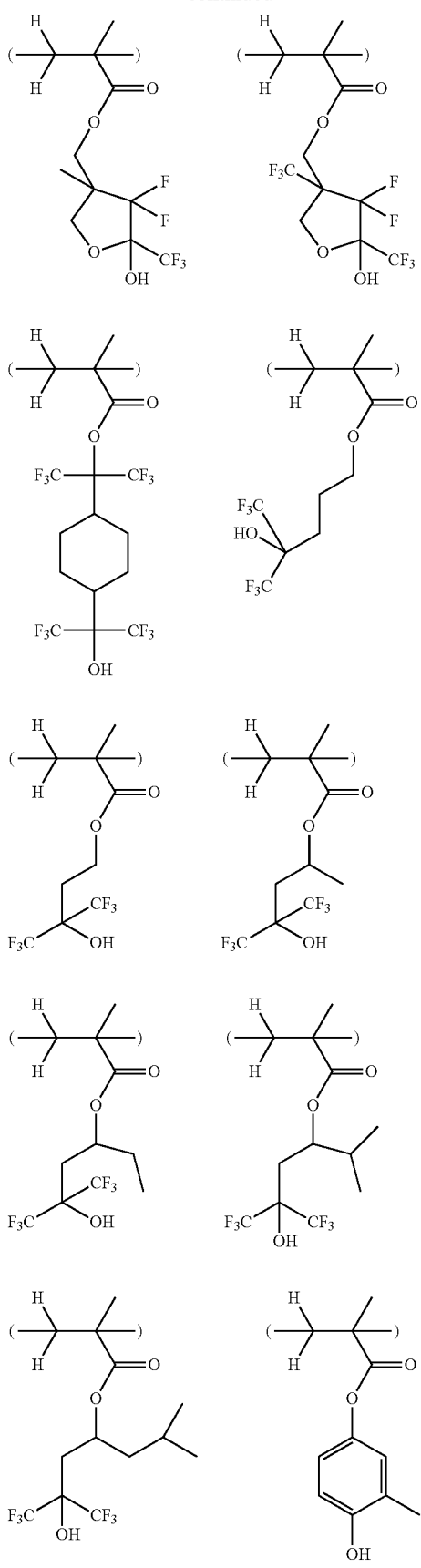
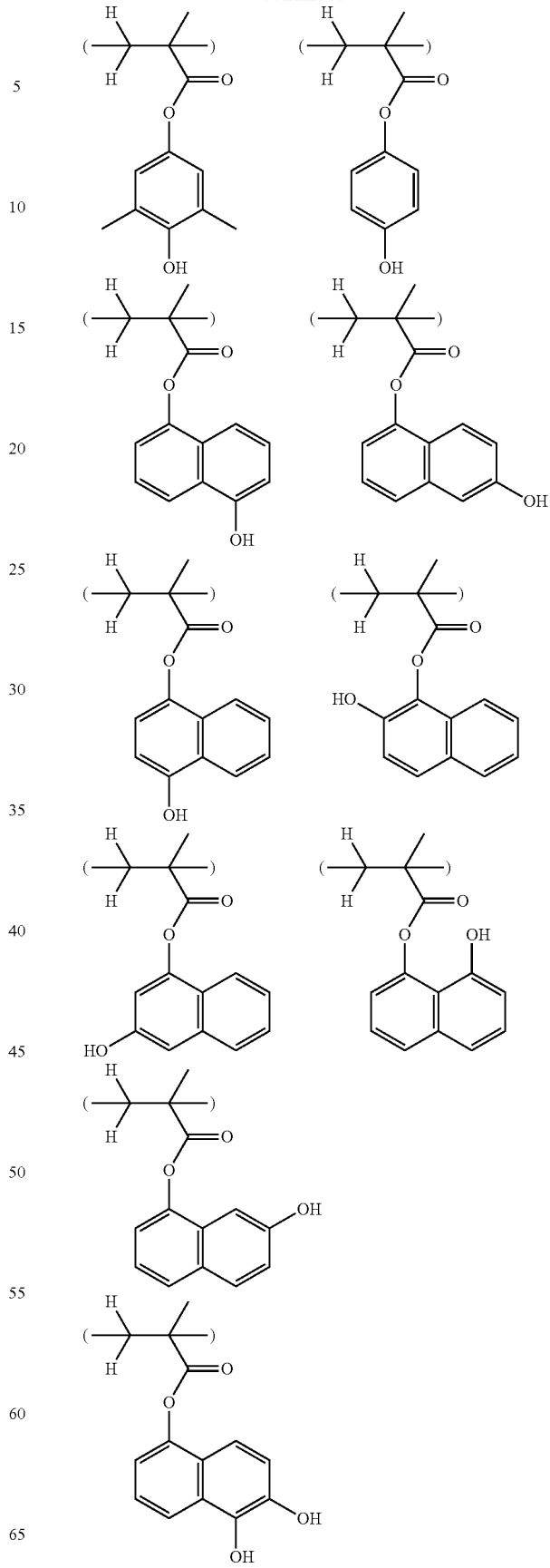

-continued

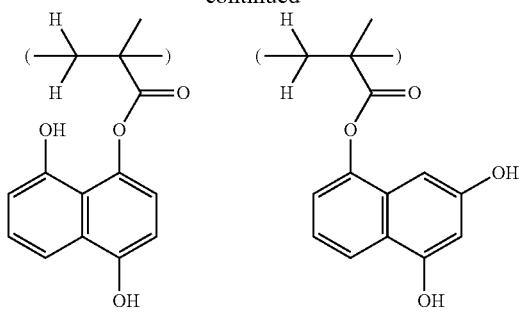

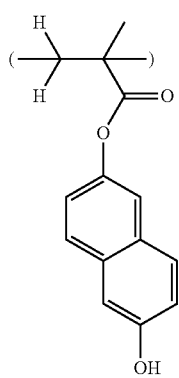

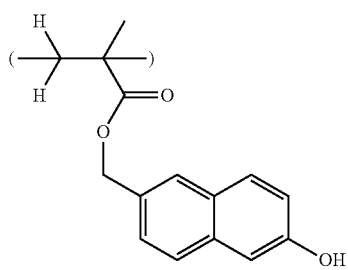

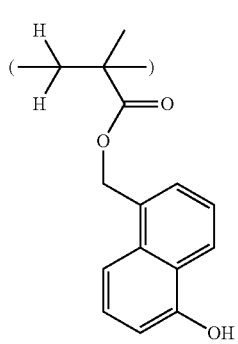

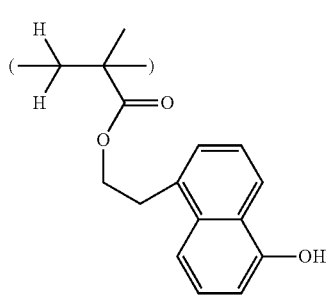

-continued

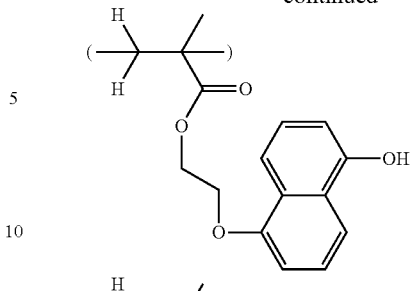

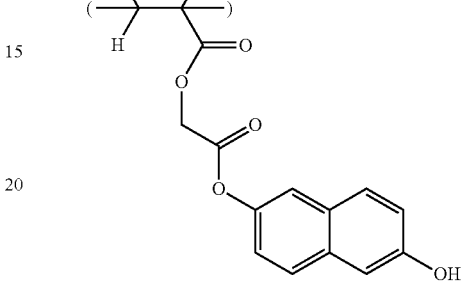

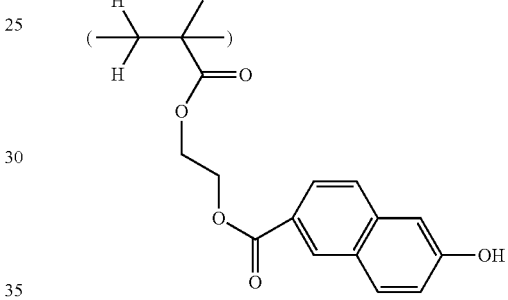

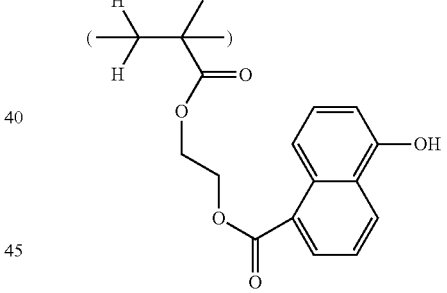

When the above-mentioned repeating unit represented by the general formula (3) is used, in particular, that having a lactone ring as a polar group is most preferably used.

The base resin to be used for the resist composition of the present invention is characterized by that it contains a repeating unit represented by the general formula (2) and a repeating unit represented by the general formula (3) already mentioned above, and other repeating units may be further copolymerized. For example, the base resin may contain repeating units including substituted acrylate esters such as methyl methacrylate, methyl crotonate, dimethyl maleate, dimethyl itaconate, etc., unsaturated carboxylic acids such as maleic acid, fumaric acid, itaconic acid, etc., cyclic olefins such as norbornene, norbornene derivative, tetracyclo[6.2.1.1$^{3,6}$.0$^{2,7}$]dodecene derivative, etc., unsaturated acid anhydrides such as itaconic anhydride, etc. The hydrogenated ring-opened metathesis polymer can be used those described in Japanese Patent Laid-Open Publication No. 2003-66612.

A weight-average molecular weight of the polymer compound to be used for the resist composition of the present invention is 1000 to 500000, preferably 3000 to 100000. If it is out of the above range, etching resistance is markedly lowered, or dissolution rate difference between before and after the exposure cannot be secured thereby deteriorating the resolution. The measurement method of the molecular weight may be mentioned gel permeation chromatography (GPC) which is shown in terms of the polystyrene converted value.

For synthesizing these polymer compounds, as one of the methods, there is a method in which one kind or several kinds of monomer having an unsaturated bond is polymerized under heating by adding a radical polymerization initiator in an organic solvent, and according to this method, a polymer compound can be obtained. The organic solvent to be used at the time of the polymerization may be exemplified by toluene, benzene, tetrahydrofuran, diethyl ether, dioxane, etc. The polymerization initiator may be exemplified by 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, etc., and polymerization can be carried out preferably heating to 50 to 80° C. The reaction time is generally 2 to 100 hours, preferably 5 to 20 hours. The acid-labile group introduced into a monomer may be used as it is, or may be protected or partially protected after polymerization.

In the polymer compound of Component (B) to be used in the resist composition of the present invention, the preferable ratio of the respective repeating units obtained from the respective monomers may be made, for example, set in the range (mol %) shown below, but not limited to this.

(I) one kind or two or more kinds of the structural units represented by the above-mentioned formula (2) are contained in an amount of 1 mol % or more and 50 mol % or less, preferably 5 to 40 mol %, more preferably 10 to 30 mol %, (II) one kind or two or more kinds of the structural units represented by the above-mentioned formula (3) are contained in an amount of 50 to 99 mol %, preferably 60 to 95 mol %, more preferably 70 to 90 mol %, and if necessary, (III) one kind or two or more kinds of the structural units based on the other monomers may be contained in an amount of 0 to 80 mol %, preferably 0 to 70 mol %, more preferably 0 to 50 mol %.

(C) Organic Solvent

The organic solvent of Component (C) to be used in the present invention may be any organic solvent so long as it can dissolve the polymer compound, the photo-sensitive acid generator, the quencher, and the other additives, etc. Such an organic solvent may be mentioned, for example, ketones such as cyclohexanone, methyl amyl ketone, etc., an alcohol such as 3-methoxybutanol, 3-methyl-3-methoxybutanol, 1-methoxy-2-propanol, 1-ethoxy-2-propanol, etc., ethers such as propylene glycol monomethyl ether, propylene glycol monoethyl ether, propylene glycol dimethyl ether, diethylene glycol dimethyl ether, etc., esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, etc., lactones such as γ-butyrolactone, etc., and may be used a single kind alone or two or more kinds in admixture, but not limited to them.

In the present invention, among these organic solvents, 1-ethoxy-2-propanol, propylene glycol monomethyl ether acetate, cyclohexanone, γ-butyrolactone, and a mixed solvent thereof are preferably used which are particularly excellent in solubility of the acid generator in the resist component.

An amount of the organic solvent to be used is suitably 200 to 5000 parts by mass, in particular 400 to 3000 parts by mass relative to 100 parts by mass of the base resin.

(D) Basic Compound (Quencher)

In the present specification, the basic compound (the quencher) means a compound which can suppress diffusion rate when an acid, etc., generated from the photo-sensitive acid generator is diffused into a resist film. Such a quencher suitably used may be mentioned primary, secondary or tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, alcoholic nitrogen-containing compounds, amides, imides, carbamates, ammonium salts, etc.

In this case, a compound having a high nucleophilicity and a compound having a too strong basicity are not suitable since it can be reacted with the cation portion of the sulfonium salt of the present invention. There may be preferably mentioned a compound in which a primary or secondary amine is protected by tBOC (tert-butoxycarbonyl). These protected amines may be referred to, for example, Japanese Patent Laid-Open Publication No. 2007-298569, No. 2010-20204, etc. Also, anilines, for example, an aniline series compound such as aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine, etc., are weakly basic, and they are suitable in a combination with the sulfonium salt of the present invention.

Meanwhile, these quenchers may be used a kind alone or two or more kinds in combination, and a blending amount thereof is preferably 0.001 to 12 parts, particularly 0.01 to 8 parts relative to 100 parts of the base resin. By blending the quencher, not only adjustment of the resist sensitivity becomes easy, but also diffusion rate of the acid in the resist film is suppressed to improve resolution, change in sensitivity after exposure is suppressed, dependency on a substrate or an environment can be lowered, and exposure margin and a pattern profile, etc., can be improved. Also, by adding these quenchers, substrate adhesiveness can be also improved.

(E) Surfactant Insoluble or Difficultly Soluble in Water and Soluble in Alkaline Developing Solution, and/or Surfactant Insoluble or Difficultly Soluble in Water and Alkaline Developing Solution (Hydrophobic Resin)

In the resist composition of the present invention, Component (E) of a surfactant may be added, and can be referred to the component defined in (S) described in Japanese Patent Laid-Open Publication No. 2010-215608 or No. 2011-16746.

As to the surfactant insoluble or difficultly soluble in water and an alkaline developing solution, among the surfactants described in the above patent documents, FC-4430, Surflon S-381, Surfynol E1004, KH-20, KH-30, and oxetane ring-opened polymers represented by the following structural formula (surf-1) are preferable. These may be used alone or in combination of two or more.

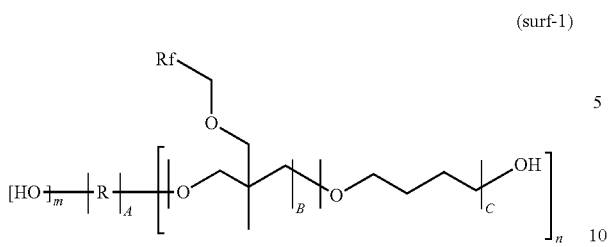

(surf-1)

Here, R, Rf, A, B, C, m and n are applied only to the above-mentioned formula (surf-1) irrespective of the above-mentioned descriptions. R represents a 2- to 4-valent aliphatic group having 2 to 5 carbon atoms, and specifically ethylene, 1,4-butylene, 1,2-propylene, 2,2-dimethyl-1,3-propylene, and 1,5-pentylene may be mentioned as the divalent group, and the 3-valent or 4-valent group may be mentioned the followings.

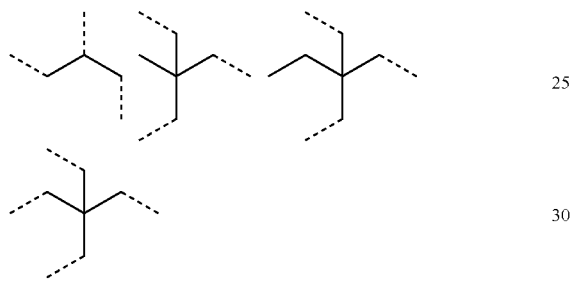

wherein the dotted line represents a bonding arm, and these are partial structures derived from glycerol, trimethylolethane, trimethylolpropane, and pentaerythritol, respectively.

Among these, preferably used is 1,4-butylene or 2,2-dimethyl-1,3-propylene. Rf represents a trifluoromethyl group or a pentafluoroethyl group, preferably a trifluoromethyl group. m is an integer of 0 to 3, n is an integer of 1 to 4, the sum of n and m represents a number of valence of R, and is an integer of 2 to 4. A is 1, B is an integer of 2 to 25, C is an integer of 0 to 10. B is preferably an integer of 4 to 20, and C is preferably 0 or 1. The above structure does not specify the arrangement of the respective constitutional units while they may be bonded as a block or randomly. Production of the surfactant with the type of a partially fluorinated oxetane ring-opened polymer, is described in detail in U.S. Pat. No. 5,650,483, etc.

The surfactant insoluble or difficultly soluble in water and soluble in an alkaline developing solution has a function of reducing penetration or leaching of water by orientating at the surface of the resist after spin coating when resist protective coat is not used in the ArF immersion exposure. Thus, it is useful for lowering damage of the exposure device by suppressing elution of the water-soluble component from the resist film, and after the exposure, it is also useful since it solubilizes at the time of an alkaline development after post baking whereby it difficultly becomes foreign matters which causes defects. This surfactant has a property that is insoluble or difficultly soluble in water and soluble in an alkaline developing solution, which is also called as a hydrophobic resin, and particularly, those having a high water-repellency and improve water sliding property are preferable. Such a polymer type surfactant can be shown as follows:

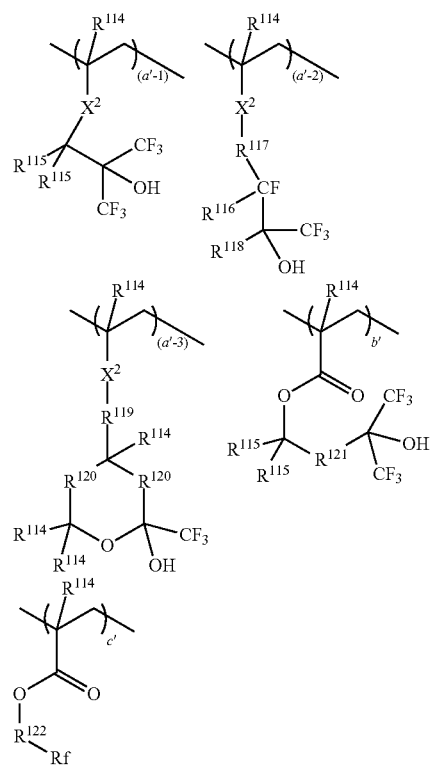

wherein each of $R^{114}$ may be the same or different, and represent a hydrogen atom, a fluorine atom, a methyl group, or a trifluoromethyl group; each of $R^{115}$s may be the same or different, and represent a hydrogen atom, or a linear, branched, or cyclic alkyl group or a fluorinated alkyl group each having 1 to 20 carbon atoms, wherein each of $R^{115}$ in the same monomer may be bonded to form a ring with the carbon atoms to which they are bonded, and in such a case, it represents a linear, branched, or cyclic alkylene group or a fluorinated alkylene group having 2 to 20 carbon atoms in total; $R^{116}$ represents a fluorine atom or a hydrogen atom, or may be bonded with $R^{117}$ to form a non-aromatic ring having, as total, 3 to 10 carbon atoms together with the carbon atoms to which they are bonded; $R^{117}$ represents a linear, branched, or cyclic alkylene group having 1 to 6 carbon atoms, wherein one or more hydrogen atoms may be substituted by a fluorine atom; $R^{118}$ represents a linear or branched alkyl group having 1 to 10 carbon atoms, wherein one or more hydrogen atoms thereof are substituted by a fluorine atom, and $R^{117}$ and $R^{118}$ may be bonded to form a non-aromatic ring together with the carbon atoms to which they are bonded, and in such a case, representing a trivalent organic group as total of $R^{117}$, $R^{118}$, and the carbon atoms to which they are bonded having 2 to 12 carbon atoms; $R^{119}$ represents a single bond or an alkylene group having 1 to 4 carbon atoms; each of $R^{120}$ may be the same or different, and represent a single bond, —O—, or —$CR^{114}R^{114}$—; $R^{121}$ represents a linear or branched alkylene group having 1 to 4 carbon atoms, and may be bonded with $R^{115}$ in the same monomer to form a non-aromatic ring having 3 to 6 carbon atoms together with the carbon atoms to which they are bonded; $R^{122}$ represents a 1,2-ethylene group, a 1,3-propylene group, or a 1,4-butylene group;

Rf represents a linear perfluoroalkyl group having 3 to 6 carbon atoms, or a 3H-perfluoropropyl group, a 4H-perfluorobutyl group, a 5H-perfluoropentyl group or a 6H-perfluorohexyl group; each of $X^2$ may be the same or different, and represents —C(=O)—O—, —O— or —C(=O)—R$^{123}$—C(=O)—O—, and R$^{123}$ represents a linear, branched, or cyclic alkylene group having 1 to 10 carbon atoms. Furthermore, $0 \leq (a'-1) < 1$, $0 \leq (a'-2) < 1$, $0 \leq (a'-3) < 1$, $0 < (a'-1)+(a'-2)+(a'-3) < 1$, $0 \leq b' < 1$, $0 \leq c' < 1$, and $0 < (a'-1)+(a'-2)+(a'-3)+b'+c' \leq 1$.

The above units are more specifically shown below.

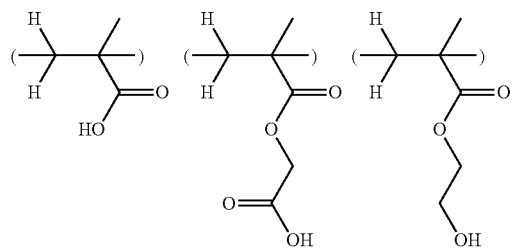
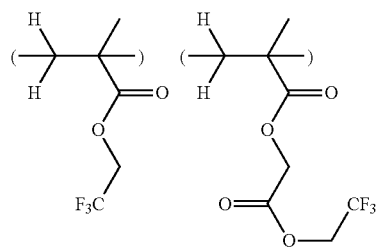
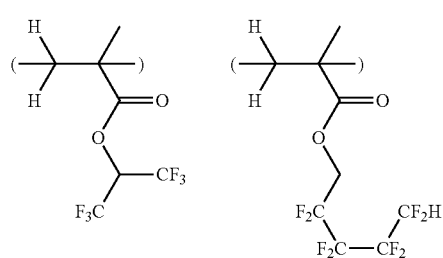
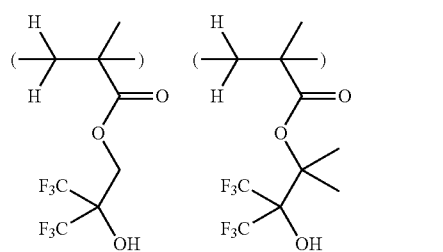
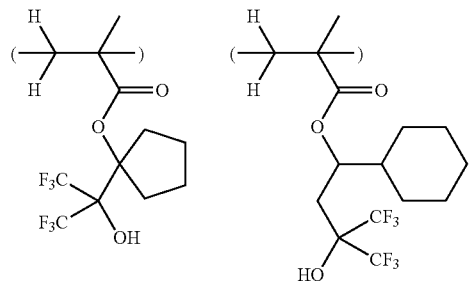

-continued

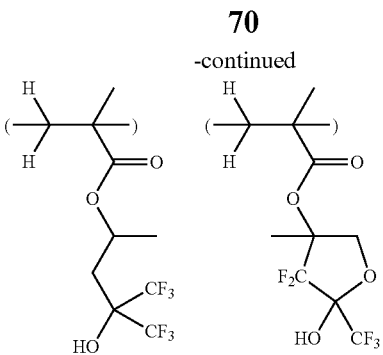
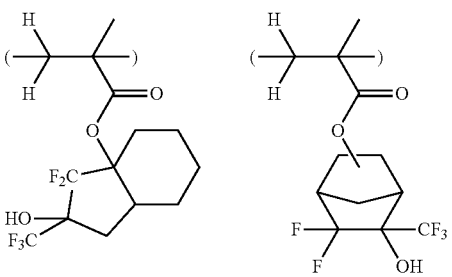
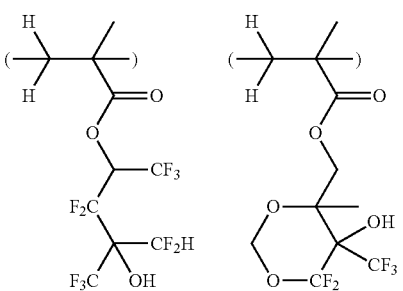
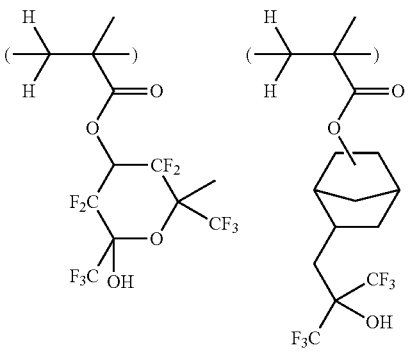
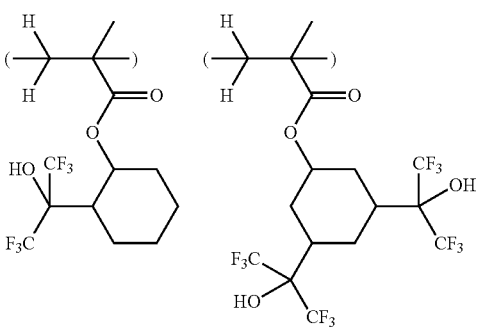

-continued

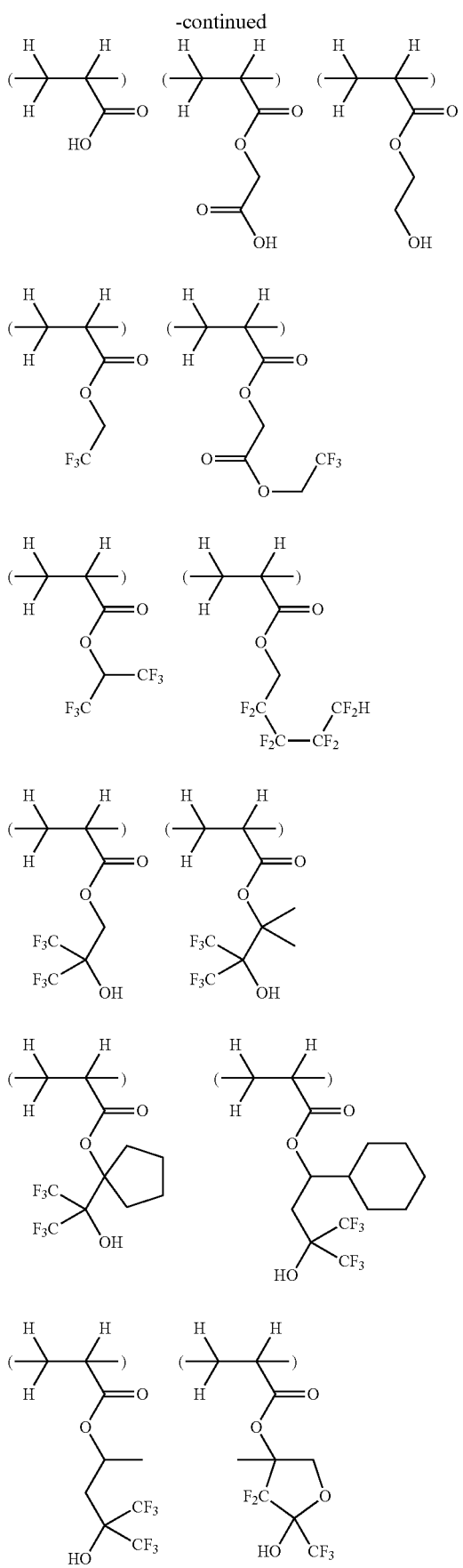
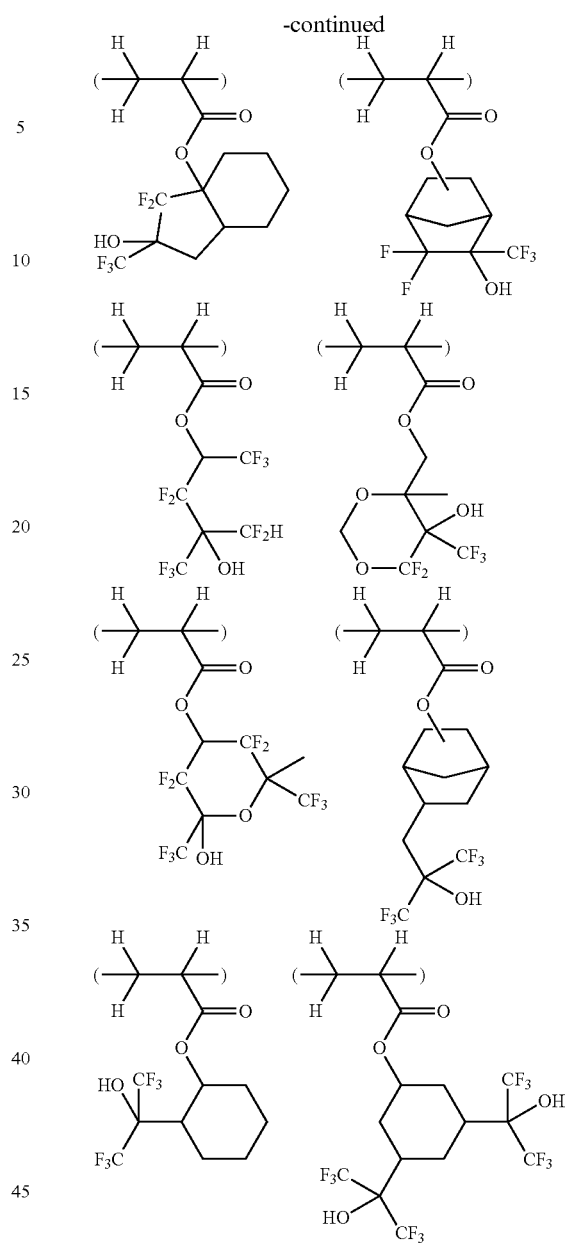

These surfactants insoluble or difficultly soluble in water and soluble in an alkaline developing solution may also be referred to Japanese Patent Laid-Open Publication No. 2008-122932, No. 2010-134012, No. 2010-107695, No. 2009-276363, No. 2009-192784, No. 2009-191151, No. 2009-98638, No. 2010-250105, and No. 2011-42789.

A weight-average molecular weight of the above-mentioned polymer type surfactant is preferably 1000 to 50000, more preferably 2000 to 20000. If it is out of the above range, a surface modification effect is not sufficient, or development failure occurs in some cases. Meanwhile, the weight-average molecular weight is shown by the polystyrene converted value measured by gel permeation chromatography (GPC). The addition amount thereof is in the range of 0.001 to 20 parts by mass, preferably 0.01 to 10 parts by mass relative to 100 parts by mass of the base resin of resist composition. These are described in detail in Japanese Patent Laid-Open Publication No. 2010-215608.

(F) Photo-Sensitive Acid Generator Other than the Sulfonium Salt (Photo-Sensitive Acid Generator) Represented by the General Formula (1a) or (1b)

When the photo-sensitive acid generator (F) is added, any compound may be used so long as it is a compound generating an acid by the irradiation of high energy beam such as ultraviolet ray, far ultraviolet ray, electron beam, EUV, X-rays, excimer laser, γ-rays, synchrotron radiation beam, etc. Preferable photo-sensitive acid generator may be mentioned a photo-sensitive acid generator such as a sulfonium salt, an iodonium salt, sulfonyldiazomethane, N-sulfonyloxydicarboxylmide, O-arylsulfonyl oxime, O-alkylsulfonyl oxime, etc. These may be used alone or in combination of two or more in admixture.

The above-mentioned sulfonium salt is a salt of a sulfonium cation and a sulfonate, a bis(substituted alkylsulfonyl) imide, or tris(substituted alkylsulfonyl)-methide, and the sulfonium cation may be mentioned that shown in the following general formula (5),

$$S^+(R^{33}R^{44}R^{55}) \quad (5)$$

wherein each of $R^{33}$, $R^{44}$, and $R^{55}$ independently represent a substituted or unsubstituted linear, branched, or cyclic alkyl group, an alkenyl group, or an oxoalkyl group each having 1 to 10 carbon atoms, or a substituted or unsubstituted aryl group, an aralkyl group, or aryloxoalkyl group having 6 to 18 carbon atoms; and any two of $R^{33}$, $R^{44}$, and $R^{55}$ may be bonded with each other to form a ring together with the sulfur atom in the formula.

The above-mentioned alkyl group may be specifically exemplified by a methyl group, an ethyl group, a n-propyl group, an isopropyl group, a n-butyl group, a tert-butyl group, a cyclopropyl group, a cyclopentyl group, a cyclohexyl group, a cyclopropylmethyl group, a 4-methylcyclohexyl group, a cyclohexylmethyl group, a norbornyl group, an adamantyl group, etc. The above-mentioned oxoalkyl group may be specifically exemplified by a 2-oxocyclopentyl group, a 2-oxocyclohexyl group, a 2-oxopropyl group, a 2-oxoethyl group, a 2-cyclopentyl-2-oxoethyl group, a 2-cyclohexyl-2-oxoethyl group, a 2-(4-methylcyclohexyl)-2-oxoethyl group, etc. The above-mentioned alkenyl group may be specifically exemplified by a vinyl group, an allyl group, a propenyl group, a butenyl group, a hexenyl group, a cyclohexenyl group, etc. The above-mentioned aryl group may be specifically exemplified by a phenyl group, a naphthyl group, a thienyl group, a hydroxyphenyl group such as a 4-hydroxyphenyl group, etc., an alkoxyphenyl group such as a 4-methoxyphenyl group, a 3-methoxyphenyl group, a 2-methoxyphenyl group, a 4-ethoxyphenyl group, a 4-tert-butoxyphenyl group, a 3-tert-butoxyphenyl group, etc., an alkylphenyl group such as a 2-methylphenyl group, a 3-methylphenyl group, a 4-methylphenyl group, a 4-ethylphenyl group, a 4-tert-butylphenyl group, a 4-n-butylphenyl group, a 2,4-dimethylphenyl group, etc., an alkylnaphthyl group such as a methylnaphthyl group, an ethylnaphthyl group, etc., an alkoxynaphthyl group such as a methoxynaphthyl group, an ethoxynaphthyl group, etc., a dialkylnaphthyl group such as a dimethylnaphthyl group, a diethylnaphthyl group, etc., and a dialkoxynaphthyl group such as a dimethoxynaphthyl group, a diethoxynaphthyl group, etc. The above-mentioned aralkyl group may be specifically exemplified by a benzyl group, a 1-phenylethyl group, a 2-phenylethyl group, etc. The above-mentioned aryloxoalkyl group may be specifically exemplified by a 2-aryl-2-oxoethyl group such as a 2-phenyl-2-oxoethyl group, a 2-(1-naphthyl)-2-oxoethyl group, a 2-(2-naphthyl)-2-oxoethyl group, etc. Also, a part of the hydrogen atom of these groups may be substituted by a fluorine atom or a hydroxyl group. Any two of $R^{33}$, $R^{44}$, and $R^{55}$ may be bonded to each other to form a ring together with the sulfur atom in the formula, and in such a case, the group represented by the following general formula, etc., may be mentioned.

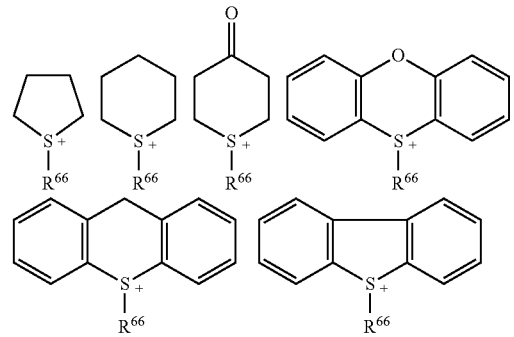

wherein $R^{66}$ represents the same groups as exemplified by the above $R^{33}$, $R^{44}$, and $R^{55}$.

As an anion species of the above sulfonium salt, the sulfonate may be exemplified by trifluoromethane sulfonate, pentafluoroethane sulfonate, heptafluoropropane sulfonate, nonafluorobutane sulfonate, tridecafluorohexane sulfonate, 2,2,2-trifluoroethane sulfonate, pentafluorobenzene sulfonate, 1,1-difluoro-2-naphthylethane sulfonate, 1,1,2,2-tetrafluoro-2-(norbornan-2-yl)ethane sulfonate, 1,1,2,2-tetrafluoro-2-(tetracyclo[6.2.1.1$^{3,6}$.0$^{2,7}$]dodeca-3-en-8-yl) ethanesulfonate, 2-benzoyloxy-1,1,3,3,3-pentafluoropropane sulfonate, 1,1-difluoro-2-tosyloxyethane sulfonate, adamantanemethoxycarbonyl difluoromethane sulfonate, 1-(3-hydroxymethyladamantane)methoxycarbonyl difluoromethane sulfonate, methoxycarbonyl difluoromethane sulfonate, 1-(hexahydro-2-oxo-3,5-methano-2H-cyclopenta[b]furan-6-yloxycarbonyl)difluoromethane sulfonate, 4-oxo-1-adamantyloxycarbonyl difluoromethane sulfonate, etc., bis(substituted alkylsulfonyl)imide may be exemplified by bis(trifluoromethylsulfonyl)imide, bis(pentafluoroethylsulfonyl)imide, bis(heptafluoropropylsulfonyl) imide, perfluoro(1,3-propylenebissulfonyl)imide, etc., tris (substituted alkylsulfonyl)methide may be exemplified by tris(trifluoromethylsulfonyl)methide, and a sulfonium salt may be mentioned those in which the above anion species and the cation species mentioned above are combined.

As to the above-mentioned iodonium salt, a N-sulfonyloxydicarboxylmide type photo-sensitive acid generator, an O-arylsulfonyloxime compound or an O-alkylsulfonyloxime compound (oxime sulfonate) type photo-sensitive acid generator, those compounds described in Japanese Patent Laid-Open Publication No. 2009-269953 may be mentioned.

Among these, as the other acid generator preferably used may be exemplified by triphenyl sulfonium nonafluorobutane sulfonate, triphenylsulfonium bis(trifluoromethylsulfonyl) imide, triphenylsulfonium perfluoro(1,3-propylenebissulfonyl)imide, triphenylsulfonium tris(trifluoromethane-sulfonyl)methide, N-nonafluorobutanesulfonyloxy-1,8-naphthalene dicarboxylmide, 2-(2,2,3,3,4,4-hexafluoro-1-(nonafluorobutylsulfonyloxyimino)butyl)fluorene, 2-(2,2,3, 3,4,4,5,5-octafluoro-1-(nonafluorobutylsulfonyloxyimino) pentyl)fluorene, etc.

A preferable structure of the photo-sensitive acid generator may be mentioned the compound represented by the following general formula (P1):

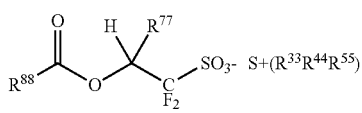

(P1)

wherein $R^{77}$ represents a hydrogen atom or a trifluoromethyl group; $R^{88}$ represents an alkyl group, an alkenyl group or, an aralkyl group having 1 to 30 carbon atoms which may contain a heteroatom; and $R^{33}$, $R^{44}$, and $R^{55}$ have the same meanings as defined above.

In the above-mentioned formula (P1), $R^{77}$ represents a hydrogen atom or a trifluoromethyl group. $R^{33}$, $R^{44}$, and $R^{55}$ have the same meanings as defined above. $R^{88}$ represents an alkyl group, an alkenyl group, or an aralkyl group each having 1 to 30 carbon atoms which may contain a heteroatom. The heteroatom contained in $R^{88}$ may be preferably an oxygen atom, a nitrogen atom, a sulfur atom, and a halogen atom, and an oxygen atom is more preferable. The alkyl group, the alkenyl group, and the aralkyl group having 1 to 30 carbon atoms of $R^{88}$ may be any of a linear, branched, or cyclic, and more preferably having 6 to 30 carbon atoms for the purpose of obtaining a high resolution in a fine patterning. When $R^{88}$ is an aryl group, it is not preferable since smoothness of the side wall of the resist pattern to be formed is inferior in some cases. $R^{88}$ may be specifically exemplified by a methyl group, an ethyl group, a propyl group, an isopropyl group, a butyl group, an isobutyl group, a sec-butyl group, a tert-butyl group, a pentyl group, a neopentyl group, a cyclopentyl group, a hexyl group, a cyclohexyl group, a 3-cyclohexenyl group, a heptyl group, a 2-ethylhexyl group, a nonyl group, an undecyl group, a tridecyl group, a pentadecyl group, a heptadecyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, a dicyclohexylmethyl group, an icosanyl group, an allyl group, a benzyl group, a diphenylmethyl group, a tetrahydrofuryl group, a methoxymethyl group, an ethoxymethyl group, a methylthiomethyl group, an acetamidemethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group and a 3-oxocyclohexyl group, but not limited to them.

With regard to synthesis of the sulfonium salt of the general formula (P1), it is described in detail in Japanese Patent Laid-Open Publication No. 2007-145797 (Patent Document 4), No. 2008-106045, No. 2009-7327, and No. 2009-258695.

Also, the sulfonium salt disclosed in Japanese Patent Laid-Open Publication No. 2010-215608 can be suitably used.

More preferable specific photo-sensitive acid generators are exemplified below.

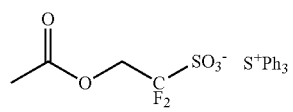

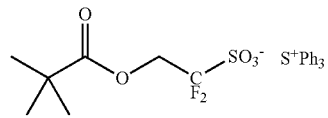

-continued

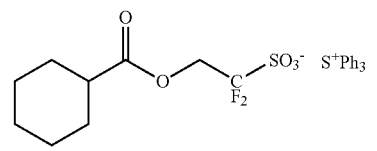

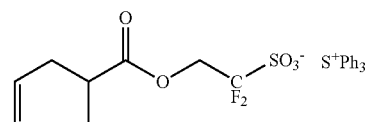

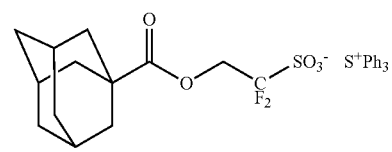

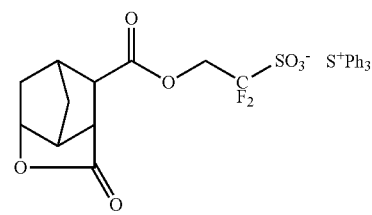

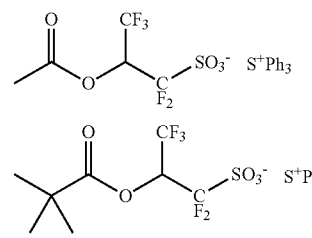

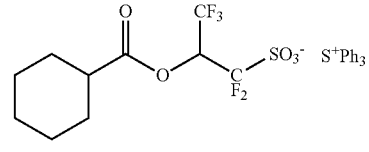

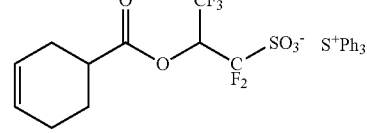

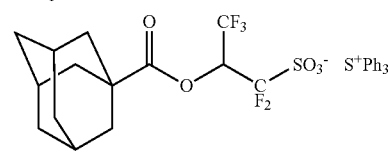

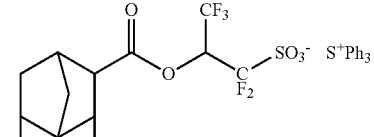

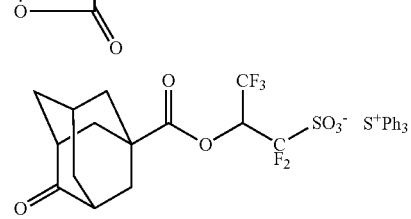

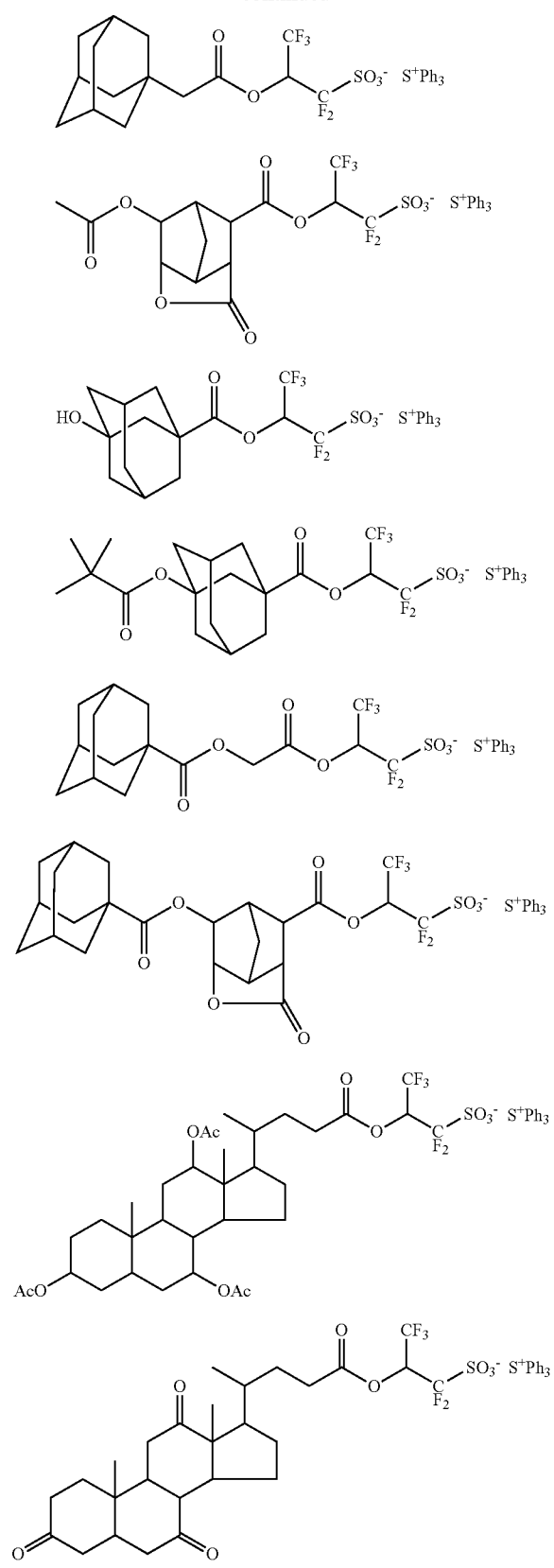
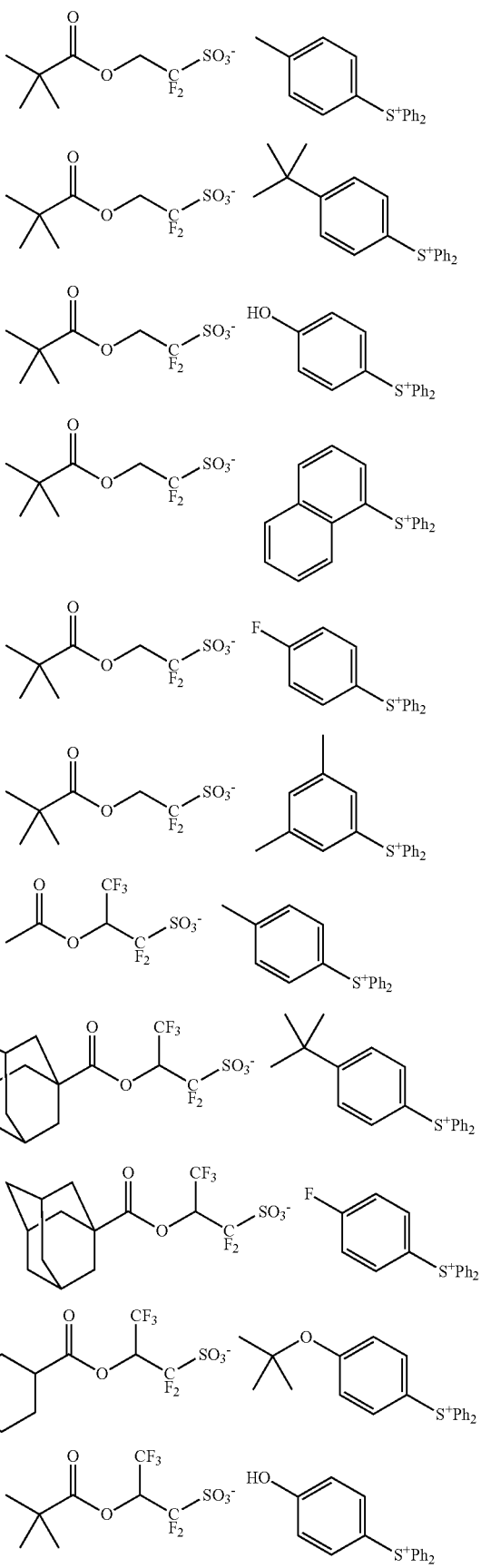
wherein Ac represents an acetyl group, and Ph represents a phenyl group.

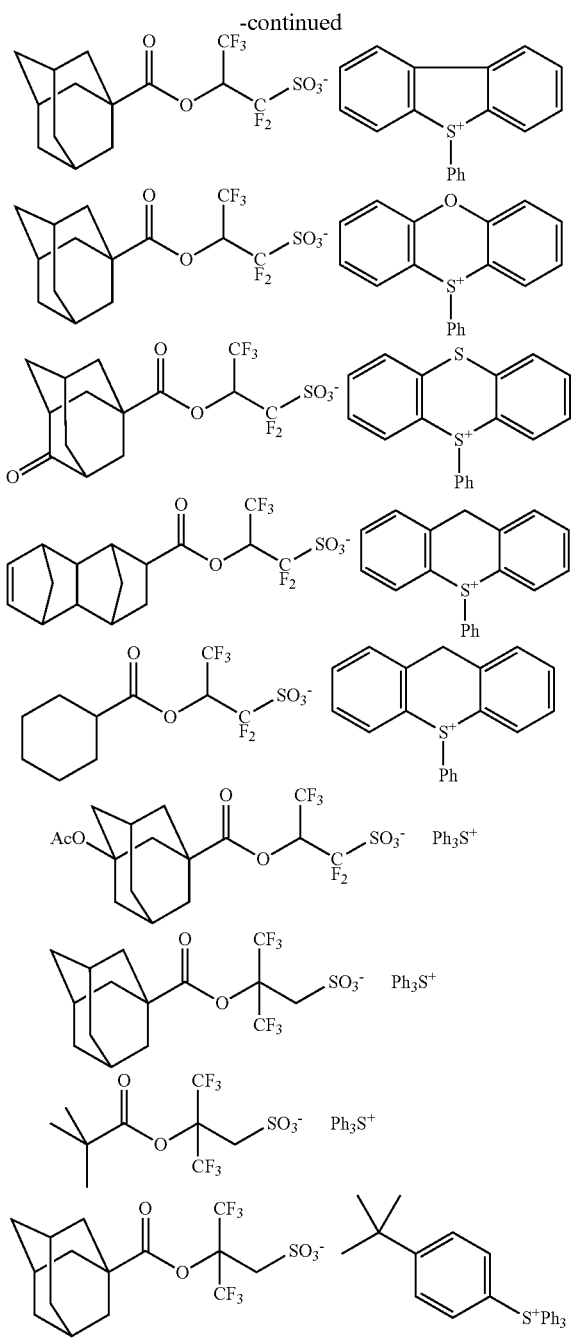

wherein Ac represents an acetyl group, and Ph represents a phenyl group.

An addition amount of these photo-sensitive acid generators (F) is 0 to 40 parts by mass relative to 100 parts by mass of the polymer compound in the resist composition, and if it is blended, it is preferably 0.1 to 40 parts by mass, further preferably 0.1 to 20 parts by mass. If the amount is too much, there is a fear of causing degradation of the resolution, or causing problems of foreign matters after resist development or at the time of peeling.

As the other photo-sensitive acid generators, a photo-sensitive acid generator having a nitrogen-containing substituent may be used. Such a compound functions as the so-called photodegradable base in which it acts as the quencher at the unexposed portion, and it lost the quencher function at the exposed portion by neutralization with the generated acid from itself. By using the photodegradable base, contrast at the exposed portion and the unexposed portion can be strengthened. The photodegradable base may be used by referring to, for example, Japanese Patent Laid-Open Publication No. 2009-109595, No. 2012-046501, etc.

Two or more kinds of the photo-sensitive acid generators (F) may be used, or it may be used in combination with the other acid generator. When the other acid generator is blended, an addition amount of the other acid generator may be an optional, and generally 0 to 20 parts by mass, preferably 0.1 to 10 parts by mass relative to 100 parts by mass of the base resin in the resist composition.

(G) Organic Acid Derivative and/or Fluorine Substituted Alcohol

The resist composition of the present invention may be added a compound (acid amplifier compound) which generates an acid by decomposing with an acid. These compounds can be referred to Japanese Patent Laid-Open Publication No. 2009-269953 or No. 2010-215608.

An addition amount of the acid amplifier compound in the resist composition of the present invention is 2 parts by mass or less, preferably 1 part by mass or less relative to 100 parts by mass of the base resin in the resist composition. If the amount is too much, control of diffusion is difficult and degradation of resolution or degradation of pattern shape occurs.

Further, addition of the organic acid derivative, or a compound (dissolution inhibitor) having a weight-average molecular weight of 3000 or less which changes solubility in an alkaline developing solution by the action of an acid is optional, and the compound described in Japanese Patent Laid-Open Publication No. 2009-269953 or No. 2010-215608 may be referred to similarly to the above-mentioned respective components.

In the present invention, as a third embodiment, a patterning process using the above-mentioned resist composition is provided.

For forming a pattern using the resist composition of the present invention, it may be carried out by employing the conventionally known lithography technology, for example, the composition is coated on a substrate for manufacturing an integrated circuit (Si, $SiO_2$, SiN, SiON, TiN, WSi, BPSG, SOG, an organic antireflection film, etc.), or a substrate for manufacturing a mask circuit (Cr, CrO, CrON, MoSi, etc.) by means of a spin coating, etc., so as to the film thickness of 0.05 to 2.0 μm, and the coated film is prebaked on a hot plate at 60 to 150° C. for 1 to 10 minutes, preferably at 80 to 140° C. for 1 to 5 minutes. Then, a mask for forming the objective pattern is placed over the resist film, and a high energy beam such as a far ultraviolet ray, an excimer laser, a X-ray, etc., or an electron beam is irradiated to the resist film in a dose of 1 to 200 $mJ/cm^2$, preferably 10 to 100 $mJ/cm^2$. Alternatively, direct drawning is done by an electron beam without via a mask for forming the pattern. The exposure is carried out by the usual exposing method, and an immersion method in which immersion is carried out between the mask and the resist film is preferably used. In such a case, it is possible to use a protective coat insoluble in water. Then, it is subjected to post exposure bake (PEB) on a hot plate at 60 to 150° C. for 1 to 5 minutes, preferably at 80 to 140° C. for 1 to 3 minutes. Further, development is carried out by using a developing solution comprising an aqueous alkaline solution such as tetramethyl ammonium hydroxide (TMAH), etc., with a concentration of 0.1 to 5% by mass, preferably 2 to 3% by mass, for 0.1 to 3 minutes, preferably 0.5 to 2 minutes, by the conventional method such as a dip method, a puddle method, a spray method, etc., whereby an objective pattern is formed on the substrate. Meanwhile, the resist composition of the present invention is most suitable for fine patterning, particularly by a KrF excimer laser, an ArF excimer laser, an electron beam, or a soft X-ray having in the wavelength range of 3 to 15 nm among the high energy beams.

The above-mentioned protective coat insoluble in water is used to prevent elution from the resist film and to improve water-sliding property of the film surface, and is roughly classified into two types. One type is an organic solvent-strippable type in which the protective coat must be stripped by an organic solvent which does not dissolve the resist film before the alkaline development, and another type is an alkali soluble type in which the protective coat which is soluble in an alkaline developing solution, and can be removed simultaneously with removal of soluble portion of the resist film.

As the latter protective coat, a material which comprises a polymer compound having a 1,1,1,3,3,3-hexafluoro-2-propanol residue which is insoluble in water and soluble in an alkaline developing solution, as a base material, which is dissolved in an alcohol solvent having 4 or more carbon atoms, an ether solvent having 8 to 12 carbon atoms, or a mixed solvent thereof is preferable.

Further, the above-mentioned surfactant which is insoluble in water and soluble in an alkaline developing solution may be added to the alcohol solvent having 4 or more carbon atoms, the ether solvent having 8 to 12 carbon atoms, or the mixed solvent thereof may be made.

In addition, as a means of the patterning process, after forming the photoresist film, rinsing with pure water (post soaking) may be carried out to extract the acid generator, etc., from the film surface or to wash away the particles, or rinsing (post soaking) may be carried out to remove water remained on the film after exposure.

Furthermore, as the life-prolonging technology to the 32 nm ArF lithography, a double patterning method may be mentioned. As to the double patterning method, a trench method of processing an underlay to a 1:3 trench pattern by a first time exposure and etching, shifting the position, and forming a 1:3 trench pattern by a second time exposure for forming a 1:1 pattern, and a line method of processing a first underlay to a 1:3 isolated left pattern by a first time exposure and etching, shifting the position, and processing a second underlay formed below the first underlay by a second time exposure to a 1:3 isolated left pattern for forming a half-pitch 1:1 pattern.

Meanwhile, the developing solution to be used in the patterning process of the present invention may be a developing solution of an aqueous alkaline solution such as tetramethyl ammonium hydroxide (TMAH), etc., with a concentration of 0.1 to 5% by mass, preferably 2 to 3% by mass as mentioned above, and a means of the negative tone development which develops/dissolves the unexposed portion by using an organic solvent may be used.

For the organic solvent development, as a developing solution, one or more selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate and 2-phenylethyl acetate can be used.

EXAMPLES

In the following, the present invention is described specifically by referring to Synthesis Examples, Examples, and Comparative Examples, but the present invention is not limited by the following Examples.

Synthesis Example 1

The sulfonium salt of the present invention is synthesized by the method as mentioned below.

Synthesis Example 1-1

Synthesis of triethyl ammonium=2-(adamantane-1-carbonyloxy)-3,3,3-trifluoro-2-trifluoromethylpropane-1-sulfonate According to the method described in Japanese Patent Laid-Open Publication No. 2010-215608, an aqueous solution of sodium 3,3,3-trifluoro-2-hydroxy-2-trifluoromethylpropane-1-sulfonate was synthesized. Then, to 1320 g of the aqueous solution (corresponding to 1 mol of sodium 3,3,3-trifluoro-2-hydroxy-2-trifluoromethylpropane-1-sulfonate) were added 152 g of triethylamine and 104 g of 35% hydrochloric acid and after the mixture was stirred for 10 minutes, the reaction solution was concentrated. To this were added 111 g of triethylamine, 12 g of N,N-dimethyl-4-aminopyridine, and 2000 g of methylene chloride. To this mixed solution was added a mixed solution comprising 250 g of 1-adamantanecarbonyl chloride and 250 g of methylene chloride under ice-cooling, the resulting mixture was stirred at room temperature overnight, and then, 1000 g of water was added to the reaction mixture to stop the reaction. The liquids of the quenched reaction mixture were separated; the extracted organic layer was washed with an aqueous triethylamine hydrochloride solution, and then, washed with water. Thereafter, the organic layer was concentrated, methyl isobutyl ketone was added, and the solution was again concentrated. To the concentrated solution was added diisopropyl ether for recrystallization, the deposited solid was recovered, and dried under reduced pressure to obtain 392 g of triethyl ammonium=2-(adamantane-1-carbonyloxy)-3,3,3-trifluoro-2-trifluoromethylpropane-1-sulfonate which is an objective product as a reddish brown solid (Yield: 74%).

Synthesis Example 1-2

Synthesis of 1-(2,2,2-trifluoroethoxy)naphthalene

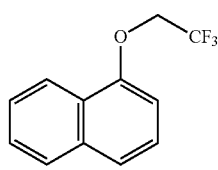 [SMILES: FC(F)(F)COc1cccc2ccccc12]

Under nitrogen atmosphere, a suspended liquid comprising 340 g of 1-naphthol, 400 g of p-toluenesulfonic acid=2,2,2-trifluoroethyl, 330 g of potassium carbonate and 800 g of dimethyl sulfoxide was stirred at 100° C. for 12 hours. After cooling, 1000 g of water and 2000 g of toluene were added, and the organic layer was collected by separation, and washed with 1000 g of 5% by mass aqueous sodium hydroxide solution five times. Subsequently, after further washing with 1,000 g of water four times, the organic layer was concentrated to obtain 360 g of an oily product. This was distilled under reduced pressure (75° C./13 Pa) to obtain 280 g of the objective product (Yield: 76%).

Synthesis Example 1-3

Synthesis of 4-(2,2,2-trifluoroethoxy)-1-naphthyltetrahydrothiophenium=2-(adamantane-1-carbonyloxy)-3,3,3-trifluoro-2-trifluoromethylpropane-1-sulfonate (PAG-1)

PAG-1

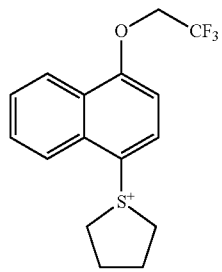

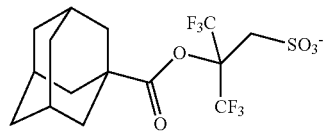

After 233 g of 1-(2,2,2-trifluoroethoxy)naphthalene synthesized in Synthesis Example 1-2 was dispersed in 462 g of Eaton's reagent (diphosphorus pentaoxide-methanesulfonic acid solution) available from Sigma-Aldrich Co., LLC, and 104 g of tetramethylene sulfoxide was added dropwise under ice-cooling and mixed. Aging was carried out at room temperature overnight, 700 g of water and 600 g of diisopropyl ether were added to the mixture under ice-cooling, and the aqueous layer was collected by separation. The aqueous layer was again washed with 600 g of diisopropyl ether, to prepare 4-(2,2,2-trifluoroethoxy)-1-naphthyltetrahydrothiophenium=methanesulfonate as an aqueous solution. To 590 g (corresponding to 0.39 mol) of the aqueous solution were added 160 g of triethyl ammonium=2-(adamantane-1-carbonyloxy)-3,3,3-trifluoro-2-trifluoromethylpropane-1-sulfonate synthesized in Synthesis Example 1-1, 1000 g of methylene chloride and 200 g of water, and the organic layer was extracted from the mixed solution. The extracted organic layer was washed and then concentrated, methyl isobutyl ketone was added to the concentrate, and the mixture was again concentrated. Diisopropyl ether was added to the concentrated solution for recrystallization, and the deposited solid was recovered and dried under reduced pressure to obtain 209 g of 4-(2,2,2-trifluoroethoxy)-1-naphthyltetrahydrothiophenium=2-(adamantane-1-carbonyloxy)-3,3,3-trifluoro-2-trifluoromethylpropane-1-sulfonate (Yield: 93%) which is an objective product as a white solid.

Figure 2:
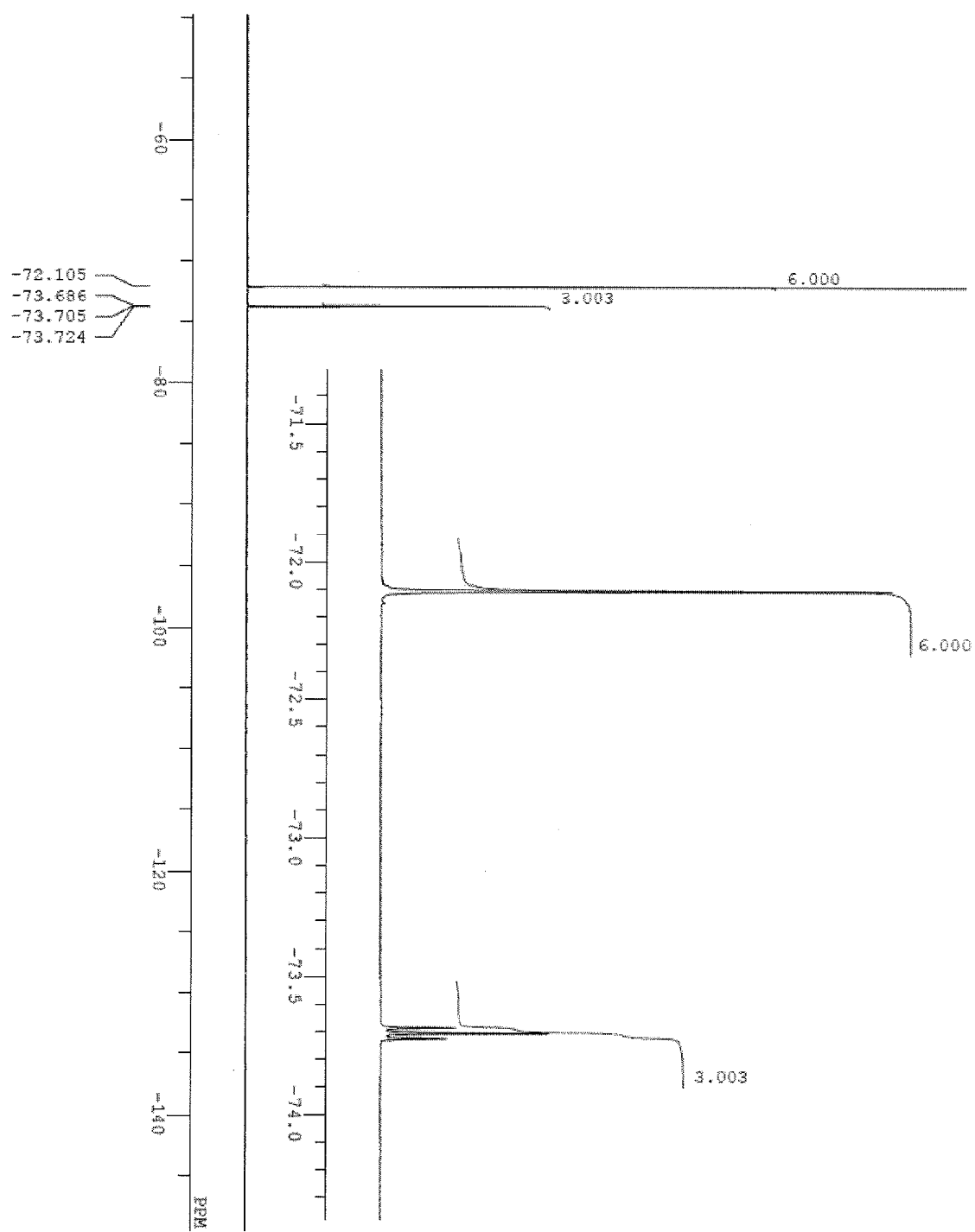
FIG. 2 shows $^{19}$F-NMR/DMSO-$d_6$ of the objective compound PAG-1 obtained in Synthesis Example 1-3.

Here, the spectral data of the obtained objective product were analyzed, and confirmed that it was certainly PAG-1 (FIGS. 1 and 2). The spectral data of the obtained objective product are shown in the following. The results of the nuclear magnetic resonance spectrum ($^1$H-NMR, $^{19}$F-NMR/DMSO-$d_6$) are shown in FIG. 1 and FIG. 2. Meanwhile, in $^1$H-NMR, a minute amount of residual solvents (methyl isobutyl ketone, diisopropyl ether, water) were observed.

IR (D-ATR): ν=2909, 1758, 1379, 1329, 1302, 1265, 1239, 1191, 1159, 1123, 1104, 1063, 1041, 1016, 969, 755, 596 cm$^{-1}$.

Time of flight mass spectrometry (TOFMS; MALDI)

POSITIVE M$^+$313 (corresponding to $C_{16}H_{16}F_3OS^+$)

NEGATIVE M$^-$423 (corresponding to $(C_{10}H_{15}COO)$—C$(CF_3)_2$—$CH_2SO_3^-$)

Synthesis Example 2

A polymer compound to be used for the resist composition of the present invention was synthesized by the formulation shown below. Meanwhile, the term "GPC" in the following examples means gel permeation chromatography, and a weight-average molecular weight (Mw) of the obtained polymer compound was measured by gel permeation chromatography (GPC) using tetrahydrofuran as a solvent and shown in terms of a polystyrene converted value.

Synthesis Example 2-1

Synthesis of Polymer Compound (P-1)

Under nitrogen atmosphere, 3.9 g of methacrylate=3-hydroxy-1-adamantyl, 18.0 g of methacrylate=3-ethyl-3-exo-tetracyclo[4.4.0.1$^{2,5}$.1$^{7,10}$]dodecyl, 18.3 g of methacrylate=4,8-dioxatricyclo[4.2.1.0$^{3,7}$]nonane-5-one-2-yl, 0.38 g of V-601 (available from Wako Pure Chemical Industries, Ltd.), 0.48 g of 2-mercaptoethanol, 24 g of PGMEA (propylene glycol methyl ether acetate) and 31 g of γ-butyrolactone were charged to prepare a monomers-polymerization initiator solution. In another flask an atmosphere of which was made nitrogen were charged 8.0 g of PMA (propylene glycol methyl ether acetate) and 10.5 g of γ-butyrolactone, the mixture was heated to 80° C. under stirring, and then, the above-mentioned monomers-polymerization initiator solution was added dropwise thereinto over 4 hours. After completion of the dropwise addition, stirring was continued for 2 hours while maintaining the temperature of the polymer solution at 80° C., and then, the mixture was cooled to room temperature. The obtained polymer solution was added dropwise into vigorously stirred 640 g of 10 wt % water-containing methanol, and the deposited copolymer was separated by filtration. The copolymer was washed twice with 240 g of methanol, dried under vacuum at 50° C. for 20 hours to obtain 35.3 g of white powder state copolymer (Yield: 88%). When it was analyzed by GPC, a weight-average molecular weight (Mw) in terms of the polystyrene was 6520, and a degree of dispersion thereof was 1.86.

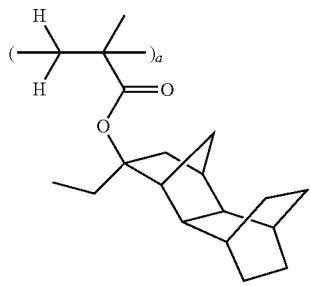
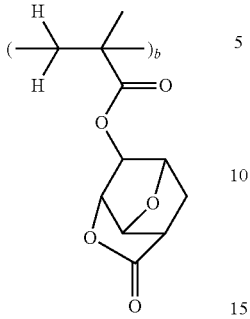

(P-1)

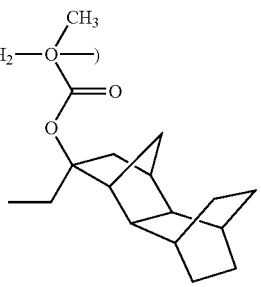

A-1

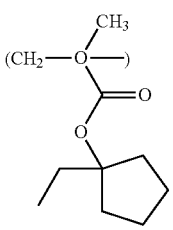

A-2

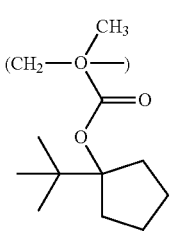

A-3

(a = 0.40, b = 0.50, c = 0.10)

Synthesis Examples 2-2 to 2-11

Synthesis of P-2 to P-11

According to the same operations as in the above-mentioned Synthesis Example 2-1 except for changing a kind of the respective monomers and a blending ratio thereof, polymer compounds were manufactured.

The manufactured resins (polymer compounds) are shown in the following Table 1. Meanwhile, in Table 1, the introducing ratio means a molar ratio. Also, the structures of the respective units in Table 1 are shown in Table 2 and Table 3.

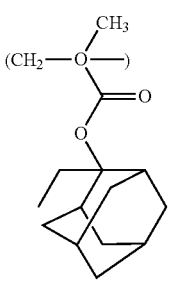

A-4

TABLE 1

| Resin | Unit 1 (introducing ratio) | | Unit 2 (introducing ratio) | | Unit 3 (introducing ratio) | | Unit 4 (introducing ratio) | |
|---|---|---|---|---|---|---|---|---|
| P-1 | A-1 | (0.40) | B-1 | (0.50) | B-6 | (0.10) | — | |
| P-2 | A-1 | (0.25) | A-2 | (0.35) | B-1 | (0.30) | B-6 | (0.10) |
| P-3 | A-4 | (0.50) | B-2 | (0.40) | B-6 | (0.10) | — | |
| P-4 | A-5 | (0.30) | A-6 | (0.20) | B-1 | (0.40) | B-6 | (0.10) |
| P-5 | A-3 | (0.50) | B-1 | (0.50) | — | | — | |
| P-6 | A-3 | (0.50) | B-5 | (0.40) | B-6 | (0.10) | — | |
| P-7 | A-3 | (0.50) | B-1 | (0.20) | B-4 | (0.30) | — | |
| P-8 | A-3 | (0.50) | B-3 | (0.20) | B-4 | (0.30) | — | |
| P-9 | A-2 | (0.25) | A-5 | (0.25) | B-4 | (0.35) | B-6 | (0.15) |
| P-10 | A-3 | (0.25) | A-5 | (0.25) | B-4 | (0.35) | B-6 | (0.15) |
| P-11 | A-3 | (0.25) | A-5 | (0.25) | B-5 | (0.35) | B-6 | (0.15) |

TABLE 2

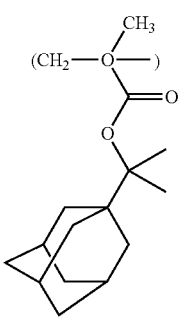

A-5

TABLE 2-continued

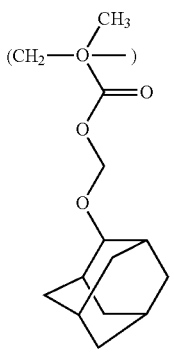
A-6

TABLE 3

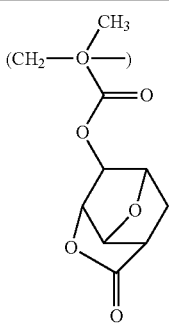
B-2

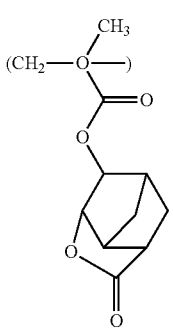
B-3

TABLE 2-continued

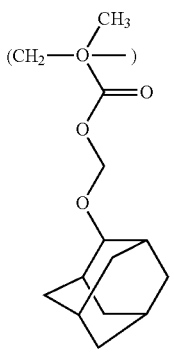
A-6

TABLE 3

B-1

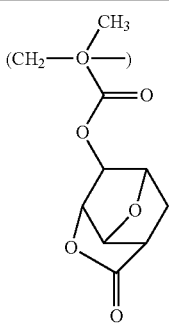

B-2

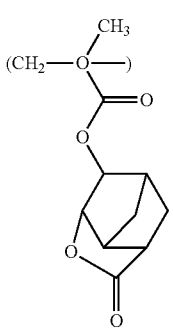

B-3

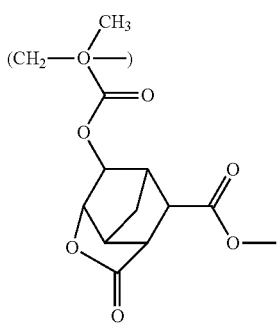

TABLE 3-continued

B-4

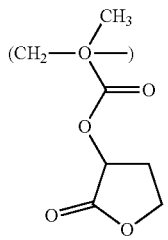

B-5

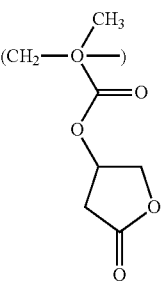

B-6

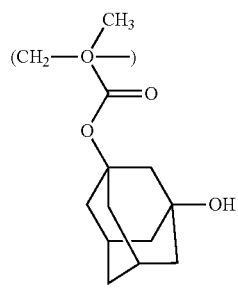

Preparation of Resist Solution

By using the sulfonium salts and the polymer compounds shown in the above-mentioned Synthesis Examples, the following quencher was dissolved in a solvent containing 0.01% by mass of the following surfactant A (available from Omnova Solutions, Inc.) with the composition shown in the following Table 4 to prepare a resist composition, and further the resist composition was filtered through a 0.2 μm filter made of Teflon (Registered Trademark) to prepare each resist solution.

Meanwhile, in Table 4, a basic compound (Q-1), a solvent, an alkali soluble type surfactant (SF-1), and a sulfonium salt other than the sulfonium salt shown in the above-mentioned Synthesis Examples which were used as a resist composition with the sulfonium salt and the polymer compound shown in the above-mentioned Synthesis Examples, are as shown below.

Q-1: 1-benzyloxycarbonyl-2-phenylbenzimidazole
PGMEA: propylene glycol monomethyl ether acetate
GBL: γ-butyrolactone
PAG-X: triphenylsulfonium=2-(adamantane-1-carbonyloxy)-3,3,3-trifluoro-2-trifluoromethylpropane-1-sulfonate
PAG-Y: 4-(2,2,2-trifluoroethoxy)-1-naphthyltetrahydrothiophenium=2-(adamantane-1-carbonyloxy)-1,1,3,3,3-pentafluoropropane-1-sulfonate
PAG-Z: triphenylsulfonium=2-(adamantane-1-carbonyloxy)-1,1,3,3,3-pentafluoropropane-1-sulfonate Alkali soluble type surfactant (SF-1): Poly(methacrylate=3,3,3-trifluoro-2-hydroxy-1,1-dimethyl-2-trifluoromethylpropyl.methacrylate=1,1,1-trifluoro-2-hydroxy-6-methyl-2-trifluoromethylhepta-4-yl) represented by the following general formula (compound described in Japanese Patent Laid-Open Publication No. 2008-122932)

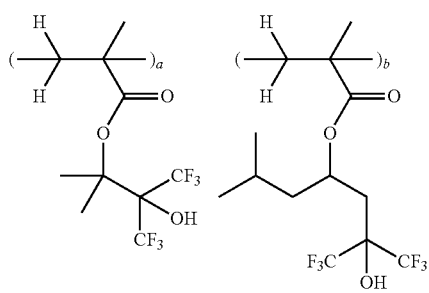

(a = 0.5 b = 0.5, Mw = 7,300)

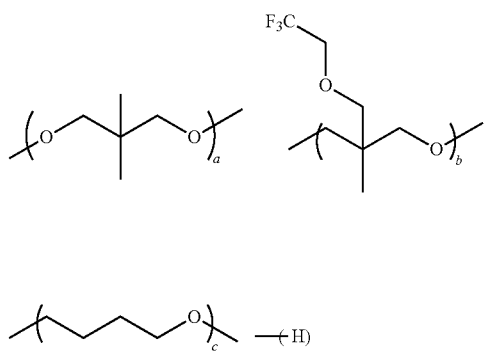

a:(b + b'):(c + c') = 1:4~7:0.01~1 (Mole ratio)
Weight-average molecular weight: 1,500

TABLE 4

| Resist | Resin (Polymer compound) (parts by mass) | | Acid generator (parts by mass) | | Basic compound (parts by mass) | | Surfactant (parts by mass) | | Solvent 1 (parts by mass) | | Solvent 2 (parts by mass) | |
|---|---|---|---|---|---|---|---|---|---|---|---|---|
| R-01 | P-1 | (80) | PAG-1 | (14.3) | Q-1 | (1.4) | SF-1 | (5.0) | PGMEA | (1728) | GBL | (192) |
| R-02 | P-2 | (80) | PAG-1 | (14.3) | Q-1 | (1.4) | SF-1 | (5.0) | PGMEA | (1728) | GBL | (192) |
| R-03 | P-3 | (80) | PAG-1 | (14.3) | Q-1 | (1.4) | SF-1 | (5.0) | PGMEA | (1728) | GBL | (192) |
| R-04 | P-4 | (80) | PAG-1 | (14.3) | Q-1 | (1.4) | SF-1 | (5.0) | PGMEA | (1728) | GBL | (192) |
| R-05 | P-5 | (80) | PAG-1 PAG-X | (10.0) (4.0) | Q-1 | (1.4) | SF-1 | (5.0) | PGMEA | (1728) | GBL | (192) |
| R-06 | P-6 | (80) | PAG-1 PAG-X | (10.0) (4.0) | Q-1 | (1.4) | SF-1 | (5.0) | PGMEA | (1728) | GBL | (192) |
| R-07 | P-7 | (80) | PAG-1 PAG-X | (10.0) (4.0) | Q-1 | (1.4) | SF-1 | (5.0) | PGMEA | (1728) | GBL | (192) |
| R-08 | P-8 | (80) | PAG-1 PAG-X | (10.0) (4.0) | Q-1 | (1.4) | SF-1 | (5.0) | PGMEA | (1728) | GBL | (192) |
| R-09 | P-9 | (80) | PAG-1 PAG-X | (15.0) (6.0) | Q-1 | (1.4) | SF-1 | (5.0) | PGMEA | (1728) | GBL | (192) |
| R-10 | P-10 | (80) | PAG-1 PAG-X | (10.0) (4.0) | Q-1 | (1.4) | SF-1 | (5.0) | PGMEA | (1728) | GBL | (192) |
| R-11 | P-11 | (80) | PAG-1 PAG-Z | (10.0) (3.8) | Q-1 | (1.4) | SF-1 | (5.0) | PGMEA | (1728) | GBL | (192) |
| R-12 | P-1 | (80) | PAG-X | (13.3) | Q-1 | (1.4) | SF-1 | (5.0) | PGMEA | (1728) | GBL | (192) |
| R-13 | P-1 | (80) | PAG-Y | (10.9) | Q-1 | (1.4) | SF-1 | (5.0) | PGMEA | (1728) | GBL | (192) |
| R-14 | P-1 | (80) | PAG-Z | (10.1) | Q-1 | (1.4) | SF-1 | (5.0) | PGMEA | (1728) | GBL | (192) |

Surfactant A:

3-methyl-3-(2,2,2-trifluoroethoxymethyl)oxetane.tetrahydrofuran.2,2-dimethyl-1,3-propanediol copolymer (available from Omnova Solutions, Inc.) (represented by the following general formula),

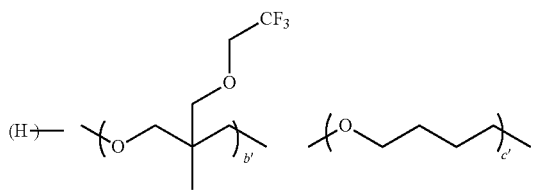

Evaluation of Resist Compositions: ArF Exposure (1)

Examples 1-1 to 1-11

Comparative Examples 1-1 to 1-3

On an antireflection film (film thickness: 100 nm) substrate which has been prepared by coating an antireflection film solution (ARC-29A available from Nissan Chemical Industries, Ltd.) on a silicon substrate and baked at 200° C. for 60 seconds was spin coated the resist solution, and baked by using a hot plate at 100° C. for 60 seconds to prepare a resist film having a thickness of 90 nm. This was immersion exposed by using an ArF excimer laser scanner (NSR-S610C manufactured by Nikon Corporation, NA=1.30, dipolar, Cr mask), baked (PEB) at 80° C. for 60 seconds, and developed by an aqueous solution of 2.38% by mass of tetramethyl ammonium hydroxide for 60 seconds.

(Evaluation Method)

Evaluation of the resist was objected the 1:1 line and space pattern with 40 nm, which was observed by an electron microscope, and an exposure dose which gave a line dimensional width of 40 nm was made the optimum exposure dose (Eop, mJ/cm$^2$). A pattern shape at the optimum exposure dose was compared, and the quality was judged.

Further, line width fluctuation at the line portion of the 1:1 line and space with 40 nm was measured by SEM, and the result was shown by a line width roughness (LWR) (measured 30 points, and calculated 3σ value). The smaller LWR value indicates small fluctuation in line pattern and means good.

In this evaluation method, "good" was made 3.0 nm or less and "bad" 3.1 nm or more.

Evaluation of an eluted amount of the sulfonium salt into immersion water was carried out as follows: First, on a wafer on which the resist film has been formed by the above-mentioned method was placed a Teflon (Registered Trademark) ring with a complete circle shape and having an inner diameter of 10 cm, and 10 ml of pure water was carefully poured thereinto to contact the resist film and pure water at room temperature for 60 seconds. Thereafter, pure water was recovered, and a cation component concentration (mol/cm$^2$·sec) of the sulfonium salt in the pure water was measured by an LC-MS analytical device (manufactured by Agilent Technologies Co., Ltd.).

Evaluation results of the respective resist compositions are shown in Table 5.

TABLE 5

| | Resist | Optimum exposure dose (mJ/cm$^2$) | LWR (nm) | Pattern shape | Cation component concentration (×10$^{-13}$ mol/cm$^2$·sec) |
|---|---|---|---|---|---|
| Example 1-1 | R-01 | 37 | 3.0 | Rectangular | 2.2 |
| Example 1-2 | R-02 | 38 | 2.9 | Rectangular | 2.4 |
| Example 1-3 | R-03 | 42 | 3.0 | Rectangular | 2.3 |
| Example 1-4 | R-04 | 32 | 2.9 | Rectangular | 2.2 |
| Example 1-5 | R-05 | 34 | 2.7 | Rectangular | 2.9 |
| Example 1-6 | R-06 | 32 | 2.9 | Rectangular | 2.8 |
| Example 1-7 | R-07 | 33 | 2.7 | Rectangular | 3.2 |
| Example 1-8 | R-08 | 33 | 2.8 | Rectangular | 2.9 |
| Example 1-9 | R-09 | 34 | 2.9 | Rectangular | 3.0 |
| Example 1-10 | R-10 | 36 | 2.7 | Rectangular | 3.1 |
| Example 1-11 | R-11 | 36 | 2.7 | Rectangular | 3.1 |
| Comparative Example 1-1 | R-12 | 37 | 3.2 | Inferior, footing | 9.8 |
| Comparative Example 1-2 | R-13 | 36 | 3.6 | Inferior, slightly footing | 2.6 |
| Comparative Example 1-3 | R-14 | 34 | 3.4 | Inferior, footing | 9.6 |

From the results of Table 5, it was shown that the resist compositions of the present invention were excellent in pattern shape and LWR. Also, in the resist films of Examples 1-1 to 1-11 into which the sulfonium salts of the present invention have been blended, it could be admitted that elution (leaching) of the sulfonium salt component from the resist film to water was low as compared with those of the resist films of Comparative Examples 1-1 and 1-3. In Comparative Example 1-2, whereas leaching showed a low value, but LWR and a shape were bad. Accordingly, it was shown that the resist compositions using the sulfonium salts of the present invention were suitable as a material for an immersion lithography as compared with any of the resist compositions used in Comparative Examples 1-1 to 1-3.

Evaluation of Resist Compositions: ArF Exposure (2)

Examples 2-1 to 2-11, Comparative Examples 2-1 to 2-3

After the spin-on carbon film ODL-50 (80% by mass of the carbon content, manufactured by Shin-Etsu Chemical Co., Ltd.) was applied on a silicon wafer with the film thickness of 200 nm, the silicon-containing spin-on hard mask SHB-A940 (43% by mass of the silicon content) was formed on it with the film thickness of 35 nm to obtain a substrate for a tri-layer process. Onto the substrate thus prepared was applied by spin coating each of the resist compositions prepared according to Table 4; and then, this was baked on a hot plate at 100° C. for 60 seconds to obtain the resist film having film thickness of 100 nm.

This was exposed by using an ArF excimer laser immersion scanner (NSR-610C manufactured by Nikon Corporation, NA: 1.30, σ: 0.98/0.78, cross pole aperture 20 degree, Azimuthally polarized illumination, 6% halftone phase shift mask, a lattice shaped mask having a wafer upper dimension with a pitch of 90 nm and a line width of 30 nm) while changing the exposure dose, and after the exposure, baked (PEB) at 80° C. for 60 seconds. Then, butyl acetate was discharged from a development nozzle while rotating the same for 3 seconds with 30 rpm, thereafter, subjected to static paddle development for 27 seconds, rinsed by diisoamyl ether and spin dried, and baked at 100° C. for 20 seconds to evaporate the rinsing solvent to obtain a negative type pattern.

Dimensions of 50 portions of the image-reversed hole patterns by the solvent development were measured by TDSEM (CG-4000) manufactured by Hitachi High-Technologies Corporation, and fluctuation of the dimensions 3σ was obtained. Cross-section shape of the hole pattern was observed by an electron microscope S-4300 manufactured by Hitachi High-Technologies Corporation. The results are shown in Table 6.

TABLE 6

| | Resist | Optimum exposure dose (mJ/cm$^2$) | Pattern shape | Hole dimension fluctuation (nm) |
|---|---|---|---|---|
| Example 2-1 | R-01 | 38 | Vertical | 2.8 |
| Example 2-2 | R-02 | 40 | Vertical | 2.6 |
| Example 2-3 | R-03 | 43 | Vertical | 2.8 |
| Example 2-4 | R-04 | 33 | Vertical | 2.7 |
| Example 2-5 | R-05 | 35 | Vertical | 2.3 |
| Example 2-6 | R-06 | 33 | Vertical | 2.6 |
| Example 2-7 | R-07 | 35 | Vertical | 2.2 |
| Example 2-8 | R-08 | 34 | Vertical | 2.4 |
| Example 2-9 | R-09 | 37 | Vertical | 2.5 |
| Example 2-10 | R-10 | 37 | Vertical | 2.5 |
| Example 2-11 | R-11 | 37 | Vertical | 2.7 |
| Comparative Example 2-1 | R-12 | 39 | Reversed taper | 3.6 |
| Comparative Example 2-2 | R-13 | 37 | Reversed taper | 3.7 |
| Comparative Example 2-3 | R-14 | 35 | Reversed taper | 3.9 |

From the results shown in Table 6, it was shown that the resist compositions of the present invention gave vertical pattern excellent in dimensional uniformity of the pattern after the organic solvent development.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:

1. A sulfonium salt represented by the following general formula (1a),

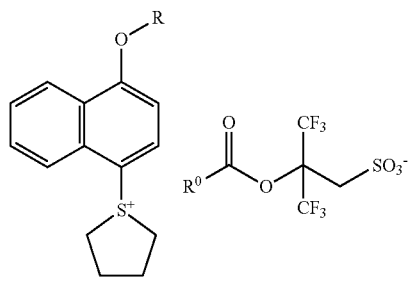
(1a)

wherein R represents a linear, branched, or cyclic monovalent hydrocarbon group having 1 to 30 carbon atoms at least one or more of hydrogen atoms of which are substituted by a fluorine atom, and $R^0$ represents a hydrogen atom, or a linear, branched, or cyclic monovalent hydrocarbon group having 1 to 30 carbon atoms which may be substituted by a halogen atom, or interposed by a heteroatom.

2. The sulfonium salt according to claim 1, wherein the general formula (1a) is represented by the following general formula (1b),

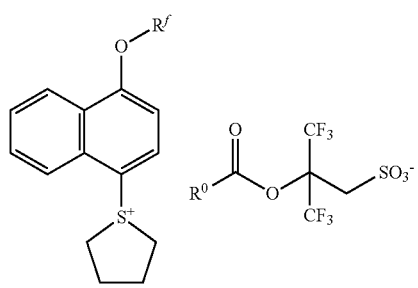
(1b)

wherein $R^0$ is as defined above, and $R^f$ represents an alkyl group having 1 to 4 carbon atoms at least one or more hydrogen atoms of which are substituted by a fluorine atom.

3. A chemically amplified resist composition which comprises a base resin, an acid generator, and an organic solvent, wherein the acid generator is the sulfonium salt according to claim 1.

4. A chemically amplified resist composition which comprises a base resin, an acid generator, and an organic solvent, wherein the acid generator is the sulfonium salt according to claim 2.

5. The chemically amplified resist composition according to claim 3, wherein the base resin is a polymer compound having a repeating unit represented by the following general formula (2) and a repeating unit represented by the following general formula (3),

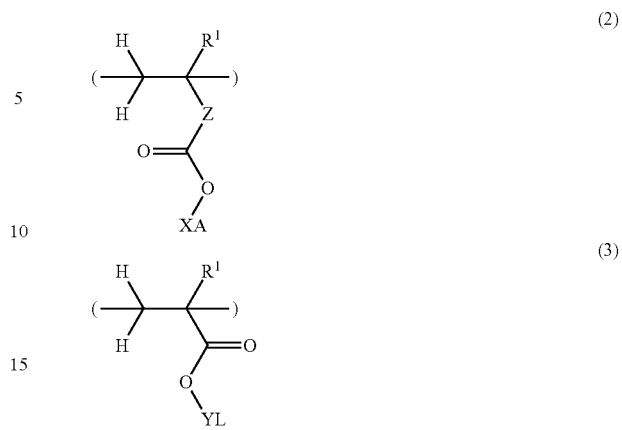

wherein $R^1$ represents a hydrogen atom, a fluorine atom, a methyl group or a trifluoromethyl group; Z represents any of a single bond, a phenylene group, a naphthylene group, and a (main chain)-C(=O)—O—Z'—; Z' represents a phenylene group, a naphthylene group, or a linear, branched, or cyclic alkylene group having 1 to 10 carbon atoms which may have any of a hydroxyl group, an ether bond, an ester bond, and a lactone ring; XA represents an acid-labile group; and YL represents a hydrogen atom, or a polar group having one or more structures selected from a hydroxyl group, a cyano group, a carbonyl group, a carboxyl group, an ether bond, an ester bond, a sulfonate ester bond, a carbonate bond, a lactone ring, a sultone ring, and a carboxylic acid anhydride.

6. The chemically amplified resist composition according to claim 4, wherein the base resin is a polymer compound having a repeating unit represented by the following general formula (2) and a repeating unit represented by the following general formula (3),

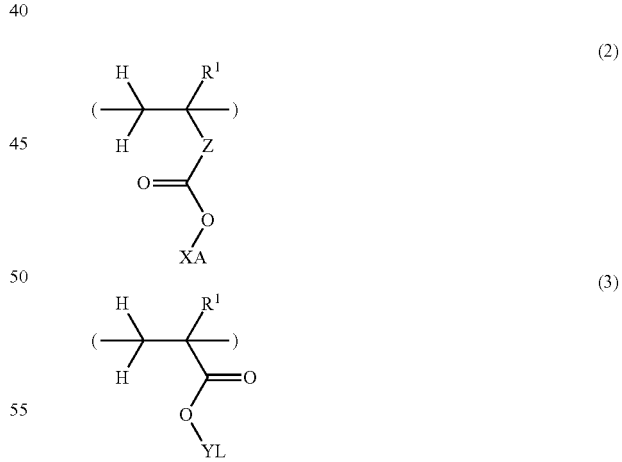

wherein $R^1$ represents a hydrogen atom, a fluorine atom, a methyl group or a trifluoromethyl group; Z represents any of a single bond, a phenylene group, a naphthylene group, and a (main chain)-C(=O)—O—Z'—; Z' represents a phenylene group, a naphthylene group, or a linear, branched, or cyclic alkylene group having 1 to 10 carbon atoms which may have any of a hydroxyl group, an ether bond, an ester bond, and a lactone ring; XA represents an acid-labile group; and YL represents a hydrogen atom, or a polar group having one or more structures selected from a hydroxyl group, a cyano group, a carbonyl group, a carboxyl group, an ether bond, an ester bond, a sulfonate ester bond, a carbonate bond, a lactone ring, a sultone ring, and a carboxylic acid anhydride.

7. The chemically amplified resist composition according to claim 3, wherein the chemically amplified resist composition contains further at least any one of a basic compound and a surfactant.

8. The chemically amplified resist composition according to claim 4, wherein the chemically amplified resist composition contains further at least any one of a basic compound and a surfactant.

9. The chemically amplified resist composition according to claim 5, wherein the chemically amplified resist composition contains further at least any one of a basic compound and a surfactant.

10. The chemically amplified resist composition according to claim 6, wherein the chemically amplified resist composition contains further at least any one of a basic compound and a surfactant.

11. A patterning process comprising a step of applying the chemically amplified resist composition according to claim 3 onto a substrate, a step of exposure by a high energy beam after heat treatment, and a step of development by using a developing solution.

12. A patterning process comprising a step of applying the chemically amplified resist composition according to claim 4 onto a substrate, a step of exposure by a high energy beam after heat treatment, and a step of development by using a developing solution.

13. The patterning process according to claim 11, wherein the exposure is conducted by an immersion exposure interposed by a liquid having a refractive index of 1.0 or more between a resist coat film and a projection lens.

14. The patterning process according to claim 12, wherein the exposure is conducted by an immersion exposure interposed by a liquid having a refractive index of 1.0 or more between a resist coat film and a projection lens.

15. The patterning process according to claim 13, wherein a protective coat is further applied on the resist coat film, and then the immersion exposure is conducted interposed by the liquid between the protective coat and the projection lens.

16. The patterning process according to claim 14, wherein a protective coat is further applied on the resist coat film, and then the immersion exposure is conducted interposed by the liquid between the protective coat and the projection lens.

17. The patterning process according to claim 11, wherein the high energy beam for exposure is a KrF excimer laser, an ArF excimer laser, an electron beam, or a soft X-ray in the wavelength range of 3 to 15 nm.

18. The patterning process according to claim 12, wherein the high energy beam for exposure is a KrF excimer laser, an ArF excimer laser, an electron beam, or a soft X-ray in the wavelength range of 3 to 15 nm.

* * * * *